(12) United States Patent
Hutchinson et al.

(10) Patent No.: US 6,943,017 B2
(45) Date of Patent: Sep. 13, 2005

(54) METHOD OF PRODUCING ANTIHYPERCHOLESTEROLEMIC AGENTS

(75) Inventors: Charles R. Hutchinson, Oakland, CA (US); Jonathan Kennedy, Hayward, CA (US); Cheonseok Park, Seoul (KR)

(73) Assignee: Wisconsin Alumni Research Foundation, Madison, WI (US)

( * ) Notice: Subject to any disclaimer, the term of this patent is extended or adjusted under 35 U.S.C. 154(b) by 206 days.

(21) Appl. No.: 10/109,310

(22) Filed: Mar. 28, 2002

(65) Prior Publication Data

US 2004/0033570 A1 Feb. 19, 2004

Related U.S. Application Data

(62) Division of application No. 09/215,694, filed on Dec. 18, 1998, now Pat. No. 6,391,583.

(51) Int. Cl.[7] .............................................. C12N 5/00
(52) U.S. Cl. .................... 435/325; 435/325; 435/252.3; 435/254.1; 435/254.11; 435/320.1; 435/69.1; 435/193; 435/6; 435/7.1; 530/350; 530/300
(58) Field of Search ............................. 435/325, 252.3, 435/254.11, 254.1, 320.1, 69.1, 193, 6, 7.1; 530/350, 300

(56) References Cited

U.S. PATENT DOCUMENTS

| | | | |
|---|---|---|---|
| 4,231,938 A | 11/1980 | Monaghan et al. | 260/343.5 |
| 4,282,155 A | 8/1981 | Smith et al. | 260/343.5 |
| 4,323,648 A | 4/1982 | Tanzawa et al. | 435/125 |
| 4,342,767 A | 8/1982 | Albers-Schonberg et al. | 424/250 |
| 4,346,227 A | 8/1982 | Terahara et al. | 560/119 |
| 4,444,784 A | 4/1984 | Hoffman et al. | 424/279 |
| 5,030,447 A | 7/1991 | Joshi et al. | 424/80 |
| 5,151,365 A | 9/1992 | Dombrowski et al. | 435/254 |
| 5,159,104 A | 10/1992 | Dabora et al. | 560/119 |
| 5,180,589 A | 1/1993 | Joshi et al. | 424/465 |
| 5,182,298 A | 1/1993 | Helms et al. | 514/455 |
| 5,198,345 A | 3/1993 | Gwynne et al. | 435/69.1 |
| 5,252,474 A | 10/1993 | Gewain et al. | 435/172.3 |
| 5,362,638 A | 11/1994 | Dahiya | 435/125 |
| 5,744,350 A * | 4/1998 | Vinci et al. | 435/254.11 |

FOREIGN PATENT DOCUMENTS

| | | |
|---|---|---|
| EP | 0 556 699 A1 | 8/1993 |
| WO | WO9512661 * | 5/1995 |

OTHER PUBLICATIONS

J.T. Kealey, et al., "Production of a Polyketide Natural Product in Nonpolyketide–producing Prokaryotic and Eurkaryotic Hosts," Proc. Natl. Acad. Sci. USA 95:505–509 1998.

J. Kennedy, et al., "Modulation of Polyketide Synthase Activity by Accessory Proteins During Lovastatin Biosynthesis," Science 284:1368–1372, 1999.

M. Manzoni, et al., "Production and Purification of Statins from *Aspergillus terreus* Strains," Botechnol. Tech. 12(7):529–532, 1998.

* cited by examiner

*Primary Examiner*—Jon Weber
*Assistant Examiner*—Hope A. Robinson
(74) *Attorney, Agent, or Firm*—Quarles & Brady LLP

(57) ABSTRACT

A method of increasing the production of lovastatin or monacolin J in a lovastatin-producing or non-lovastatin-producing organism is disclosed. In one embodiment, the method comprises the steps of transforming an organism with the *A. terreus* D4B segment, wherein the segment is translated and where an increase in lovastatin production occurs.

6 Claims, 6 Drawing Sheets

METHOD OF PRODUCING ANTIHYPERCHOLESTEROLEMIC AGENTS

CROSS-REFERENCES TO RELATED APPLICATION

This application is a divisional application of U.S. Ser. No. 09/215,694 filed Dec. 18, 1998 now U.S. Pat. No. 6,391,583.

STATEMENT REGARDING FEDERALLY SPONSORED RESEARCH AND DEVELOPMENT

This invention was made with United States government support awarded by the following agencies: NIH Grant No: AI43031. The United States has certain rights in this invention.

BACKGROUND OF THE INVENTION

Cholesterol and other lipids are transported in body fluids by low-density lipoproteins (LDL) and high-density lipoproteins (HDL). Substances that effectuate mechanisms for lowering LDL-cholesterol may serve as effective antihypercholesterolemic agents because LDL levels are positively correlated with the risk of coronary artery disease.

MEVACOR (lovastatin; mevinolin) and ZOCOR (simvastatin) are members of a group of active antihypercholesterolemic agents that function by inhibiting the rate-limiting step in cellular cholesterol biosynthesis, namely the conversion of hydroxymethylglutarylcoenzyme A (HMG-CoA) into mevalonate by HMG-CoA reductase.

The general biosynthetic pathway of a naturally occurring HMG-CoA reductase inhibitor has been outlined by Moore, et al., who showed that the biosynthesis of mevinolin (lovastatin) by *Aspergillus terreus* ATCC 20542 begins with acetate and proceeds via a polyketide pathway (R. N. Moore, et al., *J. Amer. Chem. Soc.* 107:3694–3701, 1985). Endo, et al. described similar biosynthetic pathways in *Pencillium citrinum* NRRL 8082 and *Monascus ruber* M-4681 (A. Y. Endo, et al., *J. Antibiot.* 38:444–448, 1985).

The recent commercial introduction of microbial HMG-CoA reductase inhibitors has fostered a need for high yielding production processes. Methods of improving process yield have included scaling up the process, improving the culture medium and simplifying the isolation.

Previous attempts to increase the biosynthesis of HMG-CoA reductase inhibitors at the level of gene expression have focused on increasing the concentration triol polyketide synthase (TPKS), a multifunctional protein with at least six activities as evidenced by the product of the enzymatic activity (Moore, supra, 1985). TPKS is believed to be the rate-limiting enzymatic activity(ies) in the biosynthesis of the HMG-CoA reductase inhibitor compounds.

U.S. Pat. No. 5,744,350 identifies a DNA encoding triol polyketide synthase (TPKS) from *Aspergillus terreus*. "NPKS" is now preferred to TPKS as the acronym for "nonaketide polyketide synthase."

SUMMARY OF THE INVENTION

In one embodiment, the present invention is a method of increasing the production of lovastatin in a lovastatin-producing organism. The method comprises the steps of transforming the organism with a nucleic acid sequence comprising the D4B segment, preferably comprising nucleotides 579–33,000 of SEQ ID NO:18 and 1–5,349 of SEQ ID NO:19. The nucleic acid sequence is transcribed and translated and an increase in lovastatin production occurs. Preferably, this increase is at least 2-fold.

In a preferred form of the present invention, the lovastatin-producing organism is selected from the group consisting *A. terreus* ATCC 20542 and ATCC 20541.

In another embodiment, the method comprises the step of transforming the organism with the corresponding D4B segment isolated from a non-*A. terreus* lovastatin-producing organism.

In another embodiment, the present invention is a method of increasing the production of lovastatin in a lovastatin-producing organism, comprising the step of transforming the organism with the LovE gene, wherein the nucleic acid sequence is transcribed and translated and wherein an increase in lovastatin production occurs.

In another embodiment of the present invention, one may increase the production of monacolin J in a non-lovastatin-producing organism comprising the steps of transforming the organism with a nucleic acid sequence comprising the D4B segment. As a further step, one may additionally transform the organism with an entire LovF gene. If the entire LovF gene is added to the D4B segment, the organism will produce lovastatin.

In another embodiment, the present invention is the lovastatin production gene cluster, preferably SEQ ID NOs: 18 and 19, and the individual genes comprising that cluster.

It is an object of the present invention to provide a method for increasing lovastatin and monacolin J production in both lovastatin-producing and non-lovastatin producing organisms.

Other objects, features and advantages of the present invention will become apparent after review of the specification, claims and drawings.

DESCRIPTION OF THE INVENTION

In General

Figure 1:
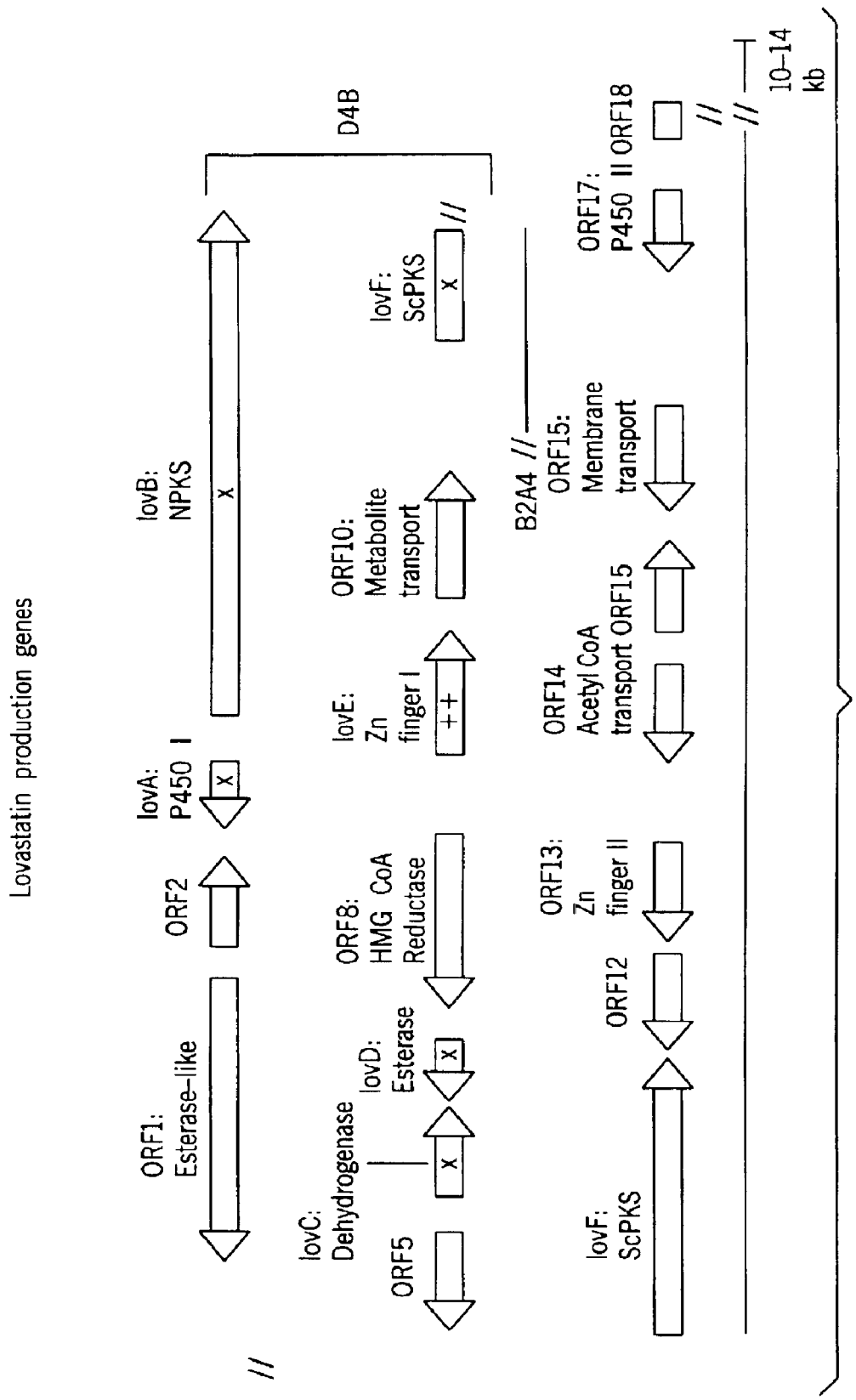
FIG. 1 is a diagram of lovastatin production genes.

The Examples below disclose the cloning and sequencing of a cluster of 17 genes from *A. terreus* ATCC 20542, a strain that natively produces lovastatin (See FIG. 1). These genes flank the NPKS gene, which is known to be required for lovastatin production (see, for example, U.S. Pat. No. 5,744,350).

The DNA sequence of the cluster has been determined and is disclosed below at SEQ ID NOs: 18 and 19. Mutations in four of the genes (P450I/LovA, SEQ ID NO:22; dehydrogenase/LovC, SEQ ID NO:24; esterase/LovD, SEQ ID NO: 25; and ScPKS/LovF, SEQ ID NO:29) have been isolated and demonstrate that each of these four individual genes is required for lovastatin production. These genes are indicated with an X symbol in FIG. 1 and referred to herein as the "*A. terreus* lovastatin gene cluster."

Another of the genes (Zn Finger I/LovE, SEQ ID NO: 27) is thought to regulate the transcription of the other genes and causes a notable increase in lovastatin production when reintroduced into *A. terreus* ATCC 20542.

Applicants have used the following convention in naming the genes and proteins of the present invention. The genes and proteins are first named with either an "ORF" or "Lov" prefix and then named either numerically or alphabetically. "Lov" signifies genes shown to be essential for lovastatin production. Applicants have also included a descriptor name that describes a probable function of the protein. For example, SEQ ID NO:1 is described as the "ORF1/esterase-like protein" because Applicants have compared the amino acid sequence to known esterases.

The portion of the gene cluster between ORF1/esterase-like protein and the mid-region of LovF/SCPKS is referred to as the "D4B segment". The *A. terreus* D4B segment is contained within a plasmid clone deposited as ATCC 98876. As described below, other lovastatin-producing organisms contain an analogous D4B segment comprising analogous genes. The present invention comprises a "D4B segment" isolated from other lovastatin-producing organisms. The arrangment of the genes within the D4B segment may be different in other organisms. We predict that the genes within these other segments will have at least 80% homology, at the nucleic acid level, with the genes disclosed herein. We envision that each of these lovastatin-producing organisms will comprise within their genomes a LovA, LovB, LovC, LovD, LovE and LovF gene.

We have determined that the D4B segment will confer production of monocolin J if the genes are all expressed, as we show below in an example using *A. nidulans*. We envision that adding the LovF gene to the D4B segment genes will result in the production of lovastatin in a non-lovastatin-producing organism.

Table 1, below, summarizes information regarding the different protein and nucleic acid sequences of the present invention. SEQ ID NOs: 1–17 are predicted translation products of various members of the gene cluster. SEQ ID NOs: 18 and 19 are the entire DNA sequence of the gene cluster. SEQ ID NOs: 21–36 are the genomic DNA sequences of the various members of the gene cluster and include the introns. These DNA sequences are reported in the Sequence Listing in the 5'–3' orientation, although, as FIG. 1 indicates, some of these DNA sequences are in the inverted orientation in the actual cluster.

TABLE 1

| SEQ ID NO. | DESCRIPTION | COMMENTS |
|---|---|---|
| SEQ ID NO: 1 | Predicted amino acid sequence of ORF1/Esterase-like protein | Translation of 6 EXONS 6865–6568, 6462–5584, 5520–4822, 4774–3511, 3332–2372, 2301–1813 (reverse complement) FROM SEQ ID NO: 18 |
| SEQ ID NO: 2 | Predicted amino acid sequence of ORF2 | Translation of 1 EXON 7616–8602 FROM SEQ ID NO: 18 |
| SEQ ID NO: 3 | Predicted amino acid sequence of LovA/P4501 protein | Translation of 1 EXON 10951–9980 (reverse complement) FROM SEQ ID NO: 18 |
| SEQ ID NO: 4 | Predicted amino acid sequence of ORF5 | Translation of 1 EXON 22760–21990 (reverse complement) FROM SEQ ID NO: 18 |
| SEQ ID NO: 5 | Predicted amino acid sequence of LovC/Dehydrogenase | Translation of 3 EXONS 23158–23717, 23801–23912, 23991–24410 FROM SEQ ID NO: 18 |
| SEQ ID NO: 6 | Predicted amino acid sequence of LovD/Esterase | Translation of 3 EXONS 26203–26080, 26005–25017, 24938–24810 (reverse complement) FROM SEQ ID NO: 18 |
| SEQ ID NO: 7 | Predicted amino acid sequence of ORF8/HMG CoA Reductase | Translation of 5 EXONS 30062–29882, 29803–29745, 29664–27119, 27035–26779, 26722–26559 (reverse complement) FROM SEQ ID NO: 18 |
| SEQ ID NO: 8 | Predicted amino acid sequence of LovE/Zn Finger I | Translation of 1 EXON 31360–32871 FROM SEQ ID NO: 18 |
| SEQ ID NO: 9 | Predicted amino acid sequence of ORF10/Metabolite transport | Translation of 8 EXONS 1400–1452, 1619–1695, 1770–1996, 2065–2088, 2154–2225, 2332–2865, 2939–3099, 3180–3560 FROM SEQ ID NO: 19 |
| SEQ ID NO: 10 | Predicted amino acid sequence of LovF/ScPKS | Translation of 7 EXONS 4430–4627, 4709–4795, 4870–4927, 4985–5318, 5405–5912, 5986–6565, 6631–12464 FROM SEQ ID NO: 19 |
| SEQ ID NO: 11 | Predicted amino acid sequence of ORF12 | Translation of 3 EXONS 13596–13496, 13451–13063, 12968–12709 (reverse complement) FROM SEQ ID NO: 19 |
| SEQ ID NO: 12 | Predicted amino acid sequence of ORF13/Zn Finger II | Translation of 5 EXONS 16608–16463, 16376–15572, 15519–15346, 15291–14825, 14767–14131 (reverse complement) FROM SEQ ID NO: 19 |

TABLE 1-continued

| SEQ ID NO. | DESCRIPTION | COMMENTS |
| --- | --- | --- |
| SEQ ID NO: 13 | Predicted amino acid sequence of ORF14/Acetyl CoA transport protein | Translation of 7 EXONS 19642–19571, 19502–19427, 19352–19227, 19158–19011, 18956–18663, 18587–18438, 18380–18341 (reverse complement) FROM SEQ ID NO: 19 |
| SEQ ID NO: 14 | Predicted amino acid sequence of ORF15 | Translation of 2 EXONS 20332–20574, 20631–21860 FROM SEQ ID NO: 19 |
| SEQ ID NO: 15 | Predicted amino acid sequence of ORF16/Membrane transport protein | Translation of 5 EXONS 24521–24054, 23996–23936, 23876–23184, 23111–22977, 22924–22818 (reverse complement) FROM SEQ ID NO: 19 |
| SEQ ID NO: 16 | Predicted amino acid sequence of ORF17/P450II protein | Translation of 3 EXONS 28525–27673, 27606–27284, 27211–26837 (reverse complement) FROM SEQ ID NO: 19 |
| SEQ ID NO: 17 | Predicted amino acid sequence of ORF18 (incomplete) | Translation of 2 EXONS 29826–30995, 31054–31328 (incomplete) FROM SEQ ID NO: 19 |
| SEQ ID NO: 18 | DNA sequence of gene cluster-first 33,000 nucleotides | |
| SEQ ID NO: 19 | DNA sequence of cluster-nucleotides 33,001–64,328 (renumbered 1–31,328) | |
| SEQ ID NO: 20 | DNA sequence of ORF1/Esterase-like gene | Start = 6865 Stop = 1813 SEQ ID NO: 18 |
| SEQ ID NO: 21 | DNA sequence of ORF2 | Start = 7616 Stop = 8602 SEQ ID NO: 18 |
| SEQ ID NO: 22 | DNA sequence of LovA/P450I gene | Start = 10951 Stop = 9980 SEQ ID NO: 18 |
| SEQ ID NO: 23 | DNA sequence of ORF5 | Start = 22760 Stop = 21990 SEQ ID NO: 18 |
| SEQ ID NO: 24 | DNA sequence of LovC/Dehydrogenese | Start = 23158 Stop = 24410 SEQ ID NO: 18 |
| SEQ ID NO: 25 | DNA sequence of LovD/Esterase | Start = 24810 Stop = 26203 SEQ ID NO: 18 |
| SEQ ID NO: 26 | DNA sequence of ORF8/HMG CoA Reductase | Start = 30062 Stop = 26559 SEQ ID NO: 18 |
| SEQ ID NO: 27 | DNA sequence of LovE/Zn Finger I | Start = 31360 Stop = 32871 SEQ ID NO: 18 |
| SEQ ID NO: 28 | DNA sequence of ORF10/Metabolite transport | Start = 1400 Stop = 3560 SEQ ID NO: 19 |
| SEQ ID NO: 29 | DNA sequence of LovF/ScPKS | Start = 4430 Stop = 12464 SEQ ID NO: 19 |
| SEQ ID NO: 30 | DNA sequence of ORF12 | Start = 13596 Stop = 12709 SEQ ID NO: 19 |
| SEQ ID NO: 31 | DNA sequence of ORF13/Zn Finger II | Start = 16608 Stop = 14131 SEQ ID NO: 19 |
| SEQ ID NO: 32 | DNA sequence of ORF14/Acetyl CoA transport gene | Start = 19642 Stop = 18341 SEQ ID NO: 19 |
| SEQ ID NO: 33 | DNA sequence of ORF15 | Start = 20332 Stop = 21860 SEQ ID NO: 19 |
| SEQ ID NO: 34 | DNA sequence of ORF16/Membrane transport protein | Start = 24521 Stop = 22818 SEQ ID NO: 19 |
| SEQ ID NO: 35 | DNA sequence of ORF17/P450II gene | Start = 28525 Stop = 26837 SEQ ID NO: 19 |

TABLE 1-continued

| SEQ ID NO. | DESCRIPTION | COMMENTS |
|---|---|---|
| SEQ ID NO: 36 | DNA sequence of ORF18 (incomplete) | Start = 29826 to 31328 (incomplete) SEQ ID NO: 19 |

Table 1 also notes the translation start and stop points in the various gene sequences.

The sequence of the NPKS gene is not listed in SEQ ID NOs: 21–36. This gene is characterized in U.S. Pat. No. 5,744,350. However, SEQ ID NOs: 18 and 19 do contain the sequence of the NPKS gene within the context of the entire gene cluster.

To perform many embodiments of the present invention, one will need to recreate various genes or a portion of the gene cluster described herein. Applicants have provided sequence data in the Sequence Listing sufficient to allow one of skill in the art to construct numerous probes suitable to recreate the genes from an *A. terreus* genomic library. Applicants have also described below various methods for isolating *A. terreus* DNA.

Figure 4:
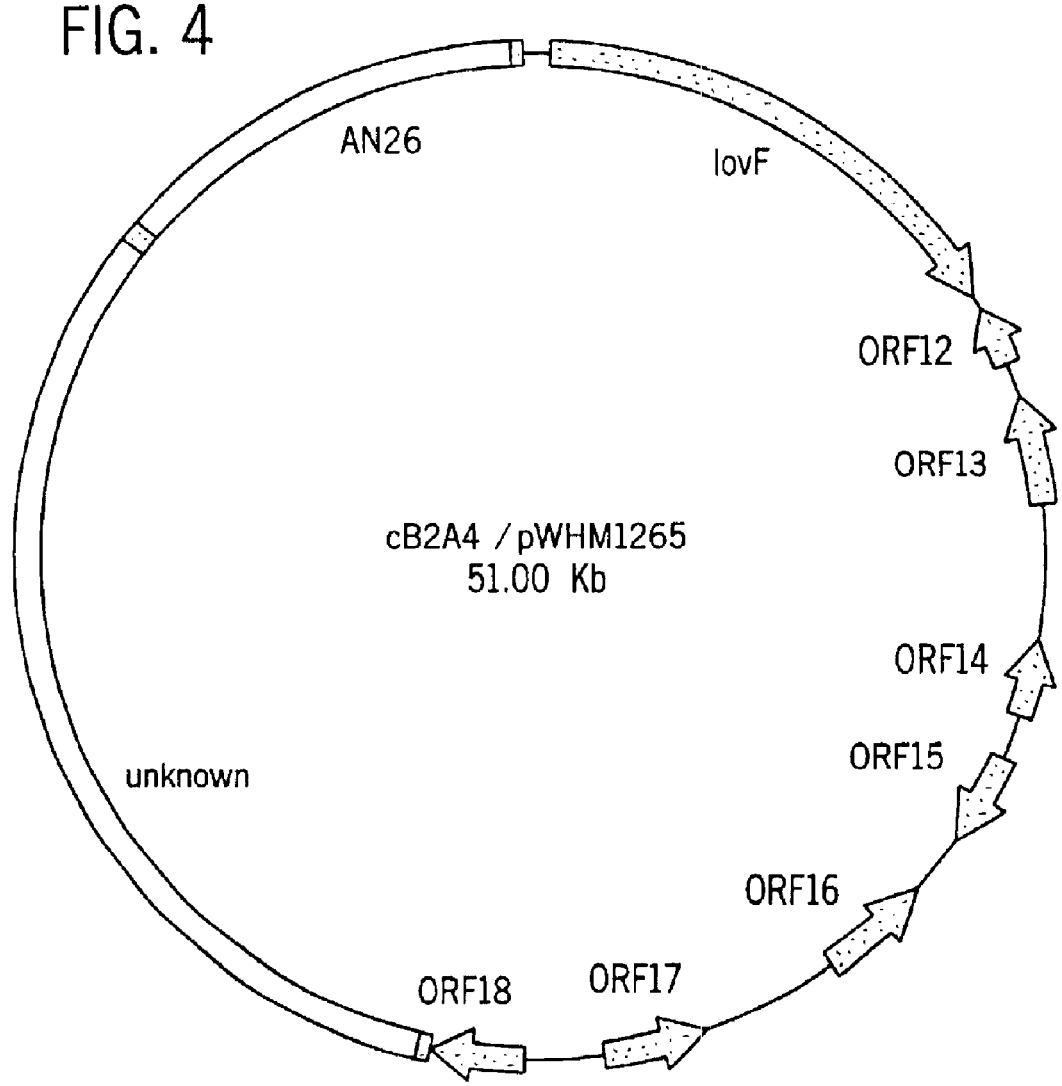
FIG. 4 is a schematic drawing of plasmid pWHM1264/CB24A.

Additionally, Applicants have deposited ATCC Accession No. ATCC 98876, which contains clone pWHM1263 (cD4B) and ATCC Accession No. ATCC 98877 which contains clone pWHM1265 (CB2A4). This deposit is under the terms and conditions of the Budapest Treaty. These deposits were made on Sep. 10, 1998 at the American Type Culture Collection, Manassas, Va. 20110-2209, Both plasmids are described in more detail below. FIG. 4 describes clone CB2A4/pWHM1265, and FIG. 6 describes clone CB4B/pWHM1263. FIG. 1 also indicates the boundaries of the D4B and B2A4 clones.

The clones and their inserts may be prepared from the ATCC deposits by methods known to those of skill in the art. The DNA from the clones may be isolated and any gene within the gene cluster may be isolated and utilized.

Increasing the Production of Lovastatin by Lovastatin-Producing Fungi and Yeast In one embodiment, the present invention is a method of increasing the production of lovastatin in a lovastatin-producing fungi and yeast, preferably *A. terreus* ATCC20542 and ATCC20541. Other examples of suitable lovastatin-producing fungi and yeast are listed in Table 2, below.

TABLE 2

Microorganisms other than *A. terreus* reported to produce lovastatin (mevinolin)

Monascus (17 of 124 strains screened) species[1]
M. ruber
M. purpureus
M. pilosus
M. vitreus
M. pubigerus
Penicillium sp.[1]
Hypomyces sp.
Doratomyces sp.
Phoma sp.
Eupenicillium sp.
Gymnoascus sp.
Trichoderma sp.
Pichia labacensis[2]
Candida cariosilognicola
Aspergilus oryzea[3]
Doratomyces stemonitis

TABLE 2-continued

Microorganisms other than *A. terreus* reported to produce lovastatin (mevinolin)

Paecilomyces virioti
Penicillium citrinum
Penicillin chrysogenum
Scopulariopsis brevicaulis
Trichoderma viride

[1]P. Juzlova, L. Martinkova, V. Kren. Secondary Metabolites of the fungus Monascus: a J. Ind. Microbiol. 16: 163–170 and references cited therein (1996).
[2]N. Gunde-Cimerman, A. Plemenitas and A. Cimerman. A hydroxymethylglutaryl-CoA inhibitor synthesized by yeasts. FEMS Microbiol. Lett. 132: 39–43 (1995).
[3]A. A. Shindia. Mevinolin production by some fungi. Folio Microbiol. 42: 477–480 (1997

By "increasing the production" we mean that the amount of lovastatin produced is increased by at least 2-fold, preferably by at least 5-fold. The examples below demonstrate two preferred methods for analyzing strains for lovastatin production. In method A, the spore suspension is inoculated into a flask of SEED medium and grown. The resulting seed culture is used to inoculate FM media and grown for six days. In fermentation method B, one inoculates 50 ml of RPM media and grows this larger culture for 7 days.

Both cultures are extracted, pH adjusted, mixed with ethyl acetate and shaken for two hours. For analysis, 1 ml of the ethyl acetate layer is dried under a nitrogen stream and resuspended in methanol. For TLC analysis, a small amount of the extract is run on C18 reverse phase TLC plates in a solvent system of methanol; 0.1% phosphoric acid. The TLC plates are developed by spraying with phosphomolybdic acid in methanol and heating with a heat gun. The extracts are compared with authentic lovastatin, monacolin J, monacolin L and dihydromonocolon L.

If one wishes HPLC analysis, the examples below describe the use of a Waters NOVA-PAK C18 column used with a solvent system of acetonitrile and phosphoric acid. A Waters 996 Photodiode Array Detector will detect the metabolites. Lovastatin was detected at 238 nm.

In one embodiment, one would transform a lovastatin-producing fungi or yeast with the lovE/zinc finger I gene, preferably comprising the nucleotides of SEQ ID NO: 27. The examples below predict that this will result in an increase of at least 5–7 fold. Preferably, the increase will be at least 2.0-fold.

One may also transform a lovastatin-producing fungi or yeast with the LovE gene isolated from other lovastatin-producing fungi or yeast. One may obtain this gene by use of a probe derived from SEQ ID NO:27 by methods known to those of skill in the art.

One may also transform lovastatin-producing fungi and yeast with the D4B segment of the lovastatin production gene cluster (see FIG. 1), preferably as found in ATCC accession number 98876. Alternatively, one may transform lovastatin-producing fungi or yeast with the entire gene cluster, as diagramed in FIG. 1.

We envision that to successfully increase lovastatin production, one may also wish to transform less than the entire gene cluster. Preferably, one may determine what the smallest possible segment is by deleting various portions of the gene cluster and determining whether lovastatin production is continually increased. Similarly, if one begins with the D4B segment, one may delete various portions for the segment and determine whether lovastatin production is continually increased by at least 2-fold.

Figure 3:
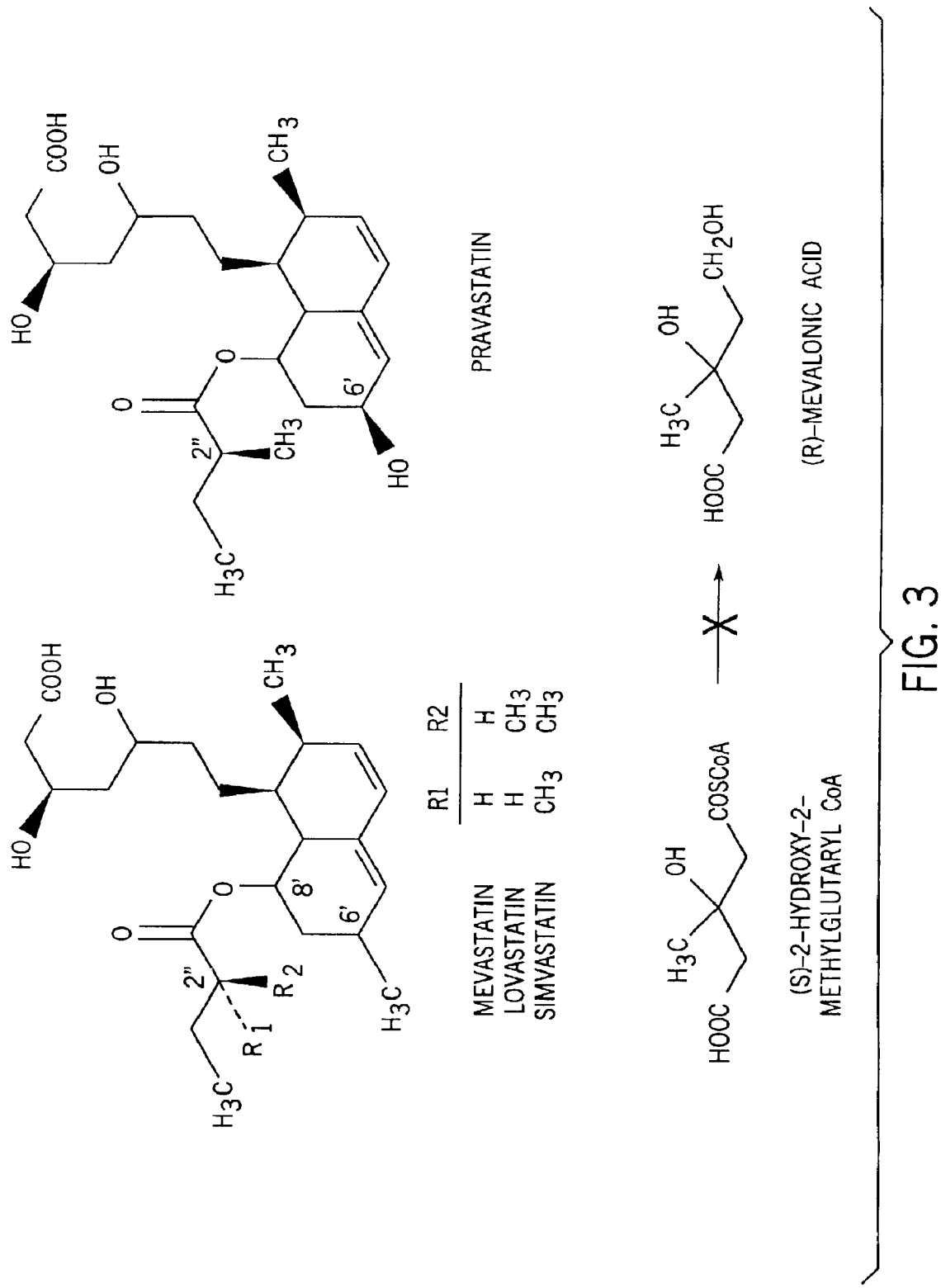
FIG. 3 is a comparative diagram of statins.

Modification of the LovB/NPKS gene would produce other HMG CoA inhibitors. For example, FIG. 3 diagrams the relationship between mevastatin, lovastatin, simvastatin and pravastatin. In one example, the methyl transferase domain of the NPKS gene may be replaced with an inactive form to make pravastatin. The HMG-CoA reductase inhibitors within this invention include, but are not limited to, compactin (ML-236B), lovastatin, simvastatin, pravastatin and mevastatin.

In another embodiment of the present invention, one may transform a lovastatin-producing organism with the genes described above and obtain the production of an HMG CoA reductase inhibitor with a structure different from monacolin J. monacolin L or lovastatin. Alterations in the side chain attached to C8 are the most likely possibility but other alterations may occur. These alterations would happen through the native biochemistry of the organism.

If one wishes to express the A. terreus genes in yeast, one may wish to consult examples in which others have engineered fungal secondary metabolism genes for expression in yeast. (See for example, J. T. Kealey, et al., *Proc. Natl. Acad. Sci. USA* 95:505–509 (1998)). The exact approach could be used with the NPKS (LovB) and ScpKS (LovF) genes, and a somewhat simpler approach with the other lovastatin genes in their cDNA forms.

Production of HMG-CoA Reductase Inhibitors by Fungi and Yeast that do not Natively Produce Inhibitors.

In another embodiment, the present invention is the production of HMG-CoA reductase inhibitors, such as lovastatin, by fungi and yeast that do not natively produce lovastatin. An example of a suitable fungi or yeast is *A. nidulans* and *S. cerevisiae*, respectively.

Figure 2:
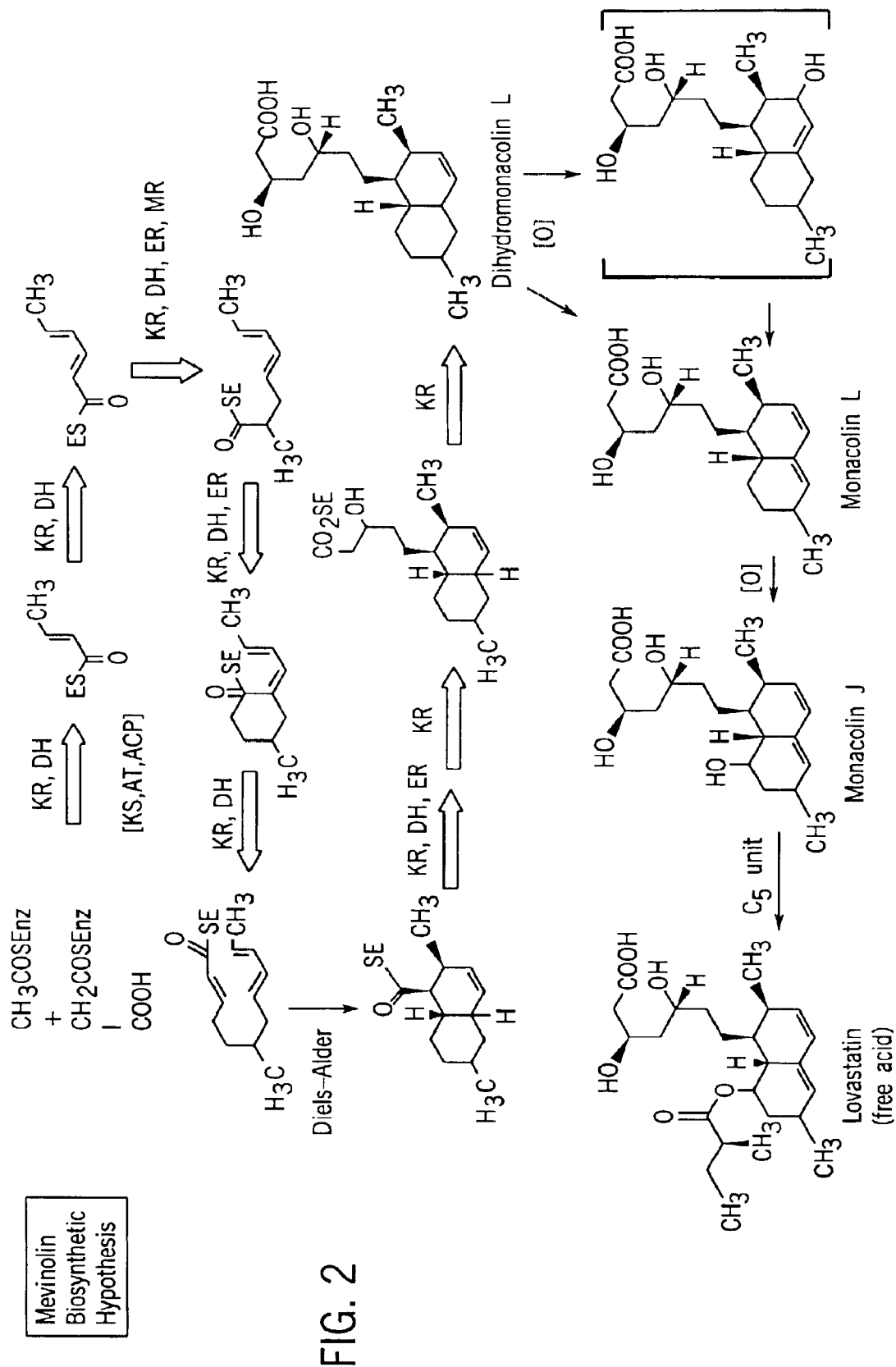
FIG. 2 is a schematic diagram of a hypothetical mevinolin/lovastatin biosynthesis pathway.

For this embodiment one preferably transforms the genes within the D4B segment into the non-inhibitor-producing strain. By this method, one would produce monacolin J (See FIG. 2) which could be chemically converted to lovastatin by one of skill in the art.

Monacolin J, in its lactone form obtained by treatment with anhydrous acid under dehydrative conditions, is preferably treated with a derivative of (2S)-2-methybutyric acid, in which the carboxyl group has been suitable activated for undergoing esterification, and the resulting lovastatin is isolated by conventional methods. For example, see WO 33538, U.S. Pat. No. 4,444,784 and *J. Med. Chem.* 29:849 (1986). These are citations for synthesis of simvastatin from monacolin J. One would use the same method, but use the (2S)-2-methylbutyrate derivative to make lovastatin.

In another embodiment of the present invention, one would transform the genes within the D4B segment, including an entire LovF/SCPKS gene, into the non-inhibitor-producing organism. By this method, one would produce lovastatin in a non-lovastatin-producing organism.

In another embodiment of the present invention, one may transform a non-lovastatin-producing organism with the genes described above and obtain the production of an HMG CoA reductase inhibitor with a structure different from monacolin J, monacolin L or lovastatin, as described above.

Modification of the LovB/NPKS gene would produce other inhibitors. For example, FIG. 3 diagrams the relationship between mevastatin, lovastatin, simvastatin and pravastatin. In one example, the methyl transferase domain of the NPKS gene may be replaced with an inactive form to make pravastatin. The HMG-CoA reductase inhibitors within this invention include, but are not limited to, compactin (ML-236B), lovastatin, simvastatin, pravastatin and mevastatin.

Production of Intermediate Materials

In another embodiment, the present invention is a method of isolating intermediate materials in the production of lovastatin and analogs such as mevastatin and simvastatin. For example, the Examples below demonstrate the disruption of the lovastatin projection gene cluster with mutagenized LovC, LovD, LovF, LovA or LovB genes. Disruption of many of these genetic elements of the lovastatin production gene cluster will result in accumulation of intermediate materials. Therefore, to practice this embodiment of the present invention, one would transform a suitable lovastatin-producing host with a mutagenized gene within the D4B segment, as described below.

Many other mutations would be suitable to destroy the function of LovC, LovD, LovF, LovA or LovB. All that is necessary is these genes be disrupted to the extent that they are non-functional.

Production of Lovastatin Analogs

In another embodiment, the present invention provides a method for engineering the production of lovastatin analogs in such organisms as fungi or yeast, using monacolin J as the starting point.

Isolated DNA Segments

In another embodiment, the present invention is a DNA segment capable of conferring lovastatin or monacolin J production or increase in lovastatin or monacolin J production in yeast or fungi. In a preferred example, this segment is the "D4B segment" that is deposited at ATCC 98876. The nucleotide sequence of this segment is found in residues 579–33,000 of SEQ ID NO:18 and residues 1–5,349 of SEQ ID NO:19.

In another embodiment, the present invention is the entire *A. terreus* lovastatin gene cluster, as exemplified by SEQ ID NOs: 18 and 19 and ATCC deposits 98876 and 98877.

The present invention is also the individual genes that make up the *A. terreus* lovastatin gene cluster. Therefore, the present invention is a nucleic acid segment selected from the group of consisting of SEQ ID NOs: 20–36. Preferably, the present invention is the coding region found within SEQ ID NOs: 20–36 and described in Table 1. The present invention is also a mutagenized version of SEQ ID NOs: 22, 24, 25 and 29, wherein the gene is mutagenized to be non-functional in terms of lovastatin or monacolin J production.

Organisms with Increased Lovastatin or Monacolin J Production

In another embodiment, the present invention are the organisms described above. These organisms include lovastatin-producing organisms, preferably yeast and fungi, that have been engineered to display at least a 2-fold increase in lovastatin or monacolin J production. The organisms also include non-lovastatin-producing organisms, preferably yeast or fungi, that have been engineered to produce monacolin J or lovastatin.

Antifungal Compounds

Applicants note that lovastatin, monocolin J, monocolin L and dihydromonocolin L all have varying degrees of antifungal activity. Applicants envision that the present invention is also useful for providing antifungal compounds and organisms engineered to express antifungal compounds. Preferably, one would measure the antifungal properties of a compound in the manner of N. Lomovskaya, et al., *Microbiology* 143:875–883, 1997. Measurement of inhibition of yeast growth can be found in R. Ikeura, et al., *J. Antibiotics* 41:1148, 1988. The same general methods could be used for all fungi. Both of these references are hereby incorporated by reference.

EXAMPLES

1. General Methods and Procedures
Construction of an *A. terreus* ATCC20542 Genomic Library.

*A. terreus* ATCC20542 genomic DNA was partially digested with Sau3AI so as to produce an average fragment size of 40–50 kb. The partially digested genomic DNA was then separated on a sucrose gradient and the 40–50 kb fraction was collected. Cosmid AN26 (Taylor and Borgmann, *Fungal Genet. Newsletter* 43, 1996) was prepared by digestion with ClaI, dephosphorylated with CIP, then digested with BamHI to create the two cosmid arms. Ligation reactions with genomic DNA fragments and cosmid arms were optimized and packaged using Gigapack III XL packaging extract (Stratagene). The packaged cosmid library was infected into *E. coli* JM109 and plated out onto LB agar (Sambrook, et al., *Molecular Cloning. A Laboratory Manual.* 2nd ed. Cold Spring Harbour Laboratory Press, 1989; other standard methods used can be found here also) with ampicillin (50 µg/ml) plates. After checking for the presence of insert DNA in a selection of clones, 5000 colonies were picked into LB plus 50 µg/ml ampicillin filled microtitre plates and grown overnight at 37° C. The colonies were replica plated onto nylon membranes (Amersham HYBOND-N). Glycerol was added at a final concentration of 15% (v/v) to the microtitre plates and these were stored at −70° C.

Isolation of Genomic Clones Containing the Lovastatin Biosynthesis Cluster.

A 2.8 kb EcoRI fragment from pTPKS100 containing part of the NPKS gene (Vinci, et al., U.S. Pat. No. 5,744,350) was gel-isolated and labelled with digoxigenin using the GENIUS KIT II (Boehringer Mannheim). This labelled fragment was hybridized (65° C., 5×SSC) with the nylon membranes containing the *A. terreus* genomic library, then washed (65° C, 0.1×SSC). Two positive clones were identified, pWHM1263 (cD4B) and pWHM1264 (cJ3A). Two of these clones, pWHM1263 (cD4B) and pWHM1265 (cB2A4), have been deposited in the ATCC (American Type Culture Collection, 10801 University Boulevard, Menassas, Va. 20110) at accession number ATCC 98876 and 98877, respectively, under the terms and conditions of the Budapest Treaty. The presence of the NPKS gene was confirmed initially by restriction digestion and later by DNA sequencing.

Overlapping clones were found by repeating the hybridization process using labelled fragments from both ends of the insert in pWHM1263. This resulted in the isolation of pWHM1265–1270 (cB2A4, cL3E2, cJ3B5, cO2B5, cR3B2, cW3B1) from downstream of the NPKS gene and pWHM1271 (cQ1F1) from upstream of NPKS. All these clones were transformed into *E. coli* strain STBL2 (Stratagene) to help prevent rearrangements.

Figure 6:
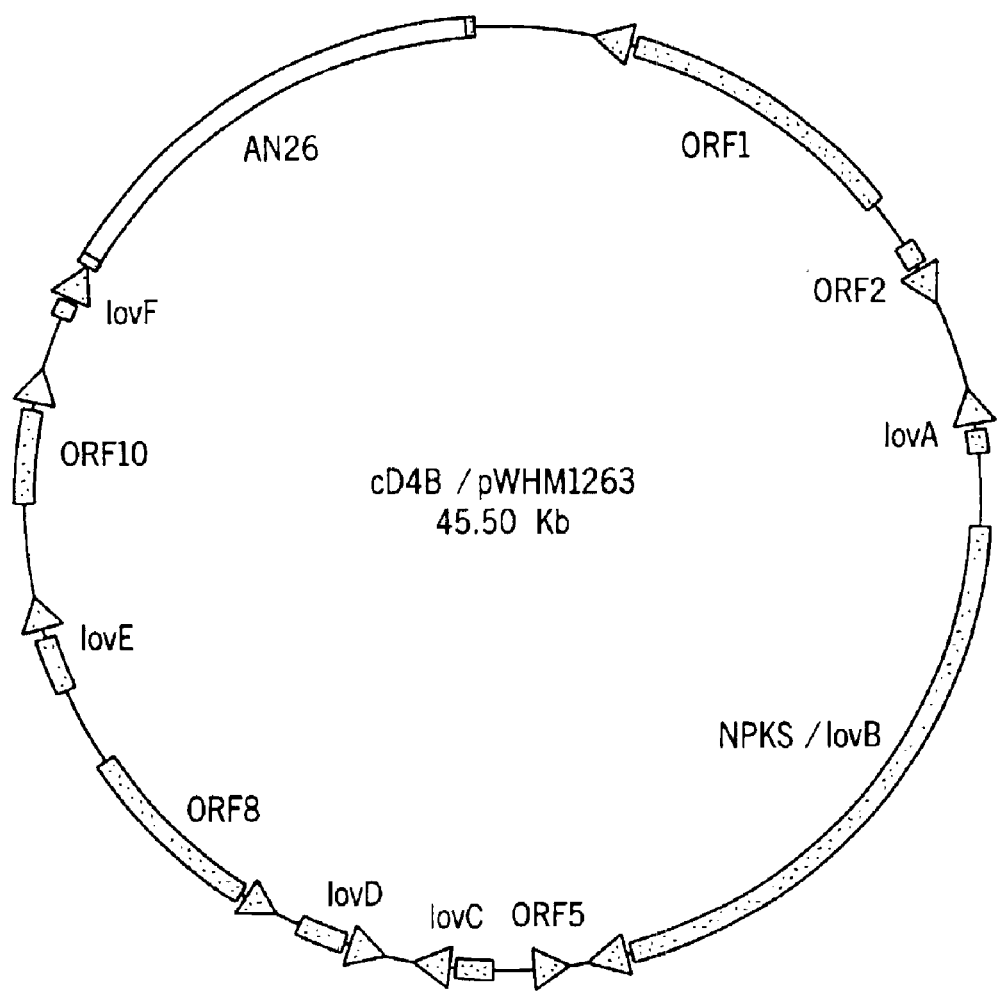
FIG. 6 is a schematic drawing of plasmid CD4B/pWHM1263.

FIG. 4 is a diagram of the cB2A4/pWHM1265 clone. This clone contains an insert of approximately 43 kb in AN26 and includes the nucleotide sequence from at least nucleotides 4988 of SEQ ID NO:19 to nucleotide 31,328 of SEQ ID NO:19 and 10–14 kb of uncharacterized DNA. FIG. 6 is a schematic diagram of cD4B/pWHM1263. This clone contains a 37,770 bp insert in AN26 and contains nucleotides 579–33,000 of SEQ ID NO:18 and nucleotides 1–5,349 of SEQ ID NO:19.

Sequencing Strategy and Analysis.

A series of overlapping subclones (pWHM1272-pWHM1415) were constructed in pSPORT1 (Gibco-BRL) and pGEM3 (Promega). Plasmid DNAs for sequencing were prepared using the QiaPrep SPIN MINIPREP KIT (Qiagen). Cycle sequencing was carried out using the AmpliTaq FS or BigDye reagents (ABI) and were analyzed using a ABI model 373 or 377 DNA Sequencer. Primer walking was performed by synthesis of 18–22 bp oligonucleotide primers based on the sequenced DNA strand, with the help of the Oligo 4.05 program (National Biosciences, Inc.). Every region of DNA was sequenced at least once on both strands. Direct sequencing of cosmids and PCR products was used to confirm adjoining regions where no overlapping clones existed. DNA sequence analysis and manipulations were performed using SEQMAN (DNASTAR) and SEQED (ABI) software. Assignments of putative ORFS, including putative introns, were performed with the aid of BLAST 2.0 searches (Atschul, et al., *Nucl. Acids Res.* 25:3389–3402, 1997), and the Genetics Computer Group (GCG) programs (Program Manual for the Wisconsin Package, Version 8, September 1994, Genetics Computer Group, Madison, Wis.), version 8.1.

Isolation and Characterization of lovF (ScPKS, ORF11), lovD (EST1, ORF7), lovC (DH, ORF6), and lovA (P450I, ORF3) Mutants.

lovF

To disrupt the polyketide synthase gene, lovF, a 1.7 kb EcoRI fragment internal to the lovF gene was subcloned from pWHM1265 into pSPORT1 to give pWHM1291. The ScPKS fragment was then subcloned from this vector, as an Acc65I—HindIII fragment, into pPLOA (Vinci, et al., U.S. Pat. No. 5,744,350) to give pWHM1416. This vector contains the phleomycin (Zeocin, obtained from InVitrogen) resistance gene for selection in *A. terreus*. *A. terreus* ATCC20542 was then transformed to Zeocin resistance with this plasmid as described below. Transformants were screened for lovastatin production as described below (Method A). In one of the transformants, WMH1731, lovastatin production was abolished and a new compound accumulated. This new compound comigrated with monacolin J on TLC and HPLC according to the methods described below. Semi-preparative HPLC was used to partially purify the major product which was then analyzed by HPLC—MS. The same mass and fragmentation pattern as authentic monacolin J was observed. To confirm the disruption of the lovF gene, total genomic DNA was prepared from wild-type *A. terreus* ATCC20542 and the WMH1731 mutant strain. The genomic DNA was digested with BamHI and HindIII, electrophoresed on an agarose gel and capillary blotted onto a nylon membrane. The membrane was hybridized with the 1.7 kb EcoRI fragment from pWHM1416 labelled using the Genius II kit (Boehringer Mannheim) using the conditions described previously. The wild-type strain had hybridizing bands at 4.2 kb for BamHI and 11.5 kb for HindIII. As predicted, the WMH1731 mutant strain had hybridizing bands at 6.5 kb and 2.2 kb for DamHI and 11 kb and 7.8 kb for HindIII confirming the homologous integration of a single copy of pWHM1416 at the lovF locus.

lovD

To disrupt the putative esterase/carboxypeptidase-like gene, lovD, a 4.8 kb NotI—EcoRI fragment from pWHM1263 was subcloned into pSPORTI to give pWHM1274. This plasmid was digested with HindIII and BsiWI and a 1.8 kb fragment was isolated. The plasmid was also digested with HindIII and BamHI and the 6.6 kb fragment was isolated. pPLOA was digested with BamHI and Acc65I and the 2.1 kb fragment containing the phleomycin resistance marker was purified. These three fragments were ligated together and used to transform competent *E.* coli cells. The expected plasmid, pWHM1417, containing the phleomycin resistance gene flanked by the beginning and the end of the lovD gene was isolated. This plasmid was linearized by digestion with XbaI or RsrII before being used to transform A. terreus ATCC20542 to Zeocin resistance. Transformants were screened for lovastatin production as described below (Method A). In one of the transformants, WMH1732, lovastatin production was abolished and a new compound accumulated. This new compound comigrated with monacolin J on TLC and HPLC according to the methods described below. Semi-preparative HPLC was used to partially purify the major product which was then analyzed by HPLC—MS. The same mass and fragmentation pattern as authentic monacolin J was observed. To confirm the disruption of the lovD gene, total genomic DNA was prepared from wild type A. terreus ATCC20542 and the WMH1732 mutant strain. The genomic DNA was digested with ApaI, run out on an agarose gel and capillary blotted onto a nylon membrane. The membrane was hybridized with the 4.8 kb NotI—EcoRI fragment from pWHM1274 labelled using the Genius II kit using the conditions described previously. The wild-type strain had hybridizing bands at 9 kb, 8.4 kb and 1.5 kb. As predicted the mutant strain had hybridizing bands at 9 kb, 8 kb, 3 kb and 1.5 kb confirming the homologous integration of a single copy of pWHM1417 at the lovD locus.

lovA

To disrupt the cytochrome P450 I gene, lovA, an 11 kb Acc65I—EcoRI fragment from pWHM1263 was subcloned into pGEM3 to give pWHM1272. From this plasmid a 2.1 kb ApaI—SnaBI fragment was purified and ligated to ApaI—EcoRV digested pPLOA to give p450Phleo (pWHM1418). From this plasmid a 4.2 kb ApaI—NotI fragment was purified and ligated with a 1.8 kb EagI—KpnI fragment from pWHM1272 and ApaI—KpnI digested pGEM7 to give p45ODphleo (pWHM1419) which contains the lovA gene disrupted by the phleomycin resistance gene. This plasmid was then digested with KpnI and ApaI and the resulting fragment was used to transform A. terreus ATCC20542 to Zeocin resistance. Transformants were screened for lovastatin production as described below (Method A). In one of the transformants, WMH1733, lovastatin production was abolished and two new compounds accumulated. Genomic DNA was prepared from this strain and from A. terreus ATCC20542, digested with EagI, run out on an agarose gel, and capillary blotted onto a nylon membrane. The membrane was hybridized with the 6 kb ApaI—KpnI fragment from pWHM1419 labelled using the Genius II kit using the conditions described previously. The wild-type strain had hybridizing bands at 2.0 kb, 1.9 kb and 1.1 kb. Mutant strain WMH1733 had hybridizing bands at 2.5 kb, 2.0 kb, 1.1 kb and 0.7 kb confirming the homologous integration of a single copy of the fragment from pWHM1419 at the lovA locus.

lovC

To disrupt the dehydrogenase-like gene, lovC, a 2 kb EcoRI—BglII fragment from pTPKS100 was ligated with a 1.7 kb EcoRI—SacI fragment from pWHM1274 and BglII—SacI digested litmus 28 (New England Biolabs) to produce pDH1 (pWHM1420). Another plasmid pDH2 (pWHM1421) was constructed from a 2.2 kb Acc65I—SacI fragment from pWHM1274, a 2.1 kb HindIII—SacI fragment from pPLOA containing the phleomycin resistance gene and HindIII—Acc65I digested litmus 28. The disruption vector pDH-dis (pWHM1422) was constructed by ligating together a 2.5 kb BglII—HpaI fragment from pWHM1420, a 4.3 kb EcoRV—KpnI fragment from pWHM1421 and BglII—KpnI digested litmus 28. This plasmid was digested with BglII and KpnI and the resulting 6.8 kb fragment was used to transform A. terreus ATCC20542 to Zeocin resistance. Transformants were screened for lovastatin production as described below (Method A). In two of the transformants, WMH1734 and WMH1735, lovastatin production was abolished. Genomic DNA was prepared from these strains and from A. terreus ATCC20542, digested with EagI, run out on an agarose gel, and capillary blotted onto a nylon membrane. The membrane was hybridized with the 6.8 kb BglII—KpnI fragment from pWHM1422 labelled using the Genius II kit using the conditions described previously. The wild type strain had hybridizing bands at 5 kb, 1.5 kb and 1.3 kb. Mutant strain WMH1734 had hybridizing bands at 4.9 kb, 1.3 kb, 1.0 kb and 0.7 kb confirming the homologous integration of a single copy of the fragment from pWHM1422 at the lovC locus. The other mutant strain, WMH1735, had a similar banding pattern but with additional hybridizing bands indicating that multiple integration events had occurred, one of which was at the lovC locus.

Construction and Characterization of the A. terreus Strain with Extra Copies of lovE.

Figure 5:
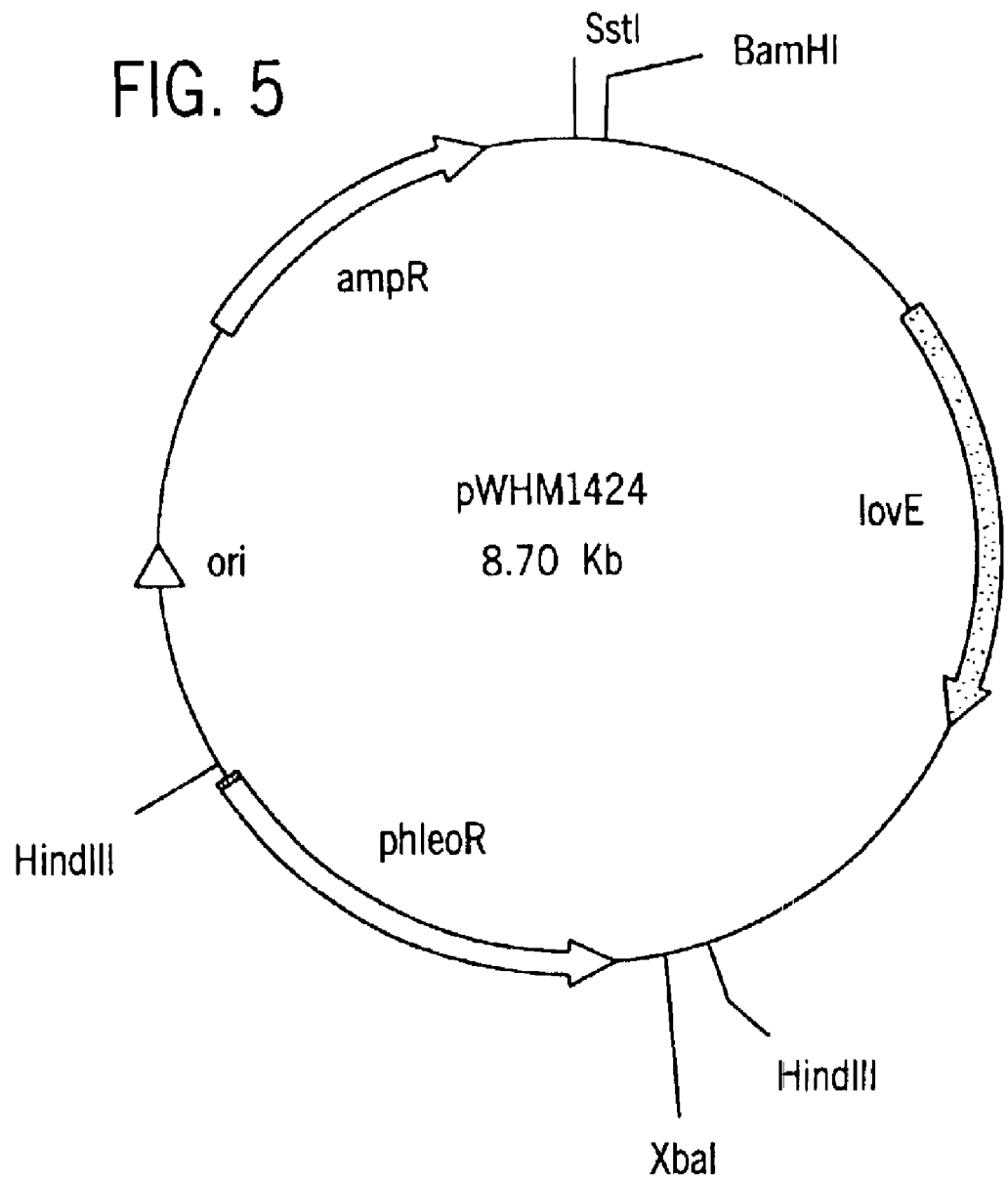
FIG. 5 is a schematic drawing of plasmid pWHM1424.

A 10.4 kb NotI—EcoRI fragment containing the putative regulatory gene, lovE was subcloned from pWHM1263 to pSPORT1 to give pWHM1276. From this plasmid a 3.9 kb HindIII—BamHI fragment was subcloned into pGEM7 to give pWHM1423. The regulatory gene was subcloned from this vector into pPLOA as an SstI—XbaRI fragment to give pWHM1424 (FIG. 5). pWHM1424 contains nucleotides 30,055–33,000 from SEQ ID NO:18 and nucleotides 1–1,026 from SEQ ID NO:19.

Extra copies of the regulatory gene were introduced into A. terreus ATCC20542 by transformation to Zeocin resistance with pWHM1424. Transformants were fermented (method A) and screened for lovastatin production initially by TLC analysis. Most of the transformants appeared to be producing significantly more lovastatin than the wild-type strain. The yields of lovastatin from the two transformant strains, WMH1736 and WMH1737, which had the most elevated levels compared to the wild-type was quantified by HPLC as described below. These were found to produce 7-fold and 5-fold more lovastatin than the A. terreus ATCC20542 strain.

Because of the way that the DNA integrates (ectopically), each transformant is or can be unique, genotypically and phenotypically. However, some will be overproducers; others may exhibit no difference, for unknown reasons.

Heterologous Expression of the Lovastatin Biosynthesis Genes.

To place the NPKS gene (lovB) under the control of the inducible alcA promoter, the 11.5 kb KpnI—AvrII fragment from pTPKS100 containing the NPKS open reading frame was ligated into pAL3 (Waring, et al., Gene 79:119, 1989) previously digested with KpnI and XbaI. The resulting plasmid was designated pAL3TPKS (WHM1425). The polymerase chain reaction was used to amplify the NPKS gene sequence between the NPKS promoter region just upstream of the translational start codon and a AgeI site internal to NPKS. The design of the forward primer introduced a KpnI site 31 bases from the translational start codon allowing the NPKS to be placed against the alcA promoter but also incorporating upstream elements from the A. terreus system. Amplification was performed using Vent DNA polymerase with pTPKS100 as template and 1 µmol of each primer in a final volume of 100 µl using the manufacturer's buffer recommendations. After an initial denaturation cycle of 10 minutes at 95° C. amplification was achieved with 30 cycles of 95° C. for 1 minute; 55° C. for 1 minute and 72° C. for 1.5 minutes. The final cycle was followed by 10 minutes at 72° C. to ensure complete polymerization. The amplified product (1.7 kb) was digested with KpnI and AgeI and ligated into pWHM1425 that had been digested with the same enzymes and gel isolated. The resulting plasmid was designated pAL3TPKSNT (pWHM1426). The region introduced by PCR was sequenced on a ABI automated DNA sequencer to ensure sequence fidelity. This plasmid was then used to transform A. nidulans strain A722 (Fungal Genetics Stock Centre) to uridine prototrophy.

Transformants were grown by inoculating 0.5 ml of spore suspension ($10^8$ c.f.u./ml) in 50 ml YEPD in a 250 ml unbaffled flask. This was then grown for 20 hours at 250 rmp and 37° C. (New Brunswick Scientific Series 25 Incubator Shaker). The mycelia were then harvested by filtration through MIRACLOTH (Calbiochem), rinsed with sterile, distilled water, and inoculated into fresh 250 ml unbaffled flasks containing 50 ml AMM+lactose+10 mM cyclopentanone and grown for a further 20 hours under the same conditions. The mycelia were harvested by filtration using MIRACLOTH (Calbiochem), squeezed as dry as possible and frozen in liquid nitrogen. Protein extracts for SDS-PAGE and western analysis were prepared as described in Kennedy and Turner, *Molec. Gen. Genet.* (1996), 253:189–197, 1996.

One transformant, WMH1738, was shown to have a large protein (>200 kDa) visible on a SDS-PAGE gel that cross reacted with the affinity purified NPKS antibodies (Panlabs). This strain WMH1738 was transformed to hygromycin B resistance with pWHM1263. Transformant colonies were screened for lovastatin resistance and for the production of new metabolites as described below and two strains WMH1739 and WMH1740 were chosen for further analysis. Both of these strains were found to be significantly resistant (up to 100 µg/ml on solid media) to lovastatin compared with the host strain. This was analyzed by streaking 10 µl of a spore suspension on solid AMM plates containing lovastatin at 0, 0.1, 0.5, 1, 5, 10, 50 and 100 µg/ml and incubating at 37° C. Strains WMH1739 and WMH1740 were compared to strains WMH1741 and WMH1742 which were derivatives of WMH1738 transformed to hygromycin resistance with AN26. Strains WMH1739 and −1740 exhibited no inhibition of growth at any of these lovastatin concentrations whereas strains WMH1741 and −1742 showed slight inhibition of grown at 5 µg/ml and almost complete growth inhibition at 50 µg/ml. The two lovastatin resistant strains were fermented in lovastatin-producing conditions using fermentation method B and extracts were analyzed for lovastatin related metabolites as described below. Both strains were found to produce new metabolites. One compound that was common to both comigrated with monacolin J on TLC and HPLC analysis by the methods described below. Semi-preparative HPLC was used to partially purify some of this compound, which was then analyzed by HPLC—MS. It had the same mass and fragmentation pattern as authentic monacolin J. The other compound, found in only one of the strains, comigrated with monacolin L on TLC and HPLC.

Methods

Solid Medium for Growth of A. terreus

For the generation of spore suspensions A. terreus strains were grown on CM agar at 30° C. for 4 to 5 days.

CM Agar (for CM liquid medium the agar was omitted):
50 ml Clutterbuck's salts (Vinci, et al., U.S. Pat. No. 5,744,350)
2 ml Vogel's trace elements (Vinci, et al., U.S. Pat. No. 5,744,350)
0.5% Difco BACTO tryptone
0.5% Difco BACTO yeast extract
1% glucose
2% Difco BACTO agar
in 1 liter of distilled water Clutterbuck's salts:
12% $NaNO_3$
1.02% KCl
1.04% $MgSO_4.7H_2O$
3.04% $KH_2PO_4$ Vogel's trace elements:
0.004% $ZnCl_2$
0.02% $FeCl_3$
0.001% $CuCl_2$
0.001% $MnCl_2.4H_2O$
0.001% $Na_2B_4O_7.10H_2O$
0.001% $(NH_4)_6Mo_7O_{24}.7H_2O$ For long term storage A. terreus spores were suspended in SSS (10% glycerol, 5% lactose) and stored at −70° C.

For the generation of spore stocks A. nidulans was grown on the following solid growth medium (ACM) for 3 to 4 days at 37° C.

ACM:
2% Difco BACTO malt extract
0.1% Difco BACTO peptone
2% glucose
2% agar (Difco, Detroit, Mich.)

For strains which required para-aminobenzoic acid (PABA) for growth, PABA was added to a final concentration of 1 µg/ml. For strains which required uracil and uridine these were added at 20 mM and 10 mM, respectively. Spores were suspended in TWEEN 80—saline solution (0.025% TWEEN 80, 0.8% NaCl) and stored at 4° C.

AMM:
0.6% (w/v) $NaNO_3$
0.052% (w/v) KCl
0.152% (w/v) $KH_2PO_4$
0.052% (w/v) $MgSO_4.7H_2O$
1% (w/v) glucose
0.1% (v/v) AMM trace elements solution pH to 6.5 and make up to 1 liter with distilled water.

For preparation of plates 2% (w/v) Difco Bacto agar was added. If required the glucose can be omitted and an alternative carbon source (e.g., lactose added at the same concentration). For the preparation of transformation plates KCl was added at 4.47% (w/v) (0.6 M).

AMM trace elements solution:
0.1% (w/v) $FeSO_4.7H_2O$
0.88% (w/v) $ZnSO_4.7H_2O$
0.04% (w/v) $CuSO_4.5H_2O$
0.015% (w/v) $MnSO_4.4H_2O$
0.01% (w/v) $Na_2B_4O_7.10H_2O$
0.005% $(NH_4)_6Mo_7O_{24}.7H_2O$ distilled water to 1 liter Large Scale Genomic DNA Preparation from A. terreus for Genomic Library Construction.

A 2.5 ml aliquot of spore suspension ($10^8$ c.f.u./ml) was used to inoculate 500 ml of liquid CM medium and grown for 20 hours at 30° C. and 200 rpm. The mycelium was harvested by filtration through MIRACLOTH (Calbiochem)

and rinsed extensively with water then TSE [150 mM NaCl, 100 mM Na$_2$EDTA, 50 mM TRIS (hydroxymethyl) aminomethane hydrochloride pH 8.0]. The mycelium was squeezed dry, broken into small pellets and frozen in liquid nitrogen then ground to a fine powder in a pre-chilled pestle and mortar followed by transferral to a 500 ml flask. Fifty ml of extraction buffer [150 mM NaCl, 100 mM Na$_2$EDTA, 50 mM TRIS (hydroxymethyl) aminomethane hydrochloride pH 8.0, 2% (w/v) SDS] and 10 ml of toluene was added to the flask which was shaken at 60 rpm for 72 hours. This mixture was centrifuged at 1000×g for 15 minutes and the supernatant was removed and extracted with an equal volume of chloroform:isoamyl alcohol (24:1 vol/vol). This mixture was centrifuged at 10,000×g for 30 minutes at 15° C. The aqueous layer was carefully removed and 1.1 volumes of ethanol was layered on top. The DNA was spooled out from the resulting suspension and resuspended in 5 ml TE [10 mM TRIS (hydroxymethyl) aminomethane hydrochloride pH 8.0, 1 mM EDTA]+50 µg/ml RNase and 100 µg/ml proteinase K then incubated at 37° C. for 2 hours. The mixture was extracted again with chloroform:isoamyl alcohol (24:1) and the DNA was spooled out as before. Following resuspension in 1 ml of TE the DNA was extracted once with phenol:chloroform:isoamyl alcohol (25:24:1, vol/vol), once with chloroform:isoamyl alcohol (24:1) and precipitated with 0.6 volumes isopropanol. The DNA clot was removed, dried briefly and resuspended in 0.5 ml TE.

Small Scale Genomic DNA Preparation from *A. terreus* for Southern Blot.

A 0.5 ml aliquot of spore suspension (10$^8$ c.f.u./ml) was used to inoculate 100 ml of liquid CM and grown for 20 hours at 30° C. and 200 rpm. The mycelium was harvested by filtration through MIRACLOTH (Calbiochem) and rinsed extensively with water then TSE [150 mM NaCl, 100 mM Na$_2$EDTA, 50 mM TRIS (hydroxymethyl) aminomethane hydrochloride pH 8.0]. The mycelium was squeezed dry, broken into small pellets and frozen in liquid nitrogen. The mycelium was ground to a fine powder in a pre-chilled pestle and mortar and transferred to a mortar pre-heated to 65° C. Three ml of lysis buffer [0.5 M NaCl, 10 mM TRIS (hydroxymethyl) aminomethane hydrochloride pH 7.5, 10 mM EDTA, 1% (w/v) SDS] at 65° C. was added and 0.3 ml of 10% (w/v) cetyltrimethylammonium bromide in 0.7 M NaCl. After thorough mixing to form a slurry, 3 ml of phenol:chloroform:isoamyl alcohol (25:24:1) was added. This mixture was transferred to a COREX tube and incubated at 65° C. for 15 minutes. Following centrifugation at 12,000×g for 15 minutes at 4° C. the aqueous phase was carefully removed and re-extracted once with phenol, once with phenol:chloroform:isoamyl alcohol (25:24:1) and once with chloroform:isoamyl alcohol (24:1). The DNA was precipitated from the extract by addition of 0.1 volume of 3 M sodium acetate pH 5 and 0.6 volumes isopropanol then collected by centrifugation (10,000×g, 10 minutes, 4° C.). After washing with 70% ethanol the pellet was briefly dried and resuspended in TE+RNase (50 µg/ml).

Transformation of *A. terreus*.

A 0.5 ml aliquot of spore suspension (10$^8$ c.f.u./ml) was used to inoculate 100 ml of liquid CM and grown for 20 hours at 30° C. and 200 rpm. The mycelium was harvested by centrifugation at 2000×g for 15 minutes at 4° C. and washed twice with an aqueous solution containing 0.27 M CaCl$_2$ and 0.6 M NaCl. To produce protoplasts the washed mycelia was resuspended in 20 ml of the same solution containing 5 mg/ml NOVOZYM 234 (NovoNordisk) and incubated at 30° C. for 1–3 hours with gentle agitation. Protoplasts were separated from undigested mycelia by filtration through MIRACLOTH (Calbiochem). The protoplast suspension was diluted with an equal volume of STC1700 [1.2 M sorbitol, 10 mM TRIS (hydroxymethyl) aminomethane hydrochloride pH 7.5, 35 mM NaCl] and incubated on ice for 10 minutes. The protoplasts were collected by centrifugation (2000×g, 10 minutes, 4° C.), washed with STC1700 and resuspended in 1 ml STC1700. Plasmid DNA, purified using Qiagen columns, (2–5 µg in 10 µl) was added to 150 µl of protoplast suspension and incubated at room temperature for 25 minutes. PEG solution [60% (w/v) polyethylene glycol 4000, 50 mM CaCl$_2$, 10 mM TRIS (hydroxymethyl) aminomethane hydrochloride pH 7.5] was added to the DNA/protoplasts mixture in three steps: 250 µl, 250 µl, and 850 µl with mixing after each addition. The suspension was incubated at room temperature for 25 minutes then diluted to 10 ml with STC1700. Protoplasts were collected by centrifugation as above and diluted with 500 µl STC1700. 100 µl aliquots of this mixture were plated onto osmotically stabilized plates [CM medium containing 3% (w/v) Difco Bacto agar and 23.4% (w/v) mannitol, 15 ml of agar per plate]. After 4 hours growth at 30° C., 25 ml of OL agar [1% (w/v) Difco BACTO peptone, 1% (w/v) Difco BACTO agar, 200 µg/ml Zeocin] was overlayered onto each dish. The plates were incubated for 3–4 days at 30° C. before transformant colonies were picked. These were streaked to single colonies twice on selective media (CM+100 µg/ml Zeocin) before spore suspensions were prepared.

Transformation of *A. nidulans*.

A 0.5 ml aliquot of spore suspension (10$^8$ c.f.u./ml) was used to inoculate 100 ml of YEPD [2% (w/v) Difco BACTO yeast extract, 2% (w/v) glucose, 0.1% Difco BACTO peptone] liquid medium including necessary supplements and grown for 20 hours at 37° C. and 200 rpm. The mycelia was harvested by centrifugation (2000×g, 10 minutes, 4° C.) and washed twice with 0.6 M KCl. To generate protoplasts the mycelia was resuspended in 20 ml of 0.6 M KCl containing 5 mg/ml NOVOZYM 234 and incubated at 30° C. for 1–2 hours with gentle shaking. Protoplasts were separated from undigested mycelia by filtration through MIRACLOTH (Calbiochem). The protoplasts were harvested by centrifugation as described above and washed twice with 0.6 M KCl, then resuspended in 10 ml 0.6 M KCl+50 mM CaCl$_2$. After counting in a haemocytometer the protoplasts were harvested by centrifugation as before and resuspended to a final concentration of 5×10$^8$ protoplasts/ml. To 50 µl of protoplast suspension, 5 µl of DNA (2–5 µg, purified using QIAGEN columns) was added, then 12.5 µl of PEG solution [25% (w/v) PEG 6000, 50 mM CaCl$_2$, 10 mM TRIS (hydroxymethyl) aminomethane hydrochloride pH 7.5] and the mixture was incubated on ice for 20 minutes. A further 0.5 ml of PEG solution was added and the mixture was incubated on ice for a further 5 minutes. A 1 ml aliquot of 0.6 M KCl+50 mM CaCl$_2$ was added and the protoplasts were plated out in 50 µl, 200 µl, and 400 µl aliquots. For transformation to uridine prototrophy, protoplasts were plated out onto AMM+0.6 M KCl plates without adding uridine or uracil supplements. Plates were incubated at 37° C. for 3–4 days when transformants were picked. For transformation to hygromycin B resistance protoplasts were plated out onto AMM +0.6 M KCl plates (15 ml) and incubated for 4 hours at 30° C. 30 ml of 1% peptone, 1% agar, 1 mg/ml hygromycin B was then used to overlay the plates, which were incubated for 3–4 days when transformants were picked. Transformants from both methods were streaked out to single colonies on selective media (i.e., lacking uridine/uracil supplements or containing 1 µg/ml hygromycin B) twice before spore suspensions were made.

Analysis of Strains for Lovastatin Production.

Two fermentation methods were used for the analysis of lovastatin production. In Method A, 0.5 ml of spore suspension ($10^8$ c.f.u./ml) was inoculated into 25 ml of SEED medium in 250 ml unbaffled flasks and grown for 18 hours at 250 rpm and 30° C. (New Brunswick Scientific Model 25 incubator/shaker). A 1 ml portion of the resulting seed culture was used to inoculate 25 ml of FM in a 250 ml unbaffled flask and grown for 6 days in the conditions described above. Fermentation Method B involved inoculating 50 ml of RPM in a 250 ml unbaffled flask with 0.5 ml of spore suspension ($10^8$ c.f.u./ml) and growing at 30° C. and 250 rpm for 7 days in a New Brunswick Scientific Series 25 Incubator Shaker.

SEED medium:
0.5% (w/v) Sigma corn steep liquor
4% (w/v) tomato paste
1% (w/v) oat flour
1% (w/v) glucose
1% (v/v) Vogel's trace elements
distilled water to 1 l
FM:
4.5% (w/v) glucose
2.4% (w/v) Sigma peptonized milk
0.25% (w/v) Difco BACTO yeast extract
0.25% (w/v) polyethylene glycol 2000
distilled water up to 1 l
RPM:
4% (w/v) lactose
0.3% (w/v) rapeseed meal
0.2% (w/v) $KNO_3$
0.3% (w/v) $KH_2PO_4$
0.05% (w/v) $MgSO_4.7H_2O$
0.05% (w/v) NaCl
0.05% (v/v) Sigma antifoam B
0.05% (v/v) trace elements solution
pH to 6.5 and made up to 1 l with distilled water.
Trace elements solution is:
0.16% (w/v) $MnSO_4$
0.34% (w/v) $ZnSO_4.7H_2O$
0.2% (w/v) $CoCl_2.6H_2O$
0.5% (w/v) $FeSO_4.7H_2O$
made up to 1 liter with distilled water.

The cultures were extracted by adjusting the pH of the media to 3 with HCl, adding an equal volume of ethyl acetate, and shaking the mixture on a New Brunswick Scientific Series 25 incubator/shaker at 250 rpm for 2 hours. For analysis, 1 ml of the ethyl acetate layer was dried under a nitrogen stream and resuspended in 0.1 ml of methanol. For TLC analysis 10 µl of this extract was run on C-18 reverse phase TLC plates (RP-18 $F_{254}$—Merck) in a solvent system of methanol:0.1% phosphoric acid (9:1). TLC plates were developed by spraying with 10% phosphomolybdic acid in methanol and heating with a heat gun. Extracts were compared with authentic lovastatin, monacolin J. monacolin L, and dihydromonacolin L (acid and lactone forms). For HPLC analysis a Waters Nova-Pak $C_{18}$ (3.9×150 mm) column was used with a solvent system of acetonitrile (B) and 0.1% phosphoric acid (A). The column was eluted with a preprogrammed gradient of 0 to 100% B into A over 25 minutes using gradient 7 (Waters Millenium Software) with a flow rate of 1.5 ml/min and metabolites were detected with a Waters 996 Photodiode Array Detector; lovastatin was detected at 238 nm. For purification of metabolites a Waters Prep Nova-Pak HR $C_{18}$ (7.8×300 mm) column was used. The same solvent system as above was used with gradient of 0 to 100% B in A over 75 minutes at a flow rate of 4.5 ml/min. Fractions were collected manually, back extracted with ethyl acetate and dried. For HPLC-MS an Aquapore OD-300 7 micron (1.0×100 mm) column was used with a gradient of 0 to 100% acetonitrile into A (0.05% TFA) over 30 minutes at a flow rate of 0.02 ml/min.

---

We claim:

1. A lovastatin-producing organism, wherein the organism has been genetically modified to have increased lovastatin production, wherein the modification is transformation with the D4B segment and wherein the increase is at least 5-fold relative to a non-transformed organism.

2. The organism of claim 1, wherein the organism is a fungi.

3. A non-lovastatin producing organism, wherein the organism has been genetically modified to produce monacolin J, wherein the modification is transformation with the D4B segment and wherein the increase is at least 5-fold.

4. The organism of claim 3, wherein the organism is a fungi.

5. A non-lovastatin producing organism, wherein the organism has been genetically modified to produce lovastatin wherein the modification is transformation with the D4B segment.

6. The organism of claim 5 wherein the organism is a fungi.

* * * * *

SEQUENCE LISTING

<160> NUMBER OF SEQ ID NOS: 36

<210> SEQ ID NO 1
<211> LENGTH: 1529
<212> TYPE: PRT
<213> ORGANISM: Aspergillus terreus

<400> SEQUENCE: 1

```
Met Ala Ser Leu Leu Phe Phe Thr Val Phe Asn Leu Thr Leu Ala Leu
 1               5                  10                  15

Leu Ser Ser Thr Ala Thr Gly Ala Ala Val Pro Val Ser Arg Pro Thr
            20                  25                  30

Asp Asp Ser Arg Tyr Ile Asp Phe Asp Ala Ala Glu Trp Arg Pro Arg
        35                  40                  45

Ala Lys Arg Asp Asp Ala Leu Lys Val Pro Leu Arg Ile Leu Pro Leu
    50                  55                  60

Gly Ala Ser Ile Thr Trp Gly Tyr Leu Ser Ser Thr Gly Asn Gly Tyr
65                  70                  75                  80

Arg Lys Pro Leu Arg Asp Lys Leu Arg Phe Glu Gly Trp Glu Val Asp
                85                  90                  95
```

```
Met Val Gly Lys Ala His Ser Gly Asp Val Ile Thr Gln Val Gln Thr
                100                 105                 110
Ala Ala Ala Asn Ser Leu Ala Tyr Lys Pro Asn Val Leu Ile Asn
        115                 120                 125
Ala Gly Thr Asn Asp Cys Asp Tyr Asn Val Asp Pro Ala Asn Ala Gly
    130                 135                 140
Glu Arg Met Arg Ser Leu Ile Glu Thr Leu Ile Gly Ala Pro Asp Met
145                 150                 155                 160
Ala Asn Thr Leu Ile Val Leu Ser Thr Leu Ile Pro Ser Gly Ser Thr
                165                 170                 175
Thr Leu Glu Ala Asn Arg Pro Ser Val Asn Ala Gln Phe Arg Glu Leu
            180                 185                 190
Val Leu Asp Met Arg Glu Ala Gln Asn Val Ser Ile Val Leu Ala Asp
        195                 200                 205
Met Asp Pro Pro Ala Pro Ser Pro Gly Asn Asn Trp Ile Thr Tyr Pro
    210                 215                 220
Asp Asn Phe Ala Asp Asn Lys His Pro Asn Asp Tyr Gly Tyr Ser Gln
225                 230                 235                 240
Met Ala Asp Ile Trp Tyr Asn Ala Ile Tyr Asn Ala Ala Val Ala Glu
                245                 250                 255
Leu Ile Val Lys Pro Ala Asp Leu Asp Ile Ser Ser Thr Gly Thr Cys
            260                 265                 270
Asp Lys Glu Tyr Gly Ser Gly Val Tyr Ala Gly Gly Phe Thr Gln Gln
        275                 280                 285
Gly Ser Gly Glu Asp Gly Ile Tyr Arg His Asp Ser Glu Tyr Ser
    290                 295                 300
Gly Ala Leu Phe Thr Val Arg Ala Gly Lys Gly Ala Ala Asp Pro Tyr
305                 310                 315                 320
Lys Asp Asp Asp Glu Leu His Phe Phe Phe Gly Arg Leu Tyr Thr Arg
                325                 330                 335
Ala Tyr Asp Asp Met Met Ile Phe His Lys Asp Lys Asp Ser Gly Ala
            340                 345                 350
Val Thr Phe Val Ser Tyr Thr Asn Asn Val His Thr Glu Glu Gln Glu
        355                 360                 365
Phe Thr Lys Gly Gly Thr Phe Ser Thr His Asn Asn Cys Asn Pro Gly
    370                 375                 380
Gly Val His Phe Ile Asp Ile Asn Gly Asp Gly Leu Asp Asp Tyr Ile
385                 390                 395                 400
Cys Ile Ala Leu Asp Gly Thr Thr Tyr Ala Ser Ile Asn Asn Gly Asp
                405                 410                 415
Gly Asp Ala Lys Ser Asn Lys Pro Pro Ser Phe Thr Asp Ile Gly Leu
            420                 425                 430
Trp Lys Ser Pro Glu Gly Tyr Asp Gln Ala His Val Arg Leu Ala Asp
        435                 440                 445
Ile Asp Gly Asp Gly Arg Ala Asp Tyr Cys Gly Leu Ala Asp Asn Gly
    450                 455                 460
Asp Val Thr Cys Trp Arg Asn Gly Trp Ile Glu Asp Ile Pro Ala Tyr
465                 470                 475                 480
Trp Gln Pro Leu Gly Lys Arg Phe Thr Gly Lys Val Met Gly Asp Leu
                485                 490                 495
Arg Gly Val Arg Phe Glu Asp Ile Asn Gly Asp Gly Arg Asp Asp Trp
            500                 505                 510
```

-continued

```
Met Trp Val Asp Asp Gly Ala Thr Thr Tyr Thr Asn Ser Arg
        515                 520                 525

Ser Cys Ile Lys Gly Glu Ser Gly Asp Gly Leu Asn Val Val Trp Arg
    530                 535                 540

Gln Gly Phe Tyr Gln Asp Ala Asn Ser Gly Pro Ser His Pro Gly Met
545                 550                 555                 560

Gly Val Ile Phe Gly Thr Ser Gly Leu Arg Asp Gln Val Tyr Phe Ala
                565                 570                 575

Arg Leu Tyr Gly Glu Val Ala Asp Phe Gly Glu Leu Gly Arg Gln Asp
                580                 585                 590

Tyr Val Phe Ile Lys Lys Asp Thr Ser Asp Lys Tyr Phe Gly Pro Leu
            595                 600                 605

Tyr Tyr Val His Val Trp Lys Ser Lys Gly Ala Gly Ala Lys Ile
            610                 615                 620

Lys Ala Asp Gly Asp Arg Tyr Cys Asn Met Met Gly His Asp Asn Gly
625                 630                 635                 640

Met Met Asp Tyr Ile Trp Ile His Ser Thr Gly His Met Arg Leu Tyr
                645                 650                 655

Pro Asn Arg Gly Leu Val Glu Val Pro Ala Asp Gly Ser Ser Phe Trp
                660                 665                 670

Gly Ala Asn Glu Ile Ile Phe Asp Pro Gln Glu Gln Ile Gly Met Lys
            675                 680                 685

Leu Asp Arg Arg Asp Leu His Leu Ala Asp Trp Asp Gly Asp Gly Ala
        690                 695                 700

Cys Asp Ile Ile Trp Thr Asp Pro Asp Asn Leu Asn Arg Ala Gln Val
705                 710                 715                 720

Trp Arg Asn Lys Ile Lys Asp Thr Gly Ser Phe Asp Trp Asp Tyr Asn
                725                 730                 735

Ile Asn Ala Ala Asp Glu Leu Tyr Cys Pro Glu His Arg Gly Leu Gly
                740                 745                 750

Phe Phe Asp Arg Pro Val His Phe Ala Asp Val Ser Gly Asn Gly Lys
            755                 760                 765

Ala Asp Tyr Leu Cys Val Glu Lys Asp Gly Arg Thr Trp Gly Trp Val
        770                 775                 780

Asn Gly Asp Asp Gly Trp Asp Tyr Ile Asp Gln Phe Lys Tyr Ser Glu
785                 790                 795                 800

Glu Lys Asp Arg Ala Asn Leu His Trp Ala Asp Val Asn Gly Asp Gly
                805                 810                 815

Lys Ala Asp Met Ile Trp Thr Asp Lys Phe Ser Gly Asp Gly Ser Val
                820                 825                 830

Trp Tyr Asn Leu Gly Gln Arg Asp Ile Lys Gly Ser Arg Tyr Glu Trp
            835                 840                 845

Gly Pro Gln Gly Pro Lys Tyr Arg Gly Ala Val Glu Gly Ser Cys Thr
        850                 855                 860

Tyr Phe Pro Asp Leu Asn Gly Asp Gly Arg Ala Asp Met His Ser Ile
865                 870                 875                 880

Trp Asn Ser Ile Asn Asn Thr Ala Gln Thr Trp Tyr Asn Glu Cys Ala
                885                 890                 895

Thr Lys Asp His Thr Gly Asp Asp Gly Pro Ile Thr Asn Pro Asn Leu
                900                 905                 910

Pro Val Ser Pro Val Lys Ala Pro Ile Glu Leu Thr Pro His Tyr Gln
            915                 920                 925
```

-continued

```
Asp Asn Ser Glu Cys Thr Arg Ala Gln Val Gln Thr Leu Phe Glu Glu
        930                 935                 940

Met Gln Tyr Ala Leu Asp Ala Ala Ser Glu Val Ala Tyr Phe Ser Gly
945                 950                 955                 960

Gly Ala Tyr Asp Pro Tyr Arg Asp Ile Phe Phe Ala Glu Ser Leu Thr
                965                 970                 975

Asp Ser Leu Thr Phe Thr Ile Asn Val Arg Tyr Thr Phe Asp Arg Met
            980                 985                 990

Val Thr Met Ile Ser Gly Ser Ser Gln Phe Asp Glu Lys Phe Thr
        995                 1000                1005

Ile Thr Cys Lys Asn Leu Arg Gly Cys Asp Glu Asn Gly Trp Leu Ala
    1010                1015                1020

Met Met Asn Asn Arg Asn Arg Leu Asn Phe Cys Pro Lys Phe Thr
1025                1030                1035                1040

Asp Glu Leu Lys Ser Ser Arg Arg Thr Arg Asp Tyr Val Tyr Gly Trp
                1045                1050                1055

Lys Gly Ala Arg Asp Leu Ala Ala Gly Thr Phe Asn Arg His Cys Ile
            1060                1065                1070

Glu Arg Gly Arg Lys Ala Glu Arg Ala Ala Asn Glu Leu Arg Ile Ala
        1075                1080                1085

Gly Asp Ala Asn Trp Gln Arg Arg Leu Leu Cys Pro Asp Pro Asn Asn
    1090                1095                1100

Leu Gly Gln Glu Gly Ile Cys Asp Ser Lys Leu Ser Ala Tyr Asn Ala
1105                1110                1115                1120

Asp Ser Trp Ala Leu Val Val Leu Gly Gly Tyr Tyr Thr Lys Ile Cys
            1125                1130                1135

Gly Arg Gln Ile Pro Leu Pro Glu Glu Ser Ala Ser Ser Ala Asp Asp
        1140                1145                1150

Ser Ser Cys Pro Ala Tyr Asp Asp Ser Ser Tyr Asp Ala Asp Thr Val
            1155                1160                1165

Tyr Gly Val Asn Asp Tyr Val His Phe Gly Asp Ser Tyr Ala Ala Gly
    1170                1175                1180

Met Gly Thr Gly Thr Thr Thr Gly Asp Ser Cys Arg Val Gly Ser Asn
1185                1190                1195                1200

Ser Tyr Gly Lys Leu Val Gln Glu Trp Phe Asp Thr Glu Asp Phe Thr
            1205                1210                1215

Tyr Thr Asn Tyr Ala Cys Ser Gly Asp Thr Thr Val Gly Leu Asn Lys
            1220                1225                1230

Lys Ile Asp Gln Trp Leu Gly Gln Asp Pro Thr Gly Thr Thr Met Ala
    1235                1240                1245

Thr Leu Thr Ile Gly Gly Asn Asp Val Phe Phe Ser Asp Leu Val Ser
1250                1255                1260

Asn Cys Val Leu Thr Met Trp Trp Tyr Ser Leu Glu Gln Tyr Arg Gln
1265                1270                1275                1280

Trp Cys Leu Glu Thr Glu Glu Lys Ala Arg Asn Leu Met Gln Asp Thr
            1285                1290                1295

Gly Ser Asp Gly Leu Gly Ser Lys Leu Arg Ala Ala Tyr Glu Lys Ile
        1300                1305                1310

Leu Asp Arg Ser Gly Ser Ser Val Tyr Leu Pro Val Ile Leu Ile Tyr
            1315                1320                1325

Ser Cys Arg Ala Val Leu Arg Arg Ala Asp Phe Thr Leu Val Val Gln
    1330                1335                1340
```

```
Pro Leu Arg Pro Trp Leu Cys His Leu Leu Gln Arg His Arg
1345                1350                1355                1360

Leu Arg Leu Asn His Leu Leu Glu Leu Asn Asp Leu Val Arg Met Leu
                1365                1370                1375

Asn Ser Leu Ile Gln Ser Thr Ile Ser Asp Ile Asn Thr Ala Arg Asn
            1380                1385                1390

Thr Glu Gln Ile His Tyr Ile Asp Met Asp Ala Arg Phe Asp Gly His
        1395                1400                1405

Arg Trp Cys Glu Pro Gly Thr Gln Glu Pro Asp Pro Asp Asn Pro Asn
    1410                1415                1420

Thr Tyr Phe Phe Leu Ser Ala Trp Pro Asp Ile Ala Ile Val Gly Asp
1425                1430                1435                1440

Thr Thr Ala Glu Ser Thr Asn Ala Thr Glu Thr Asp Glu Ile Thr Ala
                1445                1450                1455

Leu Met Asn Ser Gly Ser Ile Gln Leu Pro Asp Ala Asp Thr Cys Gln
            1460                1465                1470

Asp Ala Leu Gly Ser Asp Pro Asp Pro Tyr Ala Val Phe Met Cys Asp
        1475                1480                1485

Val Ala Val His Val Lys Ala Asn Ser Ser Ser Leu Ile Ala Gln Ser
    1490                1495                1500

Leu Asp Arg Ala Asn Gln Ala Ile Ala Asn Arg Asp Tyr Ser Ser Gln
1505                1510                1515                1520

Asp Val Ser Trp Trp Leu Pro Ser Pro
            1525

<210> SEQ ID NO 2
<211> LENGTH: 328
<212> TYPE: PRT
<213> ORGANISM: Aspergillus terreus

<400> SEQUENCE: 2

Met Thr Leu Pro Thr Leu Pro Asn Trp Ile Arg Met Cys Val His Leu
1                5                10                  15

Ser Leu Thr His Leu His Gln His Arg Ser Pro Lys Tyr Glu Ser Ile
                20                  25                  30

Pro Ile Lys Ser Ile Gln Ala Asn Ser His Arg Ile Leu Ile Ile Leu
            35                  40                  45

Thr Thr Ala Ser Phe Tyr Pro Gln Ile Arg Cys Ile Gln Leu Arg Asn
        50                  55                  60

Ser Thr His Gly Ile Ser Thr Ala Tyr Ile Leu Phe Asn Leu Ile Ser
65                  70                  75                  80

Ala Thr Glu His Phe Thr Ile Leu Phe Ala Leu Leu Val Asn Ser Gly
                85                  90                  95

Gly Asp Val Leu Ile His Glu Pro Pro Thr Thr Gly Asp Gly Leu Asn
                100                 105                 110

Leu Tyr Gln Leu Phe Ala Val Trp Met Gly Cys Leu Val Leu Phe Cys
            115                 120                 125

Gln Ala Ile His Ser Leu His Ala Asn Pro Arg Arg Lys Leu Ile Leu
        130                 135                 140

Leu Thr Ile Tyr Ile Gln Tyr Leu Cys Ile Ser Ile Leu Pro Glu Val
145                 150                 155                 160

Ile Asp Ala Ile Thr Thr Pro Glu Glu Thr Arg Lys Gln Arg Pro Pro
                165                 170                 175

Thr Gly Glu Arg Asn Trp Leu Ile Gly Leu Phe Leu Ser Ala His Ala
            180                 185                 190
```

```
Met Thr Val Leu Pro Leu Ser Ala Val Leu Arg Ile Ala Gly Phe Ile
            195                 200                 205

Asp Gln Ser Arg Leu Ile Ser Arg Arg Arg Glu Gln Pro Ser Val
        210                 215                 220

Leu Ser Leu Thr Gly Leu Ala Cys Gln Ala Val Val Phe Ala Leu Val
225                 230                 235                 240

Ser Gly Leu Trp Val Leu Arg Val Gln Gln Pro Val Pro Arg Met Pro
                245                 250                 255

Met Arg Arg Pro Val Asp Trp Met Tyr Trp Tyr His Val Ile Gly Trp
            260                 265                 270

Pro Val Val Asp Asp Ala Val Tyr Ala Leu Gly Gln Trp Val Leu Phe
        275                 280                 285

Trp Tyr Ala Val Cys Trp Arg Ser Arg Gly Asp Ala Arg Asp Glu Ala
290                 295                 300

Val His Ala Gly Glu Thr Asp Asp Leu Leu Gly Glu Asp Gly His
305                 310                 315                 320

Gly Tyr Gly Gly Thr Gly Thr Ser
                325
```

<210> SEQ ID NO 3
<211> LENGTH: 323
<212> TYPE: PRT
<213> ORGANISM: Aspergillus terreus

<400> SEQUENCE: 3

```
Met Val Gly Ser Lys Leu Ala His Asn Glu Glu Trp Leu Asp Ile Ala
  1               5                  10                  15

Lys His His Ala Val Thr Met Ala Ile Gln Ala Arg Gln Leu Arg Leu
                20                  25                  30

Trp Pro Val Ile Leu Arg Pro Leu Val His Trp Leu Glu Pro Gln Gly
            35                  40                  45

Ala Lys Leu Arg Ala Gln Val Arg Arg Ala Arg Gln Leu Leu Asp Pro
        50                  55                  60

Ile Ile Gln Glu Arg Arg Ala Glu Arg Asp Ala Cys Arg Ala Lys Gly
 65                  70                  75                  80

Ile Glu Pro Pro Arg Tyr Val Asp Ser Ile Gln Trp Phe Glu Asp Thr
                85                  90                  95

Ala Lys Gly Lys Trp Tyr Asp Ala Ala Gly Ala Gln Leu Ala Met Asp
            100                 105                 110

Phe Ala Gly Ile Tyr Gly Thr Ser Asp Leu Leu Ile Gly Gly Leu Val
        115                 120                 125

Asp Ile Val Arg His Pro His Leu Leu Glu Pro Leu Arg Asp Glu Ile
130                 135                 140

Arg Thr Val Ile Gly Gln Gly Gly Trp Thr Pro Ala Ser Leu Tyr Lys
145                 150                 155                 160

Leu Lys Leu Leu Asp Ser Cys Leu Lys Glu Ser Gln Arg Val Lys Pro
                165                 170                 175

Val Glu Cys Ala Thr Met Arg Ser Tyr Ala Leu Gln Asp Val Thr Phe
            180                 185                 190

Ser Asn Gly Thr Phe Ile Pro Lys Gly Glu Leu Val Ala Val Ala Ala
        195                 200                 205

Asp Arg Met Ser Asn Pro Glu Val Trp Pro Glu Pro Ala Lys Tyr Asp
210                 215                 220

Pro Tyr Arg Tyr Met Arg Leu Arg Glu Asp Pro Ala Lys Ala Phe Ser
225                 230                 235                 240
```

```
Ala Gln Leu Glu Asn Thr Asn Gly Asp His Ile Gly Phe Gly Trp His
            245                 250                 255

Pro Arg Ala Cys Pro Gly Arg Phe Phe Ala Ser Lys Glu Ile Lys Met
            260                 265                 270

Met Leu Ala Tyr Leu Leu Ile Arg Tyr Asp Trp Lys Val Val Pro Asp
            275                 280                 285

Glu Pro Leu Gln Tyr Tyr Arg His Ser Phe Ser Val Arg Ile His Pro
            290                 295                 300

Thr Thr Lys Leu Met Met Arg Arg Asp Glu Asp Ile Arg Leu Pro
305                 310                 315                 320

Gly Ser Leu

<210> SEQ ID NO 4
<211> LENGTH: 256
<212> TYPE: PRT
<213> ORGANISM: Aspergillus terreus

<400> SEQUENCE: 4

Met Arg Tyr Gln Ala Ser Pro Ala Leu Val Lys Ala Pro Arg Ala Leu
 1               5                  10                  15

Leu Cys Ile His Gly Ala Gly Cys Ser Pro Ala Ile Phe Arg Val Gln
                20                  25                  30

Leu Ser Lys Leu Arg Ala Ala Leu Arg Glu Asn Phe Glu Phe Val Tyr
            35                  40                  45

Val Thr Ala Pro Phe Pro Ser Ser Ala Gly Pro Gly Ile Leu Pro Val
        50                  55                  60

Phe Ala Asp Leu Gly Pro Tyr Tyr Ser Trp Phe Glu Ser Ser Ser Asp
 65                  70                  75                  80

Asn Asn His Asn Gly Pro Ser Val Ser Glu Arg Leu Ala Ala Val His
                85                  90                  95

Asp Pro Ile Arg Arg Thr Ile Val Asp Trp Gln Thr Gln His Pro His
            100                 105                 110

Ile Pro Ile Val Gly Ala Ile Gly Phe Ser Glu Gly Ala Leu Val Thr
        115                 120                 125

Thr Leu Leu Leu Trp Gln Gln Gln Met Gly His Leu Pro Trp Leu Pro
130                 135                 140

Arg Met Ser Val Ala Leu Leu Ile Cys Pro Trp Tyr Gln Asp Glu Ala
145                 150                 155                 160

Ser Gln Tyr Met Arg Asn Glu Val Met Lys Asn His Asp Asp Asp Asn
                165                 170                 175

Asp Ser Lys Asp Thr Glu Trp Gln Glu Glu Leu Val Ile Arg Ile Pro
            180                 185                 190

Thr Leu His Leu Gln Gly Arg Asp Asp Phe Ala Leu Ala Gly Ser Lys
        195                 200                 205

Met Leu Val Ala Arg His Phe Ser Pro Arg Glu Ala Gln Val Leu Glu
    210                 215                 220

Phe Ala Gly Gln His Gln Phe Pro Asn Arg Pro Arg Asp Val Leu Glu
225                 230                 235                 240

Val Ile Asn Arg Phe Arg Lys Leu Cys Val Thr Ala Gln Thr Leu Glu
                245                 250                 255

<210> SEQ ID NO 5
<211> LENGTH: 363
<212> TYPE: PRT
<213> ORGANISM: Aspergillus terreus
```

```
<400> SEQUENCE: 5

Met Gly Asp Gln Pro Phe Ile Pro Pro Gln Gln Thr Ala Leu Thr
 1               5                  10                  15

Val Asn Asp His Asp Glu Val Thr Val Trp Asn Ala Ala Pro Cys Pro
            20                  25                  30

Met Leu Pro Arg Asp Gln Val Tyr Val Arg Val Glu Ala Val Ala Ile
            35                  40                  45

Asn Pro Ser Asp Thr Lys Met Arg Gly Gln Phe Ala Thr Pro Trp Ala
        50                  55                  60

Phe Leu Gly Thr Asp Tyr Ala Gly Thr Val Val Ala Val Gly Ser Asp
 65                  70                  75                  80

Val Thr His Ile Gln Val Gly Asp Arg Val Tyr Gly Ala Gln Asn Glu
                85                  90                  95

Met Cys Pro Arg Thr Pro Asp Gln Gly Ala Phe Ser Gln Tyr Thr Val
            100                 105                 110

Thr Arg Gly Arg Val Trp Ala Lys Ile Pro Lys Gly Leu Ser Phe Glu
            115                 120                 125

Gln Ala Ala Leu Pro Ala Gly Ile Ser Thr Ala Gly Leu Ala Met
130                 135                 140

Lys Leu Leu Gly Leu Pro Leu Pro Ser Pro Ser Ala Asp Gln Pro Pro
145                 150                 155                 160

Thr His Ser Lys Pro Val Tyr Val Leu Val Tyr Gly Gly Ser Thr Ala
                165                 170                 175

Thr Ala Thr Val Thr Met Gln Met Leu Arg Leu Ser Gly Tyr Ile Pro
            180                 185                 190

Ile Ala Thr Cys Ser Pro His Asn Phe Asp Leu Ala Lys Ser Arg Gly
            195                 200                 205

Ala Glu Glu Val Phe Asp Tyr Arg Ala Pro Asn Leu Ala Gln Thr Ile
            210                 215                 220

Arg Thr Tyr Thr Lys Asn Asn Leu Arg Tyr Ala Leu Asp Cys Ile Thr
225                 230                 235                 240

Asn Val Glu Ser Thr Thr Phe Cys Phe Ala Ala Ile Gly Arg Ala Gly
                245                 250                 255

Gly His Tyr Val Ser Leu Asn Pro Phe Pro Glu His Ala Ala Thr Arg
            260                 265                 270

Lys Met Val Thr Thr Asp Trp Thr Leu Gly Pro Thr Ile Phe Gly Glu
            275                 280                 285

Gly Ser Thr Trp Pro Ala Pro Tyr Gly Arg Pro Gly Ser Glu Glu Glu
            290                 295                 300

Arg Gln Phe Gly Glu Asp Leu Trp Arg Ile Ala Gly Gln Leu Val Glu
305                 310                 315                 320

Asp Gly Arg Leu Val His His Pro Leu Arg Val Gln Gly Gly Phe
                325                 330                 335

Asp His Ile Lys Gln Gly Met Glu Leu Val Arg Lys Gly Glu Leu Ser
            340                 345                 350

Gly Glu Lys Leu Val Val Arg Leu Glu Gly Pro
            355                 360

<210> SEQ ID NO 6
<211> LENGTH: 413
<212> TYPE: PRT
<213> ORGANISM: Aspergillus terreus
```

```
<400> SEQUENCE: 6

Met Gly Ser Ile Ile Asp Ala Ala Ala Ala Asp Pro Val Val Leu
 1               5                  10                  15

Met Glu Thr Ala Phe Arg Lys Ala Val Lys Ser Arg Gln Ile Pro Gly
                20                  25                  30

Ala Val Ile Met Ala Arg Asp Cys Ser Gly Asn Leu Asn Tyr Thr Arg
            35                  40                  45

Cys Phe Gly Ala Arg Thr Val Arg Arg Asp Glu Cys Asn Gly Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
                100                 105                 110

Val Leu Glu Gly Phe Asp Asp Ala Gly Asn Ala Arg Leu Arg Glu Arg
            115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Met Ala Gln Gly
145                 150                 155                 160

His Leu Gln Ser Ala Glu Lys Phe Gly Ile Glx Ser Arg Leu Ala Pro
                165                 170                 175

Pro Ala Val Asn Asp Pro Gly Ala Glu Trp Ile Tyr Gly Ala Asn Leu
            180                 185                 190

Asp Trp Ala Gly Lys Leu Val Glu Arg Ala Thr Gly Leu Asp Leu Glu
    195                 200                 205

Gln Tyr Leu Gln Glu Asn Ile Cys Ala Pro Leu Gly Ile Thr Asp Met
    210                 215                 220

Thr Phe Lys Leu Gln Gln Arg Pro Asp Met Leu Ala Arg Arg Ala Asp
225                 230                 235                 240

Gln Thr His Arg Asn Ser Ala Asp Gly Arg Leu Arg Tyr Asp Asp Ser
                245                 250                 255

Val Tyr Phe Arg Ala Asp Gly Glu Glu Cys Phe Gly Gln Gly Val
            260                 265                 270

Phe Ser Gly Pro Gly Ser Tyr Met Lys Val Leu His Ser Leu Leu Lys
        275                 280                 285

Arg Asp Gly Leu Leu Gln Pro Gln Thr Val Asp Leu Met Phe Gln
    290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Ile Ile Ala Leu Glu Asp Leu Asp Gly
            340                 345                 350

Glu Asn Trp Arg Arg Lys Gly Ser Leu Thr Phe Gly Gly Pro Asn
    355                 360                 365

Ile Val Trp Gln Ile Asp Pro Lys Ala Gly Leu Cys Thr Leu Ala Phe
    370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
                405                 410
```

<210> SEQ ID NO 7
<211> LENGTH: 1068
<212> TYPE: PRT
<213> ORGANISM: Aspergillus terreus

<400> SEQUENCE: 7

```
Met Asp Pro Val Val Arg Lys Pro Asp Pro Gly Val Gln His Arg
  1               5                  10                  15

Val Thr Lys Ala Leu Arg Ala Ile Val Gly His Ala Cys Arg His Pro
             20                  25                  30

Ile His Thr Leu Leu Val Thr Ala Leu Thr Ala Thr Thr His Leu
         35                  40                  45

His Val Leu Glu Gly Thr Tyr Gln Ala Thr His Arg Glu Ala Ser Ala
     50                  55                  60

Trp Lys Trp Gln Ile Asp Asp Arg Pro Lys Val Pro Glu Asp Gly Gln
 65                  70                  75                  80

Ser Asp Phe His Trp Ala Leu Val Thr Leu Asp Leu Pro Gly Ala Ser
                 85                  90                  95

Val Asp Ala Ser Ile Pro Phe Leu Ser Asn Thr Leu Ser Gly Phe Leu
            100                 105                 110

Gly Ala Glu Gln Thr Thr Pro Thr Pro Asp Ser Ser Pro Ser Pro Asp
        115                 120                 125

His Ser Ala Leu Thr Phe Arg Val Pro Tyr Ser Gln Leu Asp Gly Phe
    130                 135                 140

Leu Gln Ala Val Glu Ile Ile Pro Ser Glu Lys Glu Asp Asp Ser Trp
145                 150                 155                 160

Arg Leu Arg Ser Pro Arg Glu Glu Gly Ser Pro Arg Ser Leu Gly His
                165                 170                 175

Trp Leu Gly Ser Ser Trp Leu Ser Phe Leu His Arg Val His His Ala
            180                 185                 190

Glu Thr Val Asp Leu Val Ile Ile Gly Leu Ser Tyr Leu Ala Met Asn
        195                 200                 205

Met Thr Val Val Ser Leu Phe Arg Val Met Arg His Leu Gly Ser Arg
    210                 215                 220

Phe Trp Leu Ala Ala Ser Val Leu Leu Ser Gly Ala Phe Ala Phe Val
225                 230                 235                 240

Leu Gly Leu Gly Ile Thr Thr Thr Cys Asp Val Pro Val Asp Met Leu
                245                 250                 255

Leu Leu Phe Glu Gly Ile Pro Tyr Leu Val Leu Thr Val Gly Phe Glu
            260                 265                 270

Lys Pro Ile Gln Leu Thr Arg Ala Val Leu Cys Val Ser Glu Glu Leu
        275                 280                 285

Trp Gly Gly Gln Arg Gln Val Pro Asn Gly Ala Ser Ser Asp Asp
    290                 295                 300

Ser Arg Gln Asn Gln Leu Ile Pro Asn Ile Gln Leu Ala Val Asp
305                 310                 315                 320

Arg Glu Gly Trp Tyr Ile Val Arg Ser Tyr Leu Leu Glu Ile Gly Ala
                325                 330                 335

Leu Ala Leu Gly Ala Val Leu Arg Pro Lys Asp Ser Leu Gly His Phe
            340                 345                 350

Cys Phe Leu Ala Ala Trp Thr Leu Ile Asp Ala Val Leu Leu Phe
        355                 360                 365

Thr Phe Tyr Ala Thr Ile Leu Cys Val Lys Leu Glu Ile Thr Arg Ile
    370                 375                 380
```

-continued

```
Arg Ser Pro Gly Gly Leu Gly Gln Val Asn Ala Lys His Pro Ser Gly
385                 390                 395                 400

Ile Phe Gly His Lys Val Lys Ser Thr Asn Ile Thr Trp Trp Lys Leu
            405                 410                 415

Leu Thr Val Gly Gly Phe Val Leu Cys His Phe Leu Gln Leu Ser Pro
            420                 425                 430

Phe Phe Tyr Arg Val Met Gly Glu Tyr Met Ala Asn Gly Thr Leu Pro
            435                 440                 445

Pro Thr Ala Val Ser Pro Phe Lys Glu Ala Ala Asn Gly Leu Asn Glu
            450                 455                 460

Ile Tyr Leu Thr Ala Arg Val Glu Gly Phe Glu Thr Arg Val Thr Val
465                 470                 475                 480

Leu Pro Pro Leu Gln Tyr Val Leu Glu Ser Ala Gly Phe Asn Ile Ser
                485                 490                 495

Ala Thr Lys Arg Ser Thr Phe Asp Gly Val Leu Asp Gly Leu Glu Ser
                500                 505                 510

Pro Leu Gly Arg Leu Cys Leu Met Gly Ala Leu Val Val Ser Leu Val
                515                 520                 525

Leu Asn Asn His Leu Ile His Ala Ala Arg Trp His Ala Trp Pro Gln
530                 535                 540

Ala Arg Glu Ser Ala Val Pro Asp Gly Ser Tyr Leu Ser Val Pro Cys
545                 550                 555                 560

Ser Ala Thr Ala Pro Glu Val Cys Thr Arg Pro Pro Glu Glu Thr Glu
                565                 570                 575

Ala Leu Leu Lys Ser Asn Gln Ala Glu Ser Leu Thr Asp Asp Glu Leu
                580                 585                 590

Val Glu Leu Cys Leu Arg Gly Lys Ile Ala Gly Tyr Ser Leu Glu Lys
                595                 600                 605

Thr Leu Glu Arg Ile Ala Ala Gly Ser Ser Arg Ser Val Thr Arg Leu
610                 615                 620

Glu Ala Phe Thr Arg Ala Val Arg Ile Arg Arg Ala Ala Val Ser Lys
625                 630                 635                 640

Thr Pro Ser Thr Gln Asn Leu Cys Ser Gly Leu Ala Glu Ser Leu Leu
                645                 650                 655

Pro Tyr Arg Asp Tyr Asn Tyr Glu Leu Val His Gly Ala Cys Cys Glu
                660                 665                 670

Asn Val Val Gly Tyr Leu Pro Leu Pro Leu Gly Val Ala Gly Pro Met
                675                 680                 685

Val Ile Asp Gly Gln Ala Leu Phe Ile Pro Met Ala Thr Thr Glu Gly
            690                 695                 700

Val Leu Val Ala Ser Ala Ser Arg Gly Cys Lys Ala Ile Asn Ala Gly
705                 710                 715                 720

Gly Gly Ala Thr Thr Met Leu Lys Gly Asp Gly Met Thr Arg Gly Pro
                725                 730                 735

Cys Leu Arg Phe Pro Ser Ala Gln Arg Ala Glu Ala Gln Arg Trp
                740                 745                 750

Val Glu Ser Pro Leu Gly His Glu Val Leu Ala Ala Phe Asn Ala
            755                 760                 765

Thr Ser Arg Phe Ala Arg Leu Gln Thr Leu Thr Val Ala Gln Ala Gly
            770                 775                 780

Ile Tyr Leu Tyr Ile Arg Phe Arg Thr Thr Thr Gly Asp Ala Met Gly
785                 790                 795                 800
```

-continued

Met Asn Met Ile Ser Lys Gly Val Glu Lys Ala Leu Glu Ala Met Ala
                805                 810                 815
Ala Glu Gly Gly Phe Pro Asp Met His Thr Val Thr Leu Ser Gly Asn
            820                 825                 830
Phe Cys Ser Asp Lys Lys Ser Ala Ala Ile Asn Trp Ile Gly Gly Arg
        835                 840                 845
Gly Lys Ser Val Ile Ala Glu Ala Thr Ile Pro Ala Glu Thr Val Arg
850                 855                 860
Gln Val Leu Lys Thr Asp Val Asp Ala Leu Val Glu Leu Asn Thr Ala
865                 870                 875                 880
Lys Asn Leu Val Gly Ser Ala Met Ala Gly Ser Leu Gly Gly Phe Asn
                885                 890                 895
Ala His Ala Ser Asn Leu Val Gln Ala Val Phe Leu Ala Thr Gly Gln
            900                 905                 910
Asp Pro Ala Gln Asn Val Glu Ser Ser Cys Ile Thr Thr Met Lys
        915                 920                 925
Asn Ile Asp Gly Asn Leu His Ile Ala Val Ser Met Pro Ser Met Glu
930                 935                 940
Val Gly Thr Ile Gly Gly Gly Thr Ile Leu Glu Ala Gln Gly Ala Met
945                 950                 955                 960
Leu Asp Leu Leu Gly Val Arg Gly Ala His Ser Thr Glu Pro Gly Ala
                965                 970                 975
Asn Ala Arg Arg Leu Ala Arg Ile Val Ala Ala Val Leu Ala Gly
            980                 985                 990
Glu Leu Ser Thr Cys Ala Ala Leu Ala Ala Gly His Leu Val Asn Ala
        995                 1000                1005
His Met Gln His Asn Arg Thr Ser Lys Asp Ala Ile Ser Gly Thr Glu
    1010                1015                1020
Tyr Gly Ala Ile Arg Thr Pro Val Tyr Val Ile Leu Glu His Ala
1025                1030                1035                1040
Gly Asp Ile His Phe Val Gln Ile Glu Tyr Lys Asn Thr Tyr Leu Arg
                1045                1050                1055
Arg Lys Val Pro Thr Leu Ser Cys Asn Leu Gly Arg
            1060                1065

<210> SEQ ID NO 8
<211> LENGTH: 503
<212> TYPE: PRT
<213> ORGANISM: Aspergillus terreus

<400> SEQUENCE: 8

Met Ala Ala Asp Gln Gly Ile Phe Thr Asn Ser Val Thr Leu Ser Pro
 1               5                  10                  15
Val Glu Gly Ser Arg Thr Gly Thr Leu Pro Arg Arg Ala Phe Arg
                20                  25                  30
Arg Ser Cys Asp Arg Cys His Ala Gln Lys Ile Lys Cys Thr Gly Asn
        35                  40                  45
Lys Glu Val Thr Gly Arg Ala Pro Cys Gln Arg Cys Gln Gln Ala Gly
    50                  55                  60
Leu Arg Cys Val Tyr Ser Glu Arg Cys Pro Lys Arg Lys Leu Arg Gln
65                  70                  75                  80
Ser Arg Ala Ala Asp Leu Val Ser Ala Asp Pro Asp Pro Cys Leu His
                85                  90                  95
Met Ser Ser Pro Pro Val Pro Ser Gln Ser Leu Pro Leu Asp Val Ser
            100                 105                 110

```
Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
            165                 170                 175

Glu Lys Ala Pro Leu Pro Pro Val Ser Ser Asp Ile Ala Arg Ala Ala
                180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
        210                 215                 220

Ile Trp Thr Arg Ala Ser Pro His Ser Pro Thr Ala Ser Arg Glu Arg
225                 230                 235                 240

Ile Ala Gln Arg Arg Gln Asn Val Trp Ala Asn Trp Leu Thr Asp Leu
                245                 250                 255

His Met Phe Ser Leu Asp Pro Ile Gly Met Phe Phe Asn Ala Ser Arg
            260                 265                 270

Arg Leu Leu Thr Val Leu Arg Gln Gln Ala Gln Ala Asp Cys His Gln
        275                 280                 285

Gly Thr Leu Asp Glu Cys Leu Arg Thr Lys Asn Leu Phe Thr Ala Val
290                 295                 300

His Cys Tyr Ile Leu Asn Val Arg Ile Leu Thr Ala Ile Ser Glu Leu
305                 310                 315                 320

Leu Leu Ser Gln Ile Arg Arg Thr Gln Asn Ser His Met Ser Pro Leu
                325                 330                 335

Glu Gly Ser Arg Ser Gln Ser Pro Ser Arg Asp Asp Thr Ser Ser Ser
            340                 345                 350

Ser Gly His Ser Ser Val Asp Thr Ile Pro Phe Phe Ser Glu Asn Leu
        355                 360                 365

Pro Ile Gly Glu Leu Phe Ser Tyr Val Asp Pro Leu Thr His Ala Leu
370                 375                 380

Phe Ser Ala Cys Thr Thr Leu His Val Gly Val Gln Leu Leu Arg Glu
385                 390                 395                 400

Asn Glu Ile Thr Leu Gly Val His Ser Ala Gln Gly Ile Ala Ala Ser
                405                 410                 415

Ile Ser Met Ser Gly Glu Pro Gly Glu Asp Ile Ala Arg Thr Gly Ala
            420                 425                 430

Thr Asn Ser Ala Arg Cys Glu Glu Gln Pro Thr Thr Pro Ala Ala Arg
        435                 440                 445

Val Leu Phe Met Phe Leu Ser Asp Glu Gly Ala Phe Gln Glu Ala Lys
450                 455                 460

Ser Ala Gly Ser Arg Gly Arg Thr Ile Ala Ala Leu Arg Arg Cys Tyr
465                 470                 475                 480

Glu Asp Ile Phe Ser Leu Ala Arg Lys His Lys His Gly Met Leu Arg
                485                 490                 495

Asp Leu Asn Asn Ile Pro Pro
            500
```

-continued

<210> SEQ ID NO 9
<211> LENGTH: 542
<212> TYPE: PRT
<213> ORGANISM: Aspergillus terreus

<400> SEQUENCE: 9

```
Met Thr Ser His His Gly Glu Thr Glu Lys Pro Gln Ser Asn Thr Ala
 1               5                  10                  15

Gln Met Gln Ile Asn His Val Thr Gly Leu Arg Leu Gly Leu Val Val
             20                  25                  30

Val Ser Val Thr Leu Val Ala Phe Leu Met Leu Leu Asp Met Ser Ile
         35                  40                  45

Ile Val Thr Ala Ile Pro His Ile Thr Ala Gln Phe His Ser Leu Gly
     50                  55                  60

Asp Val Gly Trp Tyr Gly Ser Ala Tyr Leu Leu Ser Ser Cys Ala Leu
 65                  70                  75                  80

Gln Pro Leu Ala Gly Lys Leu Tyr Thr Leu Thr Leu Lys Tyr Thr
                 85                  90                  95

Phe Leu Ala Phe Leu Gly Leu Phe Glu Ile Gly Ser Val Leu Cys Gly
                100                 105                 110

Thr Ala Arg Ser Ser Thr Met Leu Ile Val Gly Arg Ala Val Ala Gly
            115                 120                 125

Met Gly Gly Ser Gly Leu Thr Asn Gly Ala Ile Thr Ile Leu Ser Ala
        130                 135                 140

Ala Ala Pro Lys Gln Gln Gln Pro Leu Leu Ile Gly Ile Met Met Gly
145                 150                 155                 160

Leu Ser Gln Ile Ala Ile Val Cys Gly Pro Leu Leu Gly Gly Ala Phe
                165                 170                 175

Thr Gln His Ala Ser Trp Arg Trp Cys Phe Tyr Ile Asn Leu Pro Ile
            180                 185                 190

Gly Ala Phe Ala Thr Phe Leu Leu Val Ile Gln Ile Pro Asn Arg
        195                 200                 205

Leu Pro Ser Thr Ser Asp Ser Thr Thr Asp Gly Thr Asn Pro Lys Arg
    210                 215                 220

Arg Gly Ala Arg Asp Val Leu Thr Gln Leu Asp Phe Leu Gly Phe Val
225                 230                 235                 240

Leu Phe Ala Gly Phe Ala Ile Met Ile Ser Leu Ala Leu Glu Trp Gly
                245                 250                 255

Gly Ser Asp Tyr Ala Trp Asn Ser Ser Val Ile Ile Gly Leu Phe Cys
            260                 265                 270

Ala Ala Gly Val Ser Leu Val Leu Phe Gly Cys Trp Glu Arg His Val
        275                 280                 285

Gly Gly Ala Val Ala Met Ile Pro Ile Ser Val Ala Ser Arg Arg Gln
    290                 295                 300

Val Trp Cys Ser Cys Phe Phe Leu Gly Phe Phe Ser Gly Ala Leu Leu
305                 310                 315                 320

Ile Phe Ser Tyr Tyr Leu Pro Ile Tyr Phe Gln Ala Val Lys Asn Val
                325                 330                 335

Ser Pro Thr Met Ser Gly Val Tyr Met Leu Pro Gly Ile Gly Gly Gln
            340                 345                 350

Ile Val Met Ala Ile Val Thr Gly Ala Ile Ile Gly Lys Thr Gly Tyr
        355                 360                 365

Tyr Val Pro Trp Ala Leu Ala Ser Gly Ile Leu Val Ser Ile Ser Ala
    370                 375                 380
```

-continued

```
Gly Leu Val Ser Thr Phe Gln Pro Glu Thr Ser Ile Ala Ala Trp Val
385                 390                 395                 400

Met Tyr Gln Phe Leu Gly Gly Val Gly Arg Gly Cys Gly Met Gln Thr
                405                 410                 415

Pro Val Val Ala Ile Gln Asn Ala Leu Pro Pro Gln Thr Ser Pro Ile
            420                 425                 430

Gly Ile Ser Leu Ala Met Phe Gly Gln Thr Phe Gly Gly Ser Leu Phe
        435                 440                 445

Leu Thr Leu Thr Glu Leu Val Phe Ser Asn Gly Leu Asp Ser Gly Leu
    450                 455                 460

Arg Gln Tyr Ala Pro Thr Leu Asn Ala Gln Glu Val Thr Ala Ala Gly
465                 470                 475                 480

Ala Thr Gly Phe Arg Gln Val Val Pro Ala Pro Leu Ile Ser Arg Val
                485                 490                 495

Leu Leu Ala Tyr Ser Lys Gly Val Asp His Ala Phe Tyr Val Ala Val
            500                 505                 510

Gly Ala Ser Gly Ala Thr Phe Ile Phe Ala Trp Gly Met Gly Arg Leu
        515                 520                 525

Ala Trp Arg Gly Trp Arg Met Gln Glu Lys Gly Arg Ser Glu
    530                 535                 540

<210> SEQ ID NO 10
<211> LENGTH: 2532
<212> TYPE: PRT
<213> ORGANISM: Aspergillus terreus

<400> SEQUENCE: 10

Met Thr Pro Leu Asp Ala Pro Gly Ala Pro Ala Pro Ile Ala Met Val
1               5                   10                  15

Gly Met Gly Cys Arg Phe Gly Gly Ala Thr Asp Pro Gln Lys Leu
            20                  25                  30

Trp Lys Leu Glu Glu Gly Gly Ser Ala Trp Ser Lys Ile Pro Pro
        35                  40                  45

Ser Arg Phe Asn Val Gly Val Tyr His Pro Asn Gly Gln Arg Val
    50                  55                  60

Gly Ser Met His Val Arg Gly His Phe Leu Asp Glu Asp Pro Ala
65                  70                  75                  80

Leu Phe Asp Ala Ser Phe Phe Asn Met Ser Thr Glu Val Ala Ser Cys
                85                  90                  95

Met Asp Pro Gln Tyr Arg Leu Ile Leu Glu Val Val Tyr Glu Ala Leu
            100                 105                 110

Glu Ala Ala Gly Ile Pro Leu Glu Gln Val Ser Gly Ser Lys Thr Gly
        115                 120                 125

Val Phe Ala Gly Thr Met Tyr His Asp Tyr Gln Gly Ser Phe Gln Arg
    130                 135                 140

Gln Pro Glu Ala Leu Pro Arg Tyr Phe Ile Thr Gly Asn Ala Gly Thr
145                 150                 155                 160

Met Leu Ala Asn Arg Val Ser His Phe Tyr Asp Leu Arg Gly Pro Ser
                165                 170                 175

Val Ser Ile Asp Thr Ala Cys Ser Thr Thr Leu Thr Ala Leu His Leu
            180                 185                 190

Ala Ile Gln Ser Leu Arg Ala Gly Glu Ser Asp Met Ala Ile Val Ala
        195                 200                 205

Gly Ala Asn Leu Leu Leu Asn Pro Asp Val Phe Thr Thr Met Ser Asn
    210                 215                 220
```

```
Leu Gly Phe Leu Ser Ser Asp Gly Ile Ser Tyr Ser Phe Asp Ser Arg
225                 230                 235                 240

Ala Asp Gly Tyr Gly Arg Gly Glu Gly Val Ala Ile Val Leu Lys
        245                 250                 255

Thr Leu Pro Asp Ala Val Arg Asp Gly Asp Pro Ile Arg Leu Ile Val
                260                 265                 270

Arg Glu Thr Ala Ile Asn Gln Asp Gly Arg Thr Pro Ala Ile Ser Thr
        275                 280                 285

Pro Ser Gly Glu Ala Gln Glu Cys Leu Ile Gln Asp Cys Tyr Gln Lys
        290                 295                 300

Ala Gln Leu Asp Pro Lys Gln Thr Ser Tyr Val Glu Ala His Gly Thr
305                 310                 315                 320

Gly Thr Arg Ala Gly Asp Pro Leu Glu Leu Ala Val Ile Ser Ala Ala
                325                 330                 335

Phe Pro Gly Gln Gln Ile Gln Val Gly Ser Val Lys Ala Asn Ile Gly
                340                 345                 350

His Thr Glu Ala Val Ser Gly Leu Ala Ser Leu Ile Lys Val Ala Leu
        355                 360                 365

Ala Val Glu Lys Gly Val Ile Pro Pro Asn Ala Arg Phe Leu Gln Pro
370                 375                 380

Ser Lys Lys Leu Leu Lys Asp Thr His Ile Gln Ile Pro Leu Cys Ser
385                 390                 395                 400

Gln Ser Trp Ile Pro Thr Asp Gly Val Arg Arg Ala Ser Ile Asn Asn
                405                 410                 415

Phe Gly Phe Gly Gly Ala Asn Ala His Ala Ile Val Glu Gln Tyr Gly
                420                 425                 430

Pro Phe Ala Glu Thr Ser Ile Cys Pro Pro Asn Gly Tyr Ser Gly Asn
        435                 440                 445

Tyr Asp Gly Asn Leu Gly Thr Asp Gln Ala His Ile Tyr Val Leu Ser
450                 455                 460

Ala Lys Asp Glu Asn Ser Cys Met Arg Met Val Ser Arg Leu Cys Asp
465                 470                 475                 480

Tyr Ala Thr His Ala Arg Pro Ala Asp Asp Leu Gln Leu Leu Ala Asn
                485                 490                 495

Ile Ala Tyr Thr Leu Gly Ser Arg Arg Ser Asn Phe Arg Trp Lys Ala
                500                 505                 510

Val Cys Thr Ala His Ser Leu Thr Gly Leu Ala Gln Asn Leu Ala Gly
        515                 520                 525

Glu Gly Met Arg Pro Ser Lys Ser Ala Asp Gln Val Arg Leu Gly Trp
        530                 535                 540

Val Phe Thr Gly Gln Gly Ala Gln Trp Phe Ala Met Gly Arg Glu Leu
545                 550                 555                 560

Ile Glu Met Tyr Pro Val Phe Lys Glu Ala Leu Leu Glu Cys Asp Gly
                565                 570                 575

Tyr Ile Lys Glu Met Gly Ser Thr Trp Ser Ile Ile Glu Glu Leu Ser
                580                 585                 590

Arg Pro Glu Thr Glu Ser Arg Val Asp Gln Ala Glu Phe Ser Leu Pro
        595                 600                 605

Leu Ser Thr Ala Leu Gln Ile Ala Leu Val Arg Leu Leu Trp Ser Trp
        610                 615                 620

Asn Ile Gln Pro Val Ala Val Thr Ser His Ser Ser Gly Glu Ala Ala
625                 630                 635                 640
```

-continued

```
Ala Ala Tyr Ala Ile Gly Ala Leu Thr Ala Arg Ser Ala Ile Gly Ile
            645                 650                 655

Ser Tyr Ile Arg Gly Ala Leu Thr Ala Arg Asp Arg Leu Ala Ser Val
        660                 665                 670

His Lys Gly Gly Met Leu Ala Val Gly Leu Ser Arg Ser Glu Val Gly
            675                 680                 685

Ile Tyr Ile Arg Gln Val Pro Leu Gln Ser Glu Glu Cys Leu Val Val
        690                 695                 700

Gly Cys Val Asn Ser Pro Ser Val Thr Val Ser Gly Asp Leu Ser
705                 710                 715                 720

Ala Ile Ala Lys Leu Glu Glu Leu Leu His Ala Asp Arg Ile Phe Ala
            725                 730                 735

Arg Arg Leu Lys Val Thr Gln Ala Phe His Ser His Met Asn Ser
        740                 745                 750

Met Thr Asp Ala Phe Arg Ala Gly Leu Thr Glu Leu Phe Gly Ala Asp
            755                 760                 765

Pro Ser Asp Ala Ala Asn Ala Ser Lys Asp Val Ile Tyr Ala Ser Pro
770                 775                 780

Arg Thr Gly Ala Arg Leu His Asp Met Asn Arg Leu Arg Asp Pro Ile
785                 790                 795                 800

His Trp Val Glu Cys Met Leu His Pro Val Glu Phe Glu Ser Ala Phe
            805                 810                 815

Arg Arg Met Cys Leu Asp Glu Asn Asp His Met Pro Lys Val Asp Arg
        820                 825                 830

Val Ile Glu Ile Gly Pro His Gly Ala Leu Gly Gly Pro Ile Lys Gln
        835                 840                 845

Ile Met Gln Leu Pro Glu Leu Ala Thr Cys Asp Ile Pro Tyr Leu Ser
        850                 855                 860

Cys Leu Ser Arg Gly Lys Ser Ser Leu Ser Thr Leu Arg Leu Leu Ala
865                 870                 875                 880

Ser Glu Leu Ile Arg Ala Gly Phe Pro Val Asp Leu Asn Ala Ile Asn
            885                 890                 895

Phe Pro Arg Gly Cys Glu Ala Ala Arg Val Gln Val Leu Ser Asp Leu
        900                 905                 910

Pro Pro Tyr Pro Trp Asn His Glu Thr Arg Tyr Trp Lys Glu Pro Arg
        915                 920                 925

Ile Ser Gln Ser Ala Arg Gln Arg Lys Gly Pro Val His Asp Leu Ile
        930                 935                 940

Gly Leu Gln Glu Pro Leu Asn Leu Pro Leu Ala Arg Ser Trp His Asn
945                 950                 955                 960

Val Leu Arg Val Ser Asp Leu Pro Trp Leu Arg Asp His Val Val Gly
            965                 970                 975

Ser His Ile Val Phe Pro Gly Ala Gly Phe Val Cys Met Ala Val Met
            980                 985                 990

Gly Ile Ser Thr Leu Cys Ser Ser Asp His Glu Ser Asp Ile Ser
        995                 1000                1005

Tyr Ile Leu Arg Asp Val Asn Phe Ala Gln Ala Leu Ile Leu Pro Ala
        1010                1015                1020

Asp Gly Glu Glu Gly Ile Asp Leu Arg Leu Thr Ile Cys Ala Pro Asp
1025                1030                1035                1040

Gln Ser Leu Gly Ser Gln Asp Trp Gln Arg Phe Leu Val His Ser Ile
            1045                1050                1055
```

-continued

```
Thr Ala Asp Lys Asn Asp Trp Thr Glu His Cys Thr Gly Leu Val Arg
        1060                1065                1070

Ala Glu Met Asp Gln Pro Pro Ser Ser Leu Ser Asn Gln Gln Arg Ile
        1075                1080                1085

Asp Pro Arg Pro Trp Ser Arg Lys Thr Ala Pro Gln Glu Leu Trp Asp
    1090                1095                1100

Ser Leu His Arg Val Gly Ile Arg His Gly Pro Phe Phe Arg Asn Ile
1105                1110                1115                1120

Thr Cys Ile Glu Ser Asp Gly Arg Gly Ser Trp Cys Thr Phe Ala Ile
            1125                1130                1135

Ala Asp Thr Ala Ser Ala Met Pro His Ala Tyr Glu Ser Gln His Ile
        1140                1145                1150

Val His Pro Thr Thr Leu Asp Ser Ala Val Gln Ala Ala Tyr Thr Thr
        1155                1160                1165

Leu Pro Phe Ala Gly Ser Arg Ile Lys Ser Ala Met Val Pro Ala Arg
        1170                1175                1180

Val Gly Cys Met Lys Ile Ser Ser Arg Leu Ala Asp Leu Glu Ala Arg
1185                1190                1195                1200

Asp Met Leu Arg Ala Gln Ala Lys Met His Ser Gln Ser Pro Ser Ala
            1205                1210                1215

Leu Val Thr Asp Val Ala Val Phe Asp Glu Ala Asp Pro Val Gly Gly
        1220                1225                1230

Pro Val Met Glu Leu Glu Gly Leu Val Phe Gln Ser Leu Gly Ala Ser
        1235                1240                1245

Leu Gly Thr Ser Asp Arg Asp Ser Thr Asp Pro Gly Asn Thr Cys Ser
1250                1255                1260

Ser Trp His Trp Ala Pro Asp Ile Ser Leu Val Asn Pro Gly Trp Leu
1265                1270                1275                1280

Glu Lys Thr Leu Gly Thr Gly Ile Gln Glu His Glu Ile Ser Leu Ile
            1285                1290                1295

Leu Glu Leu Arg Arg Cys Ser Val His Phe Ile Gln Glu Ala Met Glu
        1300                1305                1310

Ser Leu Ser Val Gly Asp Val Glu Arg Leu Ser Gly His Leu Ala Lys
            1315                1320                1325

Phe Tyr Ala Trp Met Gln Lys Gln Leu Ala Cys Ala Gln Asn Gly Glu
    1330                1335                1340

Leu Gly Pro Glu Ser Ser Ser Trp Thr Arg Asp Ser Glu Gln Ala Arg
1345                1350                1355                1360

Cys Ser Leu Arg Ser Arg Val Val Ala Gly Ser Thr Asn Gly Glu Met
            1365                1370                1375

Ile Cys Arg Leu Gly Ser Val Leu Pro Ala Ile Leu Arg Arg Glu Val
            1380                1385                1390

Asp Pro Leu Glu Val Met Met Asp Gly His Leu Leu Ser Arg Tyr Tyr
        1395                1400                1405

Val Asp Ala Leu Lys Trp Ser Arg Ser Asn Ala Gln Ala Ser Glu Leu
    1410                1415                1420

Val Arg Leu Cys Cys His Lys Asn Pro Arg Ala Arg Ile Leu Glu Ile
1425                1430                1435                1440

Gly Gly Gly Thr Gly Gly Cys Thr Gln Leu Val Val Asp Ser Leu Gly
            1445                1450                1455

Pro Asn Pro Pro Val Gly Arg Tyr Asp Phe Thr Asp Val Ser Ala Gly
        1460                1465                1470
```

-continued

```
Phe Phe Glu Ala Ala Arg Lys Arg Phe Ala Gly Trp Gln Asn Val Met
    1475                1480                1485

Asp Phe Arg Lys Leu Asp Ile Glu Asp Asp Pro Glu Ala Gln Gly Phe
    1490                1495                1500

Val Cys Gly Ser Tyr Asp Val Val Leu Ala Cys Gln Val Leu His Ala
1505                1510                1515                1520

Thr Ser Asn Met Gln Arg Thr Leu Thr Asn Val Arg Lys Leu Leu Lys
        1525                1530                1535

Pro Gly Gly Lys Leu Ile Leu Val Glu Thr Thr Arg Asp Glu Leu Asp
            1540                1545                1550

Leu Phe Phe Thr Phe Gly Leu Leu Pro Gly Trp Trp Leu Ser Glu Glu
        1555                1560                1565

Pro Glu Arg Gln Ser Thr Pro Ser Leu Ser Pro Thr Met Trp Arg Ser
    1570                1575                1580

Met Leu His Thr Thr Gly Phe Asn Gly Val Glu Val Glu Ala Arg Asp
1585                1590                1595                1600

Cys Asp Ser His Glu Phe Tyr Met Ile Ser Thr Met Ser Thr Ala
            1605                1610                1615

Val Gln Ala Thr Pro Met Ser Cys Ser Val Lys Leu Pro Glu Val Leu
        1620                1625                1630

Leu Val Tyr Val Asp Ser Ser Thr Pro Met Ser Trp Ile Ser Asp Leu
        1635                1640                1645

Gln Gly Glu Ile Arg Gly Arg Asn Cys Ser Val Thr Ser Leu Gln Ala
        1650                1655                1660

Leu Arg Gln Val Pro Pro Thr Glu Gly Gln Ile Cys Val Phe Leu Gly
1665                1670                1675                1680

Glu Val Glu His Ser Met Leu Gly Ser Val Thr Asn Asp Asp Phe Thr
            1685                1690                1695

Leu Leu Thr Ser Met Leu Gln Leu Ala Gly Gly Thr Leu Trp Val Thr
        1700                1705                1710

Gln Gly Ala Thr Met Lys Ser Asp Asp Pro Leu Lys Ala Leu His Leu
        1715                1720                1725

Gly Leu Leu Arg Thr Met Arg Asn Glu Ser His Gly Lys Arg Phe Val
    1730                1735                1740

Ser Leu Asp Leu Asp Pro Ser Arg Asn Pro Trp Thr Gly Asp Ser Arg
1745                1750                1755                1760

Asp Ala Ile Val Ser Val Leu Asp Leu Ile Ser Met Ser Asp Glu Lys
            1765                1770                1775

Glu Phe Asp Tyr Ala Glu Arg Asp Gly Val Ile His Val Pro Arg Ala
        1780                1785                1790

Phe Ser Asp Ser Ile Asn Gly Gly Glu Glu Asp Gly Tyr Ala Leu Glu
        1795                1800                1805

Pro Phe Gln Asp Ser Gln His Leu Leu Arg Leu Asp Ile Gln Thr Pro
    1810                1815                1820

Gly Leu Leu Asp Ser Leu His Phe Thr Lys Arg Asn Val Asp Thr Tyr
1825                1830                1835                1840

Glu Pro Asp Lys Leu Pro Asp Asp Trp Val Glu Ile Glu Pro Arg Ala
            1845                1850                1855

Phe Gly Leu Asn Phe Arg Asp Ile Met Val Ala Met Gly Gln Leu Glu
        1860                1865                1870

Ser Asn Val Met Gly Phe Glu Cys Ala Gly Val Val Thr Ser Leu Ser
        1875                1880                1885
```

-continued

```
Glu Thr Ala Arg Thr Ile Ala Pro Gly Leu Ala Val Gly Asp Arg Val
    1890                1895                1900
Cys Ala Leu Met Asn Gly His Trp Ala Ser Arg Val Thr Thr Ser Arg
1905                1910                1915                1920
Thr Asn Val Val Arg Ile Pro Glu Thr Leu Ser Phe Pro His Ala Ala
            1925                1930                1935
Ser Ile Pro Leu Ala Phe Thr Thr Ala Tyr Ile Ser Leu Tyr Thr Val
        1940                1945                1950
Ala Arg Ile Leu Pro Gly Glu Thr Val Leu Ile His Ala Gly Ala Gly
    1955                1960                1965
Gly Val Gly Gln Ala Ala Ile Ile Leu Ala Gln Leu Thr Gly Ala Glu
    1970                1975                1980
Val Phe Thr Thr Ala Gly Ser Glu Thr Lys Arg Asn Leu Leu Ile Asp
1985                1990                1995                2000
Lys Phe His Leu Asp Pro Asp His Val Phe Ser Ser Arg Asp Ser Ser
            2005                2010                2015
Phe Val Asp Gly Ile Lys Thr Arg Thr Arg Gly Lys Gly Val Asp Val
        2020                2025                2030
Val Leu Asn Ser Leu Ala Gly Pro Leu Leu Gln Lys Ser Phe Asp Cys
    2035                2040                2045
Leu Ala Arg Phe Gly Arg Phe Val Glu Ile Gly Lys Lys Asp Leu Glu
    2050                2055                2060
Gln Asn Ser Arg Leu Asp Met Ser Thr Phe Val Arg Asn Val Ser Phe
2065                2070                2075                2080
Ser Ser Val Asp Ile Leu Tyr Trp Gln Gln Ala Lys Pro Ala Glu Ile
            2085                2090                2095
Phe Gln Ala Met Ser Glu Val Ile Leu Leu Trp Glu Arg Thr Ala Ile
        2100                2105                2110
Gly Leu Ile His Pro Ile Ser Glu Tyr Pro Met Ser Ala Leu Glu Lys
    2115                2120                2125
Ala Phe Arg Thr Met Gln Ser Gly Gln His Val Gly Lys Ile Val Val
    2130                2135                2140
Thr Val Ala Pro Asp Asp Ala Val Leu Val Arg Gln Glu Arg Met Pro
2145                2150                2155                2160
Leu Phe Leu Lys Pro Asn Val Ser Tyr Leu Val Ala Gly Gly Leu Gly
            2165                2170                2175
Gly Ile Gly Arg Arg Ile Cys Glu Trp Leu Val Asp Arg Gly Ala Arg
        2180                2185                2190
Tyr Leu Ile Ile Leu Ser Arg Thr Ala Arg Val Asp Pro Val Val Thr
    2195                2200                2205
Ser Leu Gln Glu Arg Gly Cys Thr Val Ser Val Gln Ala Cys Asp Val
    2210                2215                2220
Ala Asp Glu Ser Gln Leu Glu Ala Ala Leu Gln Gln Cys Arg Ala Glu
2225                2230                2235                2240
Glu Met Pro Pro Ile Arg Gly Val Ile Gln Gly Ala Met Val Leu Lys
            2245                2250                2255
Asp Ala Leu Val Ser Gln Met Thr Ala Asp Gly Phe His Ala Ala Leu
        2260                2265                2270
Arg Pro Lys Val Gln Gly Ser Trp Asn Leu His Arg Ile Ala Ser Asp
    2275                2280                2285
Val Asp Phe Phe Val Met Leu Ser Ser Leu Val Gly Val Met Gly Gly
    2290                2295                2300
```

-continued

```
Ala Gly Gln Ala Asn Tyr Ala Ala Ala Gly Ala Phe Gln Asp Ala Leu
2305                2310                2315                2320

Ala Glu His Arg Met Ala His Asn Gln Pro Ala Val Thr Ile Asp Leu
            2325                2330                2335

Gly Met Val Gln Ser Ile Gly Tyr Val Ala Glu Thr Asp Ser Ala Val
        2340                2345                2350

Ala Glu Arg Leu Gln Arg Ile Gly Tyr Gln Pro Leu His Glu Glu
    2355                2360                2365

Val Leu Asp Val Leu Glu Gln Ala Ile Ser Pro Val Cys Ser Pro Ala
    2370                2375                2380

Ala Pro Thr Arg Pro Ala Val Ile Val Thr Gly Ile Asn Thr Arg Pro
2385                2390                2395                2400

Gly Pro His Trp Ala His Ala Asp Trp Met Gln Glu Ala Arg Phe Ala
            2405                2410                2415

Gly Ile Lys Tyr Arg Asp Pro Leu Arg Asp Asn His Gly Ala Leu Ser
        2420                2425                2430

Leu Thr Pro Ala Glu Asp Asp Asn Leu His Ala Arg Leu Asn Arg Ala
    2435                2440                2445

Ile Ser Gln Gln Glu Ser Ile Ala Val Ile Met Glu Ala Met Ser Cys
    2450                2455                2460

Lys Leu Ile Ser Met Phe Gly Leu Thr Asp Ser Glu Met Ser Ala Thr
2465                2470                2475                2480

Gln Thr Leu Ala Gly Ile Gly Val Asp Ser Leu Val Ala Ile Glu Leu
            2485                2490                2495

Arg Asn Trp Ile Thr Ala Lys Phe Asn Val Asp Ile Ser Val Phe Glu
        2500                2505                2510

Leu Met Glu Gly Arg Thr Ile Ala Lys Val Ala Glu Val Val Leu Gln
    2515                2520                2525

Arg Tyr Lys Ala
    2530

<210> SEQ ID NO 11
<211> LENGTH: 249
<212> TYPE: PRT
<213> ORGANISM: Aspergillus terreus

<400> SEQUENCE: 11

Met Ala Thr Gln Glu Phe Leu Ser Asp Val Ser Ser Gly Phe Leu Ser
1               5                   10                  15

Ala Glu Ala Ile Arg Tyr Arg Val Lys Thr Gly Val Ser Met Asp Gly
            20                  25                  30

Trp Met Lys Arg Gly Tyr Ser Cys Asn Ser Val Arg Thr Asp Asp Lys
        35                  40                  45

His His Leu Arg His Leu Thr Asn Ile Gly Leu Asp Thr Pro Pro Cys
    50                  55                  60

Pro Lys Ser Leu Pro Ala Ala His Ser Ala Val Ala Ser Cys Leu Thr
65                  70                  75                  80

Phe Val Pro Pro Asp Pro Cys Glu Asn Trp Glu Ala Leu Gln Val Ala
            85                  90                  95

Trp Asp Lys Ala Cys Cys Arg Asn Pro Thr Pro Leu Phe Phe Ile Cys
            100                 105                 110

Val Ser Leu Leu Phe Ser Phe Tyr Ser Leu Trp Leu Gln Arg Gly Gly
        115                 120                 125

Cys Gly Arg Tyr Gly Gly Leu His Arg Val Ser Lys Val Phe Pro Lys
    130                 135                 140
```

```
Val Trp Pro Asp Asp Met Asp Ser Gln Leu Pro Ser Arg Leu Gln Thr
145                 150                 155                 160

Leu Val Ser Lys Arg Lys Pro Glu Pro Ala Pro Asn Asn Ser Thr Tyr
                165                 170                 175

Ile Ser Lys Gly Tyr Ala Thr Phe Phe Asn Gln Phe Ser Leu Pro Ser
            180                 185                 190

Val Asp Val Thr Gln Ile Leu Asn Gln Thr Leu Gln His His Asp Val
        195                 200                 205

Glu Thr Ile Asn Leu Asp Cys Gly Ser Gly Leu Leu Thr Leu Arg Thr
    210                 215                 220

Gln Leu Arg Ile Leu Leu Ile Gly Lys Pro Lys Ile Ile Lys Pro Phe
225                 230                 235                 240

Ser Gly Leu Arg Thr Ser Ile Asn Glu
                245

<210> SEQ ID NO 12
<211> LENGTH: 742
<212> TYPE: PRT
<213> ORGANISM: Aspergillus terreus

<400> SEQUENCE: 12

Met Glu Ser Ala Glu Leu Ser Ser Lys Arg Gln Ala Phe Pro Ala Cys
1               5                   10                  15

Asp Glu Cys Arg Ile Arg Lys Val Arg Cys Ser Lys Glu Gly Pro Lys
                20                  25                  30

Cys Ser His Cys Leu Arg Tyr Asn Leu Pro Cys Glu Phe Ser Asn Lys
            35                  40                  45

Val Ala Arg Asp Val Glu Lys Leu Gly Ser Arg Val Gly Asp Ile Glu
        50                  55                  60

His Ala Leu Gln Arg Cys Leu Ser Phe Ile Asp Ala His Gln Gly Phe
65                  70                  75                  80

Arg Asp Leu Ser Arg Pro Gln Ser Gln Glu Ser Gly Tyr Thr Ser Ser
                85                  90                  95

Thr Ser Ser Glu Glu Cys Glu Val Asn Leu Tyr Ser Gly Lys His Thr
            100                 105                 110

Ser Pro Thr Glu Glu Asp Gly Phe Trp Pro Leu His Gly Tyr Gly Ser
        115                 120                 125

Phe Val Ser Leu Val Met Glu Ala Gln Ala Ala Asn Ala Asn Leu Thr
130                 135                 140

Ser Trp Leu Pro Val Asp Met Thr Ser Gly Gln Val Ala Glu Met Val
145                 150                 155                 160

Ala Phe Asp Arg Gln Ala Val Ser Ala Val Arg Ser Lys Val Ala Glu
                165                 170                 175

Ala Asn Glu Thr Leu Gln Gln Ile Ile Glu Asp Ile Pro Thr Leu Ser
            180                 185                 190

Ala Ser Glu Asn Asp Thr Phe Leu Pro Ser Leu Pro Pro Arg Ala Leu
        195                 200                 205

Val Glu Pro Ser Ile Asn Glu Tyr Phe Lys Lys Leu His Pro Arg Leu
    210                 215                 220

Pro Ile Phe Ser Arg Gln Thr Ile Met Asp Ala Val Glu Ser Gln Tyr
225                 230                 235                 240

Thr Ile Arg Thr Gly Pro Pro Asp Leu Val Trp Ile Thr Ser Phe Asn
                245                 250                 255

Cys Ile Val Leu Gln Ala Leu Thr Gln Thr Ser Ile Ala Asn Lys Val
            260                 265                 270
```

-continued

```
Val Gly Cys Thr Gly Gln Asp Ile Pro Ile Asp Tyr Met Ile Ile Ser
        275                 280                 285
Leu Leu Arg Asn Ile Arg Gln Cys Tyr Asn Arg Leu Glu Thr Leu Val
        290                 295                 300
Lys Pro Arg Leu Ser Asn Ile Arg Ala Leu Phe Cys Leu Ala Leu Val
305                 310                 315                 320
Ala Met Glu Tyr Phe Asp Phe Ala Ile Phe Leu Thr Ile Phe Ala Gln
                325                 330                 335
Val Cys Glu Leu Ser Arg Leu Ile Gly Leu His Leu Thr Thr Thr Thr
        340                 345                 350
Pro Pro Thr Glu Asp Gly Ala Val Gly Asp Gln Pro Lys Asp Leu Phe
        355                 360                 365
Trp Ser Ile Phe Leu Val Asp Lys His Val Ser Ile Ile Gly Gly Lys
    370                 375                 380
Ala Cys Leu Leu Pro Ser Tyr Asp Cys Ser Val Pro Leu Pro Pro Tyr
385                 390                 395                 400
Asp Ser Ala Ala Pro Leu Pro Asn Ala Phe Ala Ala Arg Ile Arg Leu
                405                 410                 415
Ala Phe Ile Leu Glu Glu Ile Tyr Leu Gly Leu Tyr Ser Ala Lys Ser
        420                 425                 430
Ser Lys Met Glu Gln Ser Arg Val Arg Arg Ile Arg Arg Ile Ala
        435                 440                 445
Arg Lys Leu Ser Gln Trp His Val Gln His Glu His Val Leu Arg Thr
        450                 455                 460
Gly Asp Pro Asn Arg Pro Leu Glu Glu Tyr Ile Cys Ala Thr Gln Leu
465                 470                 475                 480
Arg Phe Ala Leu Ser Ser Cys Trp Val Leu Leu His Lys Arg Ile Trp
                485                 490                 495
Ser Gln Glu Arg Gly Ala Val Cys Leu Gln His Ala Arg Asp Cys Leu
            500                 505                 510
Met Leu Phe Lys Gln Leu Cys Asp Gly Cys Lys Ser Gly Phe Ser Asn
        515                 520                 525
Phe Asp Ser Ile Val Leu Asn Tyr Ser Leu Ile Ser Phe Met Gly Ile
        530                 535                 540
Tyr Val His Ile Val Glu Glu Asp Gln Pro Ile His Ser Gln Asp Met
545                 550                 555                 560
Glu Ile Leu Thr Phe Phe Ala Ile Tyr Thr Asn Arg Ser Ala Ser Asn
                565                 570                 575
Arg Ser Ser Ala Ser Ile Ser Tyr Lys Leu Ser Gln Val Ala Ser Arg
            580                 585                 590
Cys Ser Asp Ile Ala Leu Leu Leu Gln Asn Leu Arg Glu Arg Arg Phe
        595                 600                 605
Ile Pro Thr Thr Ile Ser Arg Ser Pro Thr Pro Ser Trp Asn Glu Pro
        610                 615                 620
Thr Tyr Met Asp Tyr Asp Val Ala Asn Ala Ser Thr Ser Thr Thr Ser
625                 630                 635                 640
Thr Gly Ser Ser Tyr Asn Leu Asn Ile Ser Pro Leu Gly Val Pro Gly
                645                 650                 655
Asp Gly Gln Val Trp Asp Ile Tyr Phe Asn Pro Arg Glu Ile Pro Met
            660                 665                 670
Asp Gly Thr Ile Ala Thr Pro Ser Glu Asp Ala Thr Gln Asp Leu Leu
        675                 680                 685
```

-continued

```
Ser Asn Asp Ala Gly Gln Cys Leu Gly Phe Pro Asp Phe Ser Leu Gly
    690                 695                 700
Ile Asp Asn Phe Ser Asp Phe Pro Leu Gly Ile Asp Met Thr Ser Gln
705                 710                 715                 720
Ser Glu Phe Gly Leu Ile Met Glu Glu Asp Ile Ile Arg Tyr Glu Arg
                725                 730                 735
Leu Leu Asp Arg Pro Val
            740
```

<210> SEQ ID NO 13
<211> LENGTH: 301
<212> TYPE: PRT
<213> ORGANISM: Aspergillus terreus

<400> SEQUENCE: 13

```
Met Glu Ser Lys Val Gln Thr Asn Val Pro Leu Pro Lys Ala Pro Leu
  1               5                  10                  15
Thr Gln Lys Ala Arg Gly Lys Arg Thr Lys Gly Ile Pro Ala Leu Val
                 20                  25                  30
Ala Gly Ala Cys Ala Gly Ala Val Glu Ile Ser Ile Thr Tyr Pro Phe
             35                  40                  45
Glu Ser Ala Lys Thr Arg Ala Gln Leu Lys Arg Arg Asn His Asp Val
         50                  55                  60
Ala Ala Ile Lys Pro Gly Ile Arg Gly Trp Tyr Ala Gly Tyr Gly Ala
 65                  70                  75                  80
Thr Leu Val Gly Thr Thr Leu Lys Ala Ser Val Gln Phe Ala Ser Phe
                 85                  90                  95
Asn Ile Tyr Arg Ser Ala Leu Ser Gly Pro Asn Gly Glu Leu Ser Thr
                100                 105                 110
Gly Ala Ser Val Leu Ala Gly Phe Gly Ala Gly Val Thr Glu Ala Val
            115                 120                 125
Leu Ala Val Thr Pro Ala Glu Ala Ile Lys Thr Lys Ile Ile Asp Ala
        130                 135                 140
Arg Lys Val Gly Asn Ala Glu Leu Ser Thr Thr Phe Gly Ala Ile Ala
145                 150                 155                 160
Gly Ile Leu Arg Asp Arg Gly Pro Leu Gly Phe Phe Ser Ala Val Gly
                165                 170                 175
Pro Thr Ile Leu Arg Gln Ser Ser Asn Ala Ala Val Lys Phe Thr Val
            180                 185                 190
Tyr Asn Glu Leu Ile Gly Leu Ala Arg Lys Tyr Ser Lys Asn Gly Glu
        195                 200                 205
Asp Val His Pro Leu Ala Ser Thr Leu Val Gly Ser Val Thr Gly Val
    210                 215                 220
Cys Cys Ala Trp Ser Thr Gln Pro Leu Asp Val Ile Lys Thr Arg Met
225                 230                 235                 240
Gln Ser Leu Gln Ala Arg Gln Leu Tyr Gly Asn Thr Phe Asn Cys Val
                245                 250                 255
Lys Thr Leu Leu Arg Asn Glu Gly Ile Gly Val Phe Trp Ser Gly Val
            260                 265                 270
Trp Phe Arg Thr Gly Arg Leu Ser Leu Thr Ser Ala Ile Met Phe Pro
        275                 280                 285
Val Tyr Glu Lys Val Tyr Lys Phe Leu Thr Gln Pro Asn
    290                 295                 300
```

-continued

<210> SEQ ID NO 14
<211> LENGTH: 490
<212> TYPE: PRT
<213> ORGANISM: Aspergillus terreus

<400> SEQUENCE: 14

```
Met Thr Lys Gln Ser Ala Asp Ser Asn Ala Lys Ser Gly Val Thr Ala
  1               5                  10                  15

Glu Ile Cys His Trp Ala Ser Asn Leu Ala Thr Asp Asp Ile Pro Pro
             20                  25                  30

Asp Val Leu Glu Arg Ala Lys Tyr Leu Ile Leu Asp Gly Ile Ala Cys
         35                  40                  45

Ala Trp Val Gly Ala Arg Val Pro Trp Ser Glu Lys Tyr Val Gln Ala
     50                  55                  60

Thr Met Ser Phe Glu Pro Pro Gly Ala Cys Arg Val Ile Gly Tyr Gly
 65                  70                  75                  80

Gln Lys Leu Gly Pro Val Ala Ala Met Thr Asn Ser Ala Phe Ile
             85                  90                  95

Gln Ala Thr Glu Leu Asp Asp Tyr His Ser Glu Ala Pro Leu His Ser
        100                 105                 110

Ala Ser Ile Val Leu Pro Ala Val Phe Ala Ala Ser Glu Val Leu Ala
    115                 120                 125

Glu Gln Gly Lys Thr Ile Ser Gly Ile Ala Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
    275                 280                 285

Leu Tyr Ala Cys Cys Gly Leu Val His Gly Pro Val Glu Ala Ile Glu
    290                 295                 300

Asn Leu Gln Arg Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
    355                 360                 365

Leu Leu Ala Gln Phe Ser Glu Phe Asp Asp Asn Leu Glu Arg Pro Glu
370                 375                 380
```

```
Val Trp Asp Leu Ala Arg Lys Val Thr Pro Ser His Ser Glu Glu Phe
385                 390                 395                 400

Asp Gln Asp Gly Asn Cys Leu Ser Ala Gly Arg Val Arg Ile Glu Phe
            405                 410                 415

Asn Asp Gly Ser Ser Val Thr Glu Thr Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Thr Arg Val Lys Glu Ile Glu Asp Leu
    450                 455                 460

Val Leu Ser Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 15
<211> LENGTH: 488
<212> TYPE: PRT
<213> ORGANISM: Aspergillus terreus

<400> SEQUENCE: 15

Met Gly Arg Gly Asp Thr Glu Ser Pro Asn Pro Ala Thr Thr Ser Glu
1               5                   10                  15

Gly Ser Gly Gln Asn Glu Pro Glu Lys Lys Gly Arg Asp Ile Pro Leu
            20                  25                  30

Trp Arg Lys Cys Val Ile Thr Phe Val Ser Trp Met Thr Leu Val
        35                  40                  45

Val Thr Phe Ser Ser Thr Cys Leu Leu Pro Ala Ala Pro Glu Ile Ala
    50                  55                  60

Asn Glu Phe Asp Met Thr Val Glu Thr Ile Asn Ile Ser Asn Ala Gly
65                  70                  75                  80

Val Leu Val Ala Met Gly Tyr Ser Ser Leu Ile Trp Gly Pro Met Asn
                85                  90                  95

Lys Leu Val Gly Arg Arg Thr Ser Tyr Asn Leu Ala Ile Ser Met Leu
            100                 105                 110

Cys Ala Cys Ser Ala Gly Thr Ala Ala Ile Asn Glu Lys Met Phe
        115                 120                 125

Ile Ala Phe Arg Val Leu Ser Gly Leu Thr Gly Thr Ser Phe Met Val
130                 135                 140

Ser Gly Gln Thr Val Leu Ala Asp Ile Phe Glu Pro Val Tyr Arg Gly
145                 150                 155                 160

Thr Ala Val Gly Phe Phe Met Ala Gly Thr Leu Ser Gly Pro Ala Ile
                165                 170                 175

Gly Pro Cys Val Gly Gly Val Ile Val Thr Phe Thr Ser Trp Arg Val
            180                 185                 190

Ile Phe Trp Leu Gln Leu Gly Met Ser Gly Leu Gly Leu Val Leu Ser
        195                 200                 205

Leu Leu Phe Phe Pro Lys Ile Glu Gly Thr Ser Glu Lys Val Ser Thr
    210                 215                 220

Ala Phe Lys Pro Thr Thr Leu Val Ser Ile Ile Ser Lys Phe Ser Pro
225                 230                 235                 240

Thr Asp Val Leu Lys Gln Trp Val Tyr Pro Asn Val Phe Leu Ala Val
                245                 250                 255

Ser Ala Trp Glu Ile Cys Pro Leu His Leu Leu Glu Thr Lys Cys Ser
            260                 265                 270
```

```
Cys Arg Lys Gln Lys Asp Leu Cys Cys Gly Leu Leu Ala Ile Thr Gln
            275                 280                 285

Tyr Ser Ile Leu Thr Ser Ala Arg Ala Ile Phe Asn Ser Arg Phe His
        290                 295                 300

Leu Thr Thr Ala Leu Val Ser Gly Leu Phe Tyr Leu Ala Pro Gly Ala
305                 310                 315                 320

Gly Phe Leu Ile Gly Ser Leu Val Gly Gly Lys Leu Ser Asp Arg Thr
                325                 330                 335

Val Arg Arg Tyr Ile Val Lys Arg Gly Phe Arg Leu Pro Gln Asp Arg
                340                 345                 350

Leu His Ser Gly Leu Ile Thr Leu Phe Ala Val Leu Pro Ala Gly Thr
            355                 360                 365

Leu Ile Tyr Gly Trp Thr Leu Gln Glu Asp Lys Gly Gly Met Val Val
        370                 375                 380

Pro Ile Ile Ala Ala Phe Phe Ala Gly Trp Gly Leu Met Gly Ser Phe
385                 390                 395                 400

Asn Cys Leu Asn Thr Tyr Val Ala Val Glu Ala Leu Pro Arg Asn Arg
                405                 410                 415

Ser Ala Val Ile Ala Gly Lys Tyr Met Ile Gln Tyr Ser Phe Ser Ala
                420                 425                 430

Gly Ser Ser Ala Leu Val Val Pro Val Ile Asp Ala Leu Gly Val Gly
            435                 440                 445

Trp Thr Phe Thr Leu Cys Val Ala Ser Thr Ile Ala Gly Leu Ile
        450                 455                 460

Thr Ala Ala Ile Ala Arg Trp Gly Ile Asn Met Gln Arg Trp Ala Glu
465                 470                 475                 480

Arg Ala Phe Asn Leu Pro Thr Gln
                485

<210> SEQ ID NO 16
<211> LENGTH: 516
<212> TYPE: PRT
<213> ORGANISM: Aspergillus terreus

<400> SEQUENCE: 16

Met Thr Leu Gln Ile Ile Val Ile Ala Ala Thr Ala Val Ile Tyr Phe
  1               5                  10                  15

Leu Thr Arg Tyr Phe Asn Arg Thr Asp Ile Pro Lys Ile Lys Gly Ile
                 20                  25                  30

Pro Glu Ile Pro Gly Val Pro Ile Phe Gly Asn Leu Ile Gln Leu Gly
             35                  40                  45

Val Lys His Ala Thr Val Ala Arg Lys Trp Ser Lys Glu Phe Gly Pro
         50                  55                  60

Val Phe Gln Ala Arg Leu Gly Asn Arg Arg Val Ile Phe Ala Asn Thr
 65                  70                  75                  80

Phe Glu Ser Thr Arg Gln Leu Trp Ile Lys Glu Gln Ser Ser Met Ile
                 85                  90                  95

Ser Arg Pro Thr Phe His Thr Phe His Gly Val Ser Ser Ser Gln
            100                 105                 110

Gly Phe Thr Ile Gly Thr Ser Pro Trp Asp Glu Ser Cys Lys Arg Arg
            115                 120                 125

Arg Lys Ala Ala Ala Thr Ala Leu Asn Arg Val Ala Val Gln Ser Tyr
        130                 135                 140

Met Pro Ile Ile Asp Leu Glu Ser Met Ala Ser Ile Lys Glu Leu Leu
145                 150                 155                 160
```

```
Lys Asp Ser Gln Gly Gly Lys Ile Asp Ile Asn Pro Thr Pro Tyr Phe
                165                 170                 175

Gln Arg Phe Ala Leu Asn Thr Ser Leu Thr Leu Asn Tyr Gly Tyr Arg
            180                 185                 190

Ile Glu Gly Asn Val Asn Asp Gln Leu Leu Arg Glu Ile Cys Glu Val
        195                 200                 205

Gln Arg Gly Val Ala Asn Leu Arg Ser Thr Ser Asn Asn Trp Gln Asp
    210                 215                 220

Tyr Val Pro Leu Leu Arg Leu Phe Ser Asn Arg Ser Asn Gln Ala Lys
225                 230                 235                 240

His Leu Arg Ala Arg Arg Asp Lys Tyr Met Ala Phe Leu Phe Asp Ile
                245                 250                 255

Leu Lys Asp Arg Met Ala Lys Gly Thr Asp Lys Pro Cys Ile Thr Gly
            260                 265                 270

Asn Ile Leu Lys Asn Pro Glu Thr Lys Leu Thr Asp Ala Glu Ile Lys
        275                 280                 285

Ser Ile Cys Leu Thr Met Val Ser Ala Gly Leu Asp Thr Val Pro Gly
    290                 295                 300

Asn Leu Ile Met Gly Ile Ala Tyr Leu Ser Ser Glu Asp Gly Gln Arg
305                 310                 315                 320

Ile Gln Gln Lys Ala Tyr Glu Glu Ile Met Ser Val Tyr Pro Asn Gly
                325                 330                 335

Asp Ala Trp Glu Arg Cys Leu Val Glu Glu Lys Val Pro Tyr Ile Thr
            340                 345                 350

Ala Leu Val Lys Glu Thr Leu Arg Phe Trp Thr Val Met Pro Ile Cys
        355                 360                 365

Ile Pro Arg Val Asn Ile Lys Glu Val Ile Tyr Asn Gly Ala Arg Ile
    370                 375                 380

Pro Ala Gly Thr Thr Phe Phe Met Asn Ala Trp Ala Ala Asn Tyr Asp
385                 390                 395                 400

Glu Asp His Phe Asp Met Pro Asn Arg Phe Leu Pro Glu Arg Tyr Leu
                405                 410                 415

Glu Pro Ser Glu Gly Phe Gly Thr Pro His Tyr Ser Phe Gly Ala Gly
            420                 425                 430

Thr Arg Met Cys Ala Ala Ser His Leu Ala Ser Arg Glu Leu Tyr Thr
        435                 440                 445

Val Phe Leu Arg Phe Ile Val Ala Phe Thr Ile Glu Pro Ala Gln Asn
    450                 455                 460

Pro Ala Asp Met Pro Val Leu Asp Ala Ile Glu Cys Asn Ala Thr Pro
465                 470                 475                 480

Thr Ser Met Thr Thr Glu Pro Lys Pro Phe Lys Val Gly Phe Lys Pro
                485                 490                 495

Arg Asp Glu Thr Ser Leu Arg Arg Trp Ile Ala Glu Ser Glu Glu Arg
            500                 505                 510

Thr Lys Glu Leu
        515

<210> SEQ ID NO 17
<211> LENGTH: 481
<212> TYPE: PRT
<213> ORGANISM: Aspergillus terreus

<400> SEQUENCE: 17

Met Lys Pro Ala Ile Leu Met Lys Tyr Trp Leu Phe Val Ser Ala Val
  1               5                  10                  15
```

```
Ser Ala Ser Thr Leu Asn Gly Lys Leu Thr Leu Ser Glu Thr Lys Val
        20                  25                  30

Thr Gly Ala Val Gln Leu Ala Cys Thr Asn Ser Pro Pro Asp Ile Tyr
        35                  40                  45

Ile Asp Pro Asp Ser Val Ser Val Arg Ala Ala His Asp Leu
 50                  55                  60

Ala Leu Asp Phe Gly Arg Val Phe Gly Lys Asn Ala Thr Val Arg Phe
 65                  70                  75                  80

Thr Asn Glu Thr His Pro Thr Ser Met Ala Ile Ala Gly Thr Ile
                85                  90                  95

Asp Lys Ser Thr Phe Leu Gln Arg Leu Ile Ala Asp His Lys Leu Asp
            100                 105                 110

Val Thr Ser Ile Arg Gly Gln Trp Glu Ser Tyr Ser Ser Ala Leu Val
            115                 120                 125

Leu Gly Pro Ala Lys Gly Ile Gln Asn Ala Leu Val Ile Ala Gly Ser
    130                 135                 140

Asp Arg Arg Gly Ala Ile Tyr Gly Leu Tyr Asp Ile Ser Glu Gln Ile
145                 150                 155                 160

Gly Val Ser Pro Leu Phe Trp Trp Thr Asp Val Thr Pro Thr Lys Leu
                165                 170                 175

Asp Ala Ile Tyr Ala Leu Asp Val Gln Lys Val Gln Gly Pro Pro Ser
            180                 185                 190

Val Lys Tyr Arg Gly Ile Phe Ile Asn Asp Glu Ala Pro Ala Leu His
    195                 200                 205

Asn Trp Ile Leu Ala Asn Tyr Gly Glu Val Glu Asn Gly Asp Pro Ala
210                 215                 220

Phe Ile Ser Arg Phe Tyr Ala His Val Phe Glu Leu Ile Leu Arg Leu
225                 230                 235                 240

Lys Gly Asn Tyr Leu Trp Pro Ala Met Trp Ser Asn Met Phe Tyr Val
                245                 250                 255

Asp Asp Thr Asn Asn Gly Pro Leu Ala Asp Tyr Tyr Gly Val Val Met
            260                 265                 270

Gly Thr Ser His Thr Gly Met Thr Val Gly Thr Pro Cys Leu Lys Ala
    275                 280                 285

His Ala Asp Tyr Glu Lys Glu Pro Met Ala Arg Ala Thr Asn Glu Gln
290                 295                 300

Ser Gln Phe Leu Asn Gly Thr Trp Asp Trp Ile Ser Asn Glu Val Asn
305                 310                 315                 320

Val Lys Ala Phe Met Arg Glu Gly Val Ile Arg Ser Gln His Trp Glu
                325                 330                 335

Thr Ala Tyr Thr Met Gly Met Arg Gly Leu Gly Asp Ala Ala Ser Pro
            340                 345                 350

Thr Leu Asn Ala Thr Val Glu Glu Ser Ile Val Ser Trp Gln Glu Ser
    355                 360                 365

Val Leu Ser Asp Ile Leu Asn Lys Thr Asn Leu Ser Asn Val Val Gln
370                 375                 380

Pro Phe Val Leu Phe Asp Glu Leu Gly Thr Tyr Tyr Glu Ser Gly Met
385                 390                 395                 400

Thr Val Pro Asp Gln Val Thr Leu Ile Tyr Pro Asp Asp Asn Ala Gly
                405                 410                 415

Asn Met Leu Arg Leu Pro Leu Gln Asn Glu Thr Gly Arg Ser Gly Gly
            420                 425                 430
```

| | | | | | | | | | | | | |
|---|---|---|---|---|---|---|---|---|---|---|---|---|
|Ala|Gly|Ile|Tyr|Tyr|His|Phe|Asp|Met|Asn|Ala|Pro|Pro Arg Cys Tyr|
| | |435| | | |440| | | |445| | |

Lys Trp Ile Asn Thr Ala Gln Leu Ile Arg Thr Trp Asp Gln Leu Arg
 450                 455                 460

Ala Ala Tyr Ser His Gly Ala Gln Thr Val Trp Val Ala Asn Ile Gly
465                 470                 475                 480

Asp

<210> SEQ ID NO 18
<211> LENGTH: 33000
<212> TYPE: DNA
<213> ORGANISM: Aspergillus terreus

<400> SEQUENCE: 18

```
tggattttct tcctgtaggc ccgtagctat gtaatctagc taaacagagc gcgtatttta      60
aatattagaa actgctcgcg tatcttatcc agagcgttag ctaggtaggt tacctggtct     120
gttttagcaa gctggacggc ctgcagggcg actaatattt aggctatttt tataagcccg     180
gaaagatagc ttatatagct ataaggcttt agaaagatct actgcttaat atctatttct     240
aaaataataa gaaatctaat aagagtactt ttaaagagat ctttcttaag agtatggtcg     300
agtaagataa ttaaaaatat taaacaggcc taattaagca gttctttagt ttgctgctgc     360
tgattaacgc gctacaatag tttaagatct tagctttaga ttaggagatt aactagctgc     420
cggctataaa ttttttatcta attaagcgcg gtaaactagg cagtatttag ctagtggcgg     480
agtaaaatta gctggttagt ccggctacta tggtaggcga agtaaataag acactgctag     540
atctagtagt actaacagta cgtcgctagc cgtagataga tctagattag ctggttttag     600
atccccggcc ggcggaagaa gatattaatc taaatttagt tgaatttatt aatccggccc     660
ttcttaatcg cgtaataggt ctaattaatt agttgctgga cgctagcagt aaattacttt     720
agtaaagatt tagctatagg attagaaaag ctgccgagta gggcgactgc ggtttaatct     780
taattataaa ggtattccgg ctattaaata agctctagct ataaggaaat tgtagttaga     840
tgtagattaa taatagagat ctagtcgtta gtcctatccg cggtagccta atttttttat     900
aaagcctgct cgacccgagc ctgaataatt atagctaagg tctttagaga cggctttc      960
tctagtcttt aattagaaga ggcctcggta tatattactt taaagaatta actagtagat    1020
tagctgataa agaagcgctg atagctaata atatactctg ttagtcgggc gcgaagccta    1080
gcttatattt aagtaatagt cttctaactc tattttcttc gtgccctatt ataattagta    1140
tagtttttaat tttaatatttt atttattgtc tgtcggcact aatagatata tttataatat    1200
aggcagctat aactacggta gactggaaga cctaaaatca gagagctact tagagggggg    1260
aaataaataa tctcctactt tagattaatt tagagctgct gaagtattac agttaaagca    1320
gcttgttaga gggccggaat agtggtatta gaataaaagc tataacgcgt ttggaggtag    1380
ataataaaag tagtagaaga aactatatac tagtaggaag gtgtagtata gatctagatc    1440
ttataggtta agttatagag aaagagctct attgttaatt ctaggctcta agagaaaagt    1500
acctagagag ttaagaataa aggaaaatag gtttctataa ggagctattt tcttttttaat    1560
atttattata tttttttaaag atatattaat ggcgcgtcgg atacacgtag taaaaagtaa    1620
attcgtgtct gctattgctt attcctgaag ataaatata gatataatct cgctaggtcc    1680
tcttttaaata agatagaacg gcggagctgt ctgttcgggg cacgcatgta aggcgacggg    1740
agcacggcga aatattaaat cttgaccaat tagcaggcga gaaaatggat cgaaggttgg    1800
```

-continued

```
gtgaacttgg gcctagggac taggcaacca ccaagagaca tcctggctac tatagtccct   1860
attggcaatg gcctgattcg ctcggtccaa gctctgcgcg atcaaactcg acgagttcgc   1920
cttgacgtgg accgcaacgt cacacatgaa aaccgcatag ggatccgggt cagatcccag   1980
cgcatcctgg cacgtatccg catcgggcag ctggatcgat ccggagttca taagcgcggt   2040
aatttcgtct gtctcggtcg cgttcgtgct ctcggctgtc gtgtctccaa caatcgcgat   2100
atcgggccat gcggatagga agaagtaagt gtttgggttg tcgggtgtcg gttcttgggt   2160
tccgggctcg caccagcggt ggccgtcaaa tcgcgcgtcc atatcgatgt aatggatctg   2220
ctccgtattc cgggcggtgt tgatgtcgga aatggtggat tggattaacg agttgagcat   2280
gcggacgagg tcgttgagtt ccttgcgtag gtcggtcgtg agccacacat agttgccgga   2340
ttgctgcggg tcgtagtgtg ggctttcgta ccagaaggtg gttgagtcgc agtcggtggt   2400
gtcttcgttg aagaaggtga catagccagg gacgtagagg ttgaacgact aaagtaaagt   2460
cagcgcgacg aaggacagca cgacaggaat aaataaggat aacagggaga tatacgctag   2520
agccagatct atccaggatc ttttcatacg cagccctaag tttcgagccg agtccgtcag   2580
accctgtatc ctgcatcagg ttgcgggctt tctcttcagt ctccagacac cactggcggt   2640
attgctcaag cgagtaccac cacattgtta gcacgcagtt ggaaaccaga tcgctgaaga   2700
acacatcgtt ccctccaatt gtcagggttg ccatggtagt ccccgtgggg tcctgtccta   2760
gccactggtc gatctttta ttcagcccaa ccgttgtatc tccagagcac gcatagttgg   2820
tataagtgaa atcctcagta tcaaaccact cctggacgag cttccgtag ctgttacttc   2880
ccacgcggca actgtcaccg gttgtggttc ctgtacccat cccagcggcg taggagtcac   2940
cgaagtgaac ataatcgttg acgccgtaca cagtgtcagc atcataagac gaatcatcgt   3000
aggccggaca gctggagtca tccgccgaag aagcagactc ctcaggaagg ggaatctgtc   3060
gaccacatat cttggtatag tacccgccaa gtacgacaag agcccatgaa tccgcattgt   3120
aggcggacaa cttgctgtca cagatgcctt cttgcccgag gttatttggg tctgggcaaa   3180
gcaatctgcg ttgccagtta gcatcgccgg ctatacggag ctcattagcg gctcttcag   3240
ccttctgcc tctttcgata cagtgtcgat tgaaggtccc tgcggcaaga tctcgagctc   3300
ctttccatcc atagacataa tcgcgggtcc tcctaaggtg aaagaatcag tatcggcctg   3360
ggaatgagaa aaaatatgtg ataccaccca ttctctccat tgacaatctc cataacatag   3420
tccgtatgcg ttacttcgtg caaaatcgcc ccggctcgag tgagatgggc atcatgaaga   3480
ttaattgagt cgcacctcgc gagcactgac ctggaactct tcaactcatc tgtgaagaac   3540
tttgggcaga aattaagccg attcctattg ttcatcatgg ccaaccagcc gttctcgtca   3600
cagccccgaa ggttttttgca agtgatcgtg aacttttcgt cgtcgaattg cgaagaccca   3660
gaaatcatgg tgaccatccg gtcgaacgta taccttacat ttatagtgaa ggtcaagctg   3720
tcggtgagtg attcggcaaa gaagatgtcc ctatatgggc cgtatgcgcc gccgctaaag   3780
tacgcaactt ccgaggcagc atcaagcgca tattgcattt cttcaaagag cgtctgcacc   3840
tgggccctag tgcactcgct gttgtcctga taatgagggg tgagctcgat gggggctttt   3900
acaggagata caggtagatt ggggttagtt atcgggccgt catcgcctgt gtggtctttg   3960
gtggcacatt cgttgtacca cgtctgcgct gtgttgttta tggagttcca gatgctgtgc   4020
atgtctgcac gaccgtcgcc gttcagatca gggaaataag tgcatgagcc ttcaaccgcc   4080
cctcggtact tgggacccctg cggtccccat tcgtatcgcg atcccttgat atcacgttgg   4140
ccaaggttgt accacaccga cccatctccc gagaacttgt ctgtccagat catatcggcc   4200
```

```
tttccgtcgc cgttgacgtc ggcccagtgt agattcgccc tgtccttctc ctcggagtac   4260
ttgaattgat caatgtagtc ccatccatcg tccccattga cccagcccca ggtgcggccg   4320
tccttctcaa cgcacagata atcggccttg ccgttgccag aaacatcagc aaaatggacc   4380
ggccggtcaa agaaaccaag gcctcggtgc tcggggcagt aaagctcatc tgcagcattg   4440
atattgtagt cccagtcaaa actccccgtg tctttgatct tgttccgcca aacttgggcc   4500
ctgttcagat tgtcgggatc cgtccagatt atatcgcagg ctccgtcgcc gtcccagtct   4560
gcgagatgca gatcgcgccg gtcaagcttc atgccaatct gctcttgggg gtcgaagata   4620
atctcattcg ccccccagaa gctcgacccg tcggcgggga cttcaaccag gcccctattc   4680
ggataaagac gcatatggcc ggttgaatgg atccaaatgt agtccatcat accattgtcg   4740
tggcccatca tattgcaata cctgtctccg tcggctataa caattagcaa tcaacctctc   4800
tatgagaact tccttccata cctttgatct tagcccctcc tgcgcccttg ctcttccaca   4860
catgaacgta atacagcggc ccaaaatact tgtcagaggt atccttcttg atgaacacat   4920
agtcctgtct cccgagctct ccaaaatccg ccacctcgcc atagagtcgc gcaaagtaga   4980
cctgatcccg taatccggat gtcccgaata ttactcccat tccgggatgc gacgggccag   5040
agttagcatc ttggtagaac ccctggcgcc acacgacgtt caacccgtca ccagactctc   5100 cttttgatgca gctccgggag ttggtgtatg ttgtcgtagc gccatcgtca tcaacccaca   5160
tccagtcgtc gcgcccgtcg ccgttgatat cctcgaatcg cacgccgcgc aggtctccca   5220
tgactttccc cgtgaagcgc ttgcccagcg gctgccagta tgcggggata tcttcgatcc   5280
atccatttcg ccagcatgtg acgtcgccgt tgtcagccaa accgcagtag tcggcgcggc   5340
cgtcgccgtc gatatcagca aggcgtacat gtgcctgatc gtatccttcg ggactcttcc   5400
atagtccgat atcggtgaag gatggaggct tgttgctctt ggcgtcgccg tctccattgt   5460
tgatgcttgc gtaggtggtc ccgtccaagg cgatgcagat gtagtcatca agtccgtcgc   5520
ctatcattta tcacacataa atcagtccca gatggttcct cggcagacag acacagtgct   5580
taccgttgat gtcgataaaa tgcacacccc ccggggttaca attattatga gtcgagaacg   5640 tcccccccctt cgtaaactcc tgctcctcag tgtggacatt attcgtgtaa gaaacaaacg   5700
tcaccgcgcc ggagtcctta tctttgtgga agatcatcat gtcatcatac gcctagtat    5760 aaagcctccc gaagaaaaag tgcagctcgt cgtcatcctt gtatggatcg gctgcaccct   5820
tcccggcgcg gacagtaaac aacgccccgc tatactcgct gtcgtgtcga tagattccgt   5880
catcctcacc actccctttgc tgcgtgaacc cgccagcgta gactccgctc ccgtactctt   5940
tgtcacaggt ccccgtggat gagatgtcaa ggtccgccgg cttgacaatg agctccgcca   6000
ccgcagcgtt gtagatcgcg ttataccaga tgtctgccat ctgggagtac ccgtagtcgt   6060
tggggtgctt gttatcggcg aagttatcgg ggtacgtgat ccagttgttt ccggggctgg   6120
gagccggcgg atccatatcg gccaggacga tggagacatt ctgcgcctcg cgcatgtcaa   6180
ggaccagctc gcggaactgc gcgttgacgg agggcctgtt agcttcgagg gttgtggaac   6240 ccgagggggat cagggtcgac aggacgatga gcgtgttggc catgtccggg gcgccgatta   6300
gggtttcgat cagggagcgc atgcgctcgc cggcgttcgc agggtcgacg ttgtagtcgc   6360
agtcgttggt gccggcgttg atcagcacga cgttcggctt gtaggcgagc gagtttgcgg   6420
ccgcggtttg cacttgcgtt atcacgtcgc cgctgtgggc ttctacatcc ttttcccgcg   6480
tttatatgtc aattggtctg tctatctgtc ggaggggtgg gggaagagag atgcatacat   6540
tgtctaccat gtcaccgttg gacttactgc ccaccatgtc cacctcccag ccttcaaagc   6600
```

```
gaagtttgtc acggagaggt ttgcgatatc catttccggt tgaggatagg tatccccagg   6660
tgatggatgc gccaagaggg aggatccgta gagggacttt cagggcatca tctcgttttg   6720
ctcttggacg ccattcagca gcgtcaaagt ctatatatct cgaatcgtct gtgggtcgcg   6780
agacagggac ggctgctcct gtggcagtag atgatagaag agccagtgtt agattgaaca   6840
ccgtaaagaa aagtgagagac gccattatcg atgctgactc tctgcacctt tcactcctct   6900
tccatactgc gagtcgcttt tatactttca cagccctcca gtcatttcat gtgtaagatg   6960
cctcggcgta tgtgccgttc tgaaacaagt gtacttccaa gaatcgcgag ctcgagtatg   7020
gtaccaggat aaacctggat acttaggtat caaagcatga gaccctggca ttttccatgg   7080
caagtttggg ggccataatc ctgtggcaga ggttcatatg cggcggtcga gtcatgcaat   7140
gggtttattt ggcgtagttt acggagcaac caatcactgg cctgaatatg gtaccaggat   7200
gaaccagaat agtaccaaag gatgagactg gcatccttca tagccataac tgttgggggt   7260
catcatctgt gacagggaga tatgcagtga ttgagtggtg caacgggctt aaatgtaatc   7320
ggtgtttgca actacgcgga gtgctaggga ggcggctgat tggcatgata agcaaaggct   7380
tagctgagac atggcactag gtagaggcta ggacctgcgt aagcattcat tccgatgctc   7440
tattggataa gttatttaca atctccgcat taggcggcaa tccttaatat agaatactag   7500
tatagagcac tatggacact ccgacgttca tttaatatct ccacccgtgt tacccctctt   7560
tctgcctttg atctctatca agctggccct tctggcattt atccttgcat taaacatgac   7620
tctaccaaca cttcctaact ggataaggat gtgcgtgcat ttgtccctta cacatctcca   7680
tcagcaccgt tccccgaaat acgagtctat acctattaaa agtatccagg ctaattcaca   7740
cagaatcctc atcatcctaa ccacagcctc cttctacccg cagatccggt gcatccaact   7800
tcgaaactcc acgcacggca tctccactgc ctacatcctc ttcaacctaa tcagcgcaac   7860
agaacacttc accatcctat tcgcattgct ggtaaacagc ggcggagatg tcctcatcca   7920 tgagccccc acgaccggcg acgggttgaa cctgtaccag cttttcgcag tgtggatggg   7980
atgcttagtc ctcttctgcc aagcaatcca tagcctccac gccaatccac gccgcaaact   8040
catcctacta accatataca ttcaataccct atgcatttct atcttaccag aggtcatcga   8100
cgcaatcacc actcccgagg aaacgagaaa acaaaggccg ccaacgggcg agaggaactg   8160
gctgatcgga ctctttcttt ccgcgcacgc gatgaccgtc ctgccactat cggccgtgct   8220
ccgcatcgcg ggattcatag atcagtcgcg actgatctcg cggcgcagac gggagcagcc   8280
atcggtctta agcctgacag gcctggcgtg tcaggccgtg gtctttgctc tagtttctgg   8340
actctgggta ctcagggttc agcagccgtt tcctcgaatg ccgatgagaa gacctgtgga   8400
ttggatgtat tggtaccatg taattgggtg gccggttgtc gacgatgcgg tttatgcgct   8460
gggacaatgg gttttgtttt ggtatgcggt ttgttggcgt tctcggggcg atgctaggga   8520
tgaagcagtc catgctgggg agactgatga cctgttagga gaggatgaag gcatgggta   8580 cggcggaacc gggacttctt agattgtctg tatatcattg tgccacgata tcgcgtgtaa   8640
caccatggtg tggaaggtat actcatcgcc atggattttt tgacaagctt gctataatag   8700
ctcttggtta actcttttgc cttttttttat tctgccatac ggtctcattc agagcacgat   8760
ctgcagggga aagagaacag ctataccgtc gcatgatttc aaccttccaa actcttatta   8820
tcaaactggt aatagcaccg tgaatgggat ggcttaggct ttagatgaag gagttagagc   8880
ctggctgcaa gccctaaaca cctgtctagt ccacgttata atttagcaag tctcccgagc   8940
tctcgcaagc ctaccactag cttatagtca atagattgtg gtatatccag gggccttta   9000
```

-continued

| | | | | | |
|---|---|---|---|---|---|
| agtatttacg | gctcatacaa | aaagtaatat | gagacagctc | tactcttttt | acatcatcta | 9060 |
| catctatcgc | ctagattggt | agctcgcagt | gggtcatccc | tatctgttac | cataagactt | 9120 |
| cccgtggtcg | caattcaacc | taatgcagga | ctttctcgtg | ggccgattta | ttactagacc | 9180 |
| tattgatctt | tgattgtggc | ttcatccggt | cgctattact | tacagccaca | gtgatcatag | 9240 |
| tattcgaatt | acaatgttga | acctctgcca | cgattactat | caggtccttc | tagttggacc | 9300 |
| tctctccacc | agcgttgaag | tataatcccg | tagactcaaa | aaccaacccg | acctgatcca | 9360 |
| ataccaagtc | taattataat | cagaaaaaaa | tattttaaaa | attaaaattt | atatagatat | 9420 |
| ctgctaatcc | tcgcagacta | tatataagaa | acccgtaatc | tgcgcggact | atagtagtat | 9480 |
| agattttagg | acccgctccg | cgcggagcgg | agcggactgt | ggatctgcgg | agagttagta | 9540 |
| tacaaaatac | tagaggcggc | gaggtcgagt | tagcgcagtc | tagtactaaa | taggaaagcg | 9600 |
| gttatttag | cgcgaaaaca | gggtactaat | atttttggac | ccccactgta | ccttcacgga | 9660 |
| tagtaccaca | caactacatt | acgattatat | atcatctttc | cccctcccat | ggttttccca | 9720 |
| agcaccttac | acgtggccgc | cctcaactac | ctagtttgtt | gacagaagtg | cagtaacagt | 9780 |
| gacctaactg | agtgtagttt | agagatatat | attctactat | aggggctaa | accgtggtgg | 9840 |
| attacgcaga | cttttgcta | aaagcataat | agctacgata | ggtagaatat | aactatagat | 9900 |
| aaggtagatt | agggtaggta | cgactgcggc | ggcttgatta | ttccttgaaa | atgacgggct | 9960 |
| cttctggggt | agactactgc | tatagtgaac | caggaaggcg | gatatcctcg | tcgcgccggc | 10020 |
| gcatcatgag | cttcgtggtg | ggatgaatgc | gcacgctgaa | agaatggcgg | tagtactgca | 10080 |
| acggttcgtc | ggggaccacc | ttccagtcgt | atcgtatgag | caagtaggct | aacatcatct | 10140 |
| tgatctcctt | agaggcaaag | aaccggccgg | ggcaagcccg | tggatgccaa | ccgaagccga | 10200 |
| tgtggtcccc | gttggtgttc | tccagttggg | cactgaacgc | tttagccggg | tcctctcgca | 10260 |
| ggcgcatata | ccgtaagga | tcgtattttg | ccggctctgg | ccagacctcg | gggttgctca | 10320 |
| tgcggtcggc | agctaccgcc | accagctctc | cttttgggat | aaaggttcca | ttggagaaag | 10380 |
| tcacatcctg | caatgcatag | ctgcgcatgg | tggcacattc | gacgggcttg | acgcgctgtg | 10440 |
| actccttgag | acaactatcc | agcagtttga | gcttgtacag | cgaggcaggt | gtccaacccc | 10500 |
| cttggccgat | gaccgtccgg | atctcatcac | ggagggctc | aaggagatgg | ggatgtcgga | 10560 |
| cgatgtccac | caacccaccg | atcagcaggt | cggaggttcc | gtagatacca | gcaaagtcca | 10620 |
| tggccagttg | cgcccggct | gcatcgtacc | atttcccctt | ggcagtatcc | tcgaaccact | 10680 |
| ggatcgagtc | tacgtagcga | ggcggctcaa | tgcccttgc | ccggcaggca | tctctttccg | 10740 |
| cacgtcgctc | ctggataatg | ggatcgagaa | gttgccgggc | tcgtcgaacc | tgcgcccgga | 10800 |
| gtttggctcc | ctgggctcg | agccaatgta | caaggggcg | cagaatgacg | ggccagaggc | 10860 |
| gcagctggcg | cgcttgaatt | gccatcgtca | ccgcgtggtg | cttggcgatg | tcaagccact | 10920 |
| cctcattatg | ggctaacttg | ctcccgacca | taataaagt | cactgttcgg | gtcactaagt | 10980 |
| ccagacactg | gttatagaca | ggcactgtgt | gccattctga | aagcaaaagc | acatccctct | 11040 |
| tcatcagcta | atggcctaaa | aacaaaaata | ctcatcatga | tcacttacca | ttgctgtcgc | 11100 |
| caaaatatc | cgtgataatc | ccgctggctt | cattgcaag | aggcttgacg | tacttgggag | 11160 |
| cttgggtctg | gaactggttc | ataaccacct | tggtgatgag | atgtgcatcc | ctcgtgactt | 11220 |
| ccttgaatcc | atcgaatccg | ggaagatgag | agtgaaagtc | ctgatgagag | cacgaagatc | 11280 |
| agtaagtcag | gtcctcacag | cggaagcagt | tgcaaagaac | ggtggactcc | ttaccgtgcc | 11340 |
| caagaacttg | tacatacaga | gctctttcat | cttgcgaaac | tcatcggcca | tagaggaggg | 11400 |

```
aagaatggtg cagtacccag agtcgactat gaaccgaatg ggcttatcat tttgcgagaa    11460
ccagctctca atccatgacg gtgcattcgc atcaaaatcc cgtttggccc tcatggtcgt    11520
cagttcccac catgttttcg gattgaacac cggcagatca gatctccggc cactcgagca    11580
caggtaaaga agaaggcata gtagccccgc actggtagtg accaagggcg caaaccacga    11640
gccatgttgc tgcgtgtcat tccaagccag cgacagaagg tggtgcggct gtgtgagcgc    11700
gtcgacagtc atggctagga gaccaggtgt ggttgaggga taagatatcg agagtgatgt    11760
gagcaaaaga tccgggaaag gtcgcgaagg aaagggcgtc tctcttacca agaaagtctg    11820
ttccctatca tgcaatcacc gcttgctgta cggtggtgat gatgctggga tggtggtggg    11880
tccccaccga ataacgccgg acagctgttg aagccgaatg acgccggcag gccaaaagaa    11940
ccctaccttc acttactcaa tcggcgcttc ccctcctatc accaaatcgg atgtaaatgg    12000
acgggcctta atagcgaccg gccgggccgg gaatccccaa acgtagatag ataggcatag    12060
acccgaaatc tttggcccgg catacatgag cacaggaagt tcacgcgac ggcgcctttc     12120 ctgcctcagc ttcaatccaa gctcacgagt tctgtcgcct ctatcagtcg tgcaattgtc    12180
ctactgcaaa cagcatggct caatctatgt atcctaatga gccattgtc gtggtcggca     12240 gtggttgtcg cttccctggt gacgccaaca caccctccaa gctctgggag ctactccagc    12300
atcctcgcga tgtgcagagt cgaatcccca agaacgatt tgacgtcgac acattttatc     12360
acccggacgg gaagcaccac gggcgaacaa atgcaccta cgcctatgtt ctccaagacg     12420
atctgggcgc cttcgatgcg gccttcttca atatccaggc tggagaggcc gagagtatgg    12480 accccagca ccggctgttg ctggagacgg tgtacgaggc cgtaacgaat gctggaatgc      12540
gtatccagga tctgcaggga acttcgactg ctgtttacgt cggggtgatg acgcacgact    12600
atgagactgt ctcaacccgc gacctggaga gcatccccac ctactcggcg acgggtgtcg    12660
cggtcagtgt tgcgtccaac cgcatctcgt atttttttga ctggcatgga ccaagtgtaa    12720
gtcacccaat atcgtgtagc agtctaatca tgctctaacg gaccgggatg gttgaaagat    12780
gacgatcgat acggcatgca gctcgtcgtt ggttgccgtt catctggcgg tgcaacagct    12840
acggacgggt caaagctcca tggcaattgc tgcgggtgcg aatctgattc tggggcccat    12900
gacattcgtc cttgaaagca aattgagcat gctatccccc tcgggtcgat cccgcatgtg    12960
ggacgccgga gctgacggct atgccagagg cgtgagtgtt tcttgagctc gtagatgaca    13020
gttcccatcg ctgaccgtga tcaggaagct gtttgctctg tagtgttgaa gacattgagt    13080
caagccttgc gcgatgggga cacgattgaa tgtgtcatcc gagaaactgg ggtgaatcaa    13140
gatggccgaa cgaccggaat tacgatgccg aaccatagtg ctcaggaggc actcatcaag    13200
gctacctacg cccaggctgg ccttgacatc accaaggccg aggacaggtg ccaattcttc    13260
gaggctcatg gtcagcaaag agaacctgtt ctgttggcgc cctgcagctg acattcgtat    13320
gatagggact ggtactccgg ccggagatcc ccaggaggcg gaggccattg caacagcctt    13380
cttcggccac gagcaggtag cacgcagcga cggaaacgag agggcccctc tgttcgtggg    13440
cagtgcgaaa actgttgtcg ggcacaccga gggcacggcc ggtctggctg gtctcatgaa    13500
ggcgtcgttc gctgtccgcc atgggtaat cccccccaac ctgctgttcg acaaaatcag     13560
cccgcgagtc gccccattct ataaaaacct gaggattccg acagaagcta cccaatggcc    13620
agctctccca cccggacaac cgcgccgcgc cagtgtcaac tcctttggta agcgaggatt    13680
gcccggagga acccctcacaa gtactcgaat taatgctaac tgaaccgcgc cgatggacag    13740
gattcggcgg cacgaatgcg catgccatta ttgaggaata catggagcca gagcaaaacc    13800
```

```
agctgcgagt ctcgaataat gaggactgcc cacccatgac cggtgtcctg agtttaccct   13860
tagtcctctc ggcgaagtcc cagcgctcct taaagataat gatggaggag atgctgcaat   13920
tccttcagtc tcaccccgag atacacttgc acgacctcac ctggtcctta ctgcgcaagc   13980
ggtcagttct acccttccgc cgggctattg tcggccatag tcatgaaacc atccgccggg   14040 cttttggagga tgccatcgag gatggtattg tgtcgagcga cttcactacg gaggtcagag   14100
gccagccatc ggtgttggga atcttcaccg ggcagggggc gcagtggccg gggatgttaa   14160
agaatctgat agaggcatcg ccatatgtgc ggaacatagt gagggagctg gacgactccc   14220
tgcagagctt gccggaaaaa taccggcccct cgtggacgct actggaccag ttcatgctag   14280
aaggagaggc ctccaacgtc caatatgcta ctttctccca gccattatgc tgcgcggtgc   14340
aaattgtcct ggtccgtctc cttgaagccg cgagaatacg attcacggct gttgttggac   14400
atagctccgg cgaaattgct tgcgcctttg ctgccgggct catcagtgcc tcgttggcga   14460
ttcggattgc ttacttacgt ggagtcgtct cggcaggggg cgccagaggc acaccggagg   14520
ccatgttggc cgccgggatg tcctttgagg aagcacaaga gatctgcgag ttggatgcct   14580
ttgagggccg catctgcgtg gctgccagca attccccaga cagtgtaact ttctctggcg   14640
acgcgaacgc aattgatcac ctgaagggca tgttggagga tgagtccact tttgcgagac   14700
tgctcaaggt cgatacagcg taccactcgc atcatatgct tccatgtgca gacccatata   14760
tgcaagccct agaagagtgt ggttgtgctg ttgccgatgc aggttcccca gccggaagtg   14820
taccctggta ttcgtccgtg gacgccgaga acaggcaaat ggcagcaaga gacgtgaccg   14880
ccaagtactg gaaagataac ttagtatctc cggtgctatt ctcccacgca gtgcagcggg   14940
cagtcgtcac gcacaaggcg ctggatatcg ggattgaagt gggctgtcac ccagctctca   15000
agagcccatg cgtcgccacc atcaaggatg tcctatctgg ggttgacctg gcgtatacag   15060
gttgcttgga gcgaggaaag aatgatctcg attcattctc tcgagcactg gcatatctct   15120
gggaaaggtt tggtgcctcc agtttcgatg cggacgagtt catgcgtgca gtcgcgcctg   15180
atcggccctg tatgagtgtg tcgaagctcc taccggccta tccatgggac cgctctcgtc   15240
gctactgggt ggaatcccga gcaactcgcc accatcttcg agggcccaag ccccatcttc   15300
tattaggaaa gctctccgaa tacagcactc cgctaagctt ccagtggctg aattttgtgc   15360
gcccacgaga cattgaatgg cttgatggac atgcattgca aggccagact gtcttccctg   15420
cggccggcta tatcgtcatg gcaatggaag cagccttaat gattgctggc acccacgcaa   15480
agcaggtcaa gttactggag atcttggata tgagcattga caaggcggtg atatttgacg   15540
acgaagacag cttggttgag ctcaacctga cagctgacgt gtctcgcaac gccggcgaag   15600
caggttcaat gaccataagc ttcaagatcg attcctgtct atcgaaggag ggtaacctat   15660
ccctatcagc caagggccaa ctggccctaa cgatagaaga tgtcaatccc aggacgactt   15720
ccgctagcga ccagcaccat cttcccccgc cagaagagga acatcctcat atgaaccgtg   15780
tcaacatcaa tgctttctac cacgagctgg ggttgatggg gtacaactac agtaaggact   15840
tccggcgtct ccataacatg caacgagcag atcttcgagc cagcggcacc ttagacttca   15900
ttcctctgat ggacgagggt aatggctgtc ctctcctgct gcatcctgca tcattggacg   15960
tcgccttcca gactgtcatc ggcgcatact cctcccagg tgatcggcgt ctacgctgtc   16020
tgtatgtacc cactcacgtt gatcgcatca cacttgtccc atccctttgc ctggcaacgg   16080
ctgagtccga atgcgagaag gttgccttca atactatcaa tacgtacgac aagggagact   16140
acttgagcgg tgacattgtg gtgtttgacg cggagcagac caccctgttc caggttgaaa   16200
```

```
atattacttt taagcccttt tcaccccgg atgcttcaac tgaccatgcg atgtttgccc     16260
gatggagctg gggtccgttg actccggact cgctgctgga taacccggag tattgggcca   16320
ccgcgcagga caaggaggcg attcctatta tcgaacgcat cgtctacttc tatatccgat   16380
cgttcctcag tcagcttacg ctggaggagc gccagcagga agccttccat ttgcagaagc   16440
agatcgagtg gctcgaacaa gtcctggcca gcgccaagga gggtcgtcac ctatggtacg   16500
accccgggtg ggagaatgat actgaggccc agattgagca cctttgtact gctaactcct   16560
accaccctca tgttcgcctg gttcagcgag tcggccaaca cctgctcccc accgtacgat   16620
cgaacggcaa cccattcgac cttctggacc acgatgggct cctgacgagt tctatacca    16680
acacactcag cttcggaccc gcactacact acgcccggga attggtggcg cagatcgccc   16740
atcgctatca gtcaatggat attctggaga ttggagcagg accggcggc gctaccaagt    16800
acgtgttggc cacgcccag ctggggttca acagctacac atacaccgat atctccaccg    16860
gattcttcga gcaagcgcgg gagcaatttg ccccttcga ggaccggatg gtgtttgaac    16920
ccctcgatat ccgccgcagt cccgccgagc agggcttcga ccgcatgcc tatgatctga    16980
tcattgcctc caatgtgcta catgcgcacac ccgacctaga gaaaaccatg gctcacgccc   17040
gctctctgct caagcctgga ggccagatgg ttattctgga gattacccac aaagaacaca   17100
cacggctcgg gtttatcttt ggtctgttcg ccgactggtg ggctggggtg gatgatggtc   17160
gctgcactga gccgtttgtc tcgttcgacc gctgggatgc gatcctaaag cgtgtcgggt   17220
tttccggtgt ggacagtcgc accacggatc gggacgcaaa tctattcccg acctctgtgt   17280
ttagtaccca tgcaattgac gccaccgtgg agtacttaga cgcgccgctt gccagcagcg   17340
gcaccgtcaa ggactcttac cctcccttgg tggtggtagg agggcagacc ccccaatctc   17400
agcgtctcct gaacgatata aaagcgatca tgcctcctcg tccgctccag acatacaagc   17460
gcctcgtgga tttgctagac gcggaggagc tgccgatgaa gtccacgttt gtcatgctca   17520
cggagctgga cgaggaatta ttcgccgggc tcactgaaga gaccttcgag caaccaagc    17580
tgctgctcac gtacgccagc aatacggtct ggctgacaga aaatgcctgg gtccaacatc   17640
ctcaccaggc gagcacgatc ggcatgctac gctccatccg ccgggagcat cctgacttgg   17700
gagttcatgt tctggacgtc gacgcggttg aaaccttcga tgcaaccttc ctggttgaac   17760
aggtgcttcg gcttgaggag catacggatg agctggccag ttcaactaca tggactcaag   17820
aacccgaggt ctcctggtgt aaaggccgcc cgtggattcc tcgtctgaag cgcgatctgg   17880
ctcgcaataa ccgaatgaac tcctcgcgcc gtcccatata cgagatgatc gattcgtcgc   17940
gggctcccgt ggcattacag acggctcggg attcatcatc ctacttcttg gagtccgctg   18000
aaacctggtt tgtgcctgag agtgttcagc agatggaaac aaagacgatc tatgtccact   18060
ttagctgtcc ccatgcgctt agggtcggac agctcgggtt tttctatctt gtgcagggtc   18120
acgtccagga gggcaatcgc gaagtgcccg tcgtggcctt agcagagcgt aacgcatcca   18180
ttgtgcacgt tcgtcccgat tatatatata ctgaggcaga taacaatctg tctgagggtg   18240
gtggcagcct tatggtaacc gtcctcgccg cggcggtgtt ggcggagacg gtgatcagta   18300
ccgccaagtg cctgggggta actgactcaa tcctcgttct gaatcccccc agcatatgtg   18360
ggcagatgtt gctccatgct ggtgaagaga tcggtcttca agttcatctg gccaccactt   18420
ctggcaacag gagttcggtt tctgctggag acgccaagtc ctggctaaca ttgcatgctc   18480
gcgacacgga ctggcacctg cgacgggtac tgccccgggg tgtccaggct ttagtcgact   18540
tatcagccga ccagagctgt gaaggtttga ctcagaggat gatgaaagtt ctgatgcctg   18600
```

```
gctgtgccca ttaccgtgcg gcagacctgt tcacagacac cgtttccact gaattgcata    18660
gcggatcgcg gcatcaagct tcactgcccg ccgcatattg ggagcatgtg gtatccttag    18720
cccgccaggg acttcctagt gtcagcgagg ggtgggaggt gatgccgtgc actcaatttg    18780
cagcgcatgc cgacaagacg cgcccggatc tctcgacagt tatttcctgg ccccgggagt    18840
cggacgaggc tacgcttcct accagggttc gctccattga cgctgagacc ctctttgcgg    18900
ccgacaaaac atatctcctg gtcggactga ctggagatct tggacgatca ctaggtcgtt    18960
ggatggtcca gcatggggcc tgccacattg tacttacgag cagaaatccg caggtgaacc    19020
ccaagtggct ggcgcatgtt gaagaactgg gtggtcgagt cactgttctt tccatgtaag    19080
aggagtcctt ccttctgcaa ttcctcctta tgatcccgac taacgcagct ggcttcaggg    19140
acgtgacaag ccaaaactca gtggaagctg gcctggctaa actcaaggat ctgcatctgc    19200
caccagtggg gggtattgcc tttggccctc tggttctgca ggatgtgatg ctaaataata    19260
tggaactgcc aatgatggag atggtgctca accccaaggt cgaaggcgtc cgcatcctgc    19320
acgagaagtt ctccgatccg accagtagca accctctcga cttcttcgtg atgttctcct    19380
cgattgtggc cgtcatgggc aacccgggtc aggctaacta cagtgcggct aactgctacc    19440
ttcaagcgct ggcgcagcag cgagttgcat ccggattagc agtacgtttt cactccatcc    19500
tttgctaaac actcctatgg gcctttacta aaccgggcag cgtccacca tcgacatcgg    19560 tgccgtgtac ggcgttgggt tcgtcactcg gcggagctg gaggaggact ttaatgcaat    19620
tcggttcatg ttcgattcgg ttgaggaaca tgaactgcat acactgtttg ctgaggcagt    19680
ggtggccggt cgacgagccg tgcaccagca agagcagcag cggaagttcg cgacagtgct    19740
cgacatggct gatctggaac tgacaaccgg aattccgccc ctggatccag ccctcaaaga    19800
tcggatcacc ttcttcgacg accccgcat aggcaactta aaaattccgg agtaccgagg    19860
ggccaaagca ggcgaagggg cagccggctc caagggctcg gtcaaagaac agctcttgca    19920
ggcgacgaac ctgaccagg tccgtcagat cgtcatcggt aagttgagcg aatccgggga    19980
atattctccc cttcctcact cagcggactg gagattaacc gcttcttttc ctttggcaga    20040
tggactctcc gcgaagctgc aggtgaccct gcagatcccc gatggggaaa gcgtgcatcc    20100
caccatccca ctaatcgatc aggggtgga ctctctgggc gcggtcaccg tgggaacctg    20160
gttctccaag cagctgtacc ttgatttgcc actcctgaaa gtgcttgggg gtgcttcgat    20220
caccgatctc gctaatgagg ctgctgcgcg attgccacct agctccattc ccctcgtcgc    20280
agccaccgac gggggtgcag agagcactga caatacttcc gagaatgaag tttcgggacg    20340
cgaggatact gaccttagtg ccgccgccac catcactgag ccctcgtctg ccgacgaaga    20400
cgatacggag ccgggcgacg aggacgtccc gcgttcccac catccactgt ctctcgggca    20460
agaatactcc tggagaatcc agcagggagc cgaagacccc accgtctta caacaccat    20520 tggtatgttc atgaagggct ctattgacct taaacggctg tacaaggcgt tgagagcggt    20580
cttgcgccgc cacgagatct tccgcacggg gtttgccaac gtggatgaga acgggatggc    20640
ccagctggtt tttggtcaaa ccaaaaacaa agtccgacc atccaagtgt ctgaccgagc    20700
cggcgccgaa gagggctacc gacaactggt gcagacacgg tataaccctg ccgcaggaga    20760
caccttgcgg ctggtggact tcttctgggg ccaggacgac catctgctgg ttgtggctta    20820
ccaccgactc gtcggggatg gatctactac agagaacatc ttcgtcgaag cgggccagct    20880
ctacgacgga acgtcgctaa gtccacatgt ccctcagttt gcggacctgg cggcacggca    20940
acgcgcaatg ctcgaggatg ggagaatgga ggaggatctc gcgtactgga agaaaatgca    21000
```

-continued

```
ttaccgaccg tcctcaattc cagtgctccc actgatgcgg ccctggtag gtaacagtag     21060 caggtccgat actccaaatt tccagcactg tggaccctgg cagcagcacg aagccgtggc     21120
gcgacttgat ccgatggtgg ccttccgcat caaggagcgc agtcgcaagc acaaggcgac     21180
gccgatgcag ttctatctgg cggcgtatca gtgctgttg gcgcgcctca ccgacagcac     21240
cgatctcacc gtgggcctcg ccgacaccaa ccgtgcgact gtcgacgaga tggcggccat     21300
ggggttcttc gccaacctcc ttcccctgcg cttccgggat ttccgccccc atataacgtt     21360
tggcgagcac cttatcgcca cccgtgacct ggtgcgtgag gccttgcagc acgcccgcgt     21420
gccctacggc gtcctcctcg atcaactggg gctggaggtc ccgtcccga ccagcaatca     21480 acctgcgcct ttgttccagg ccgtcttcga ttacaagcag gccaggcgg aaagtggaac     21540 gattgggggt gccaagataa ccgaggtgat tgccacgcgc gagcgcaccc cttacgatgt     21600
cgtgctggag atgtcggatg atcccaccaa ggatccgctg ctcacggcca agttacagag     21660
ttcccgctac gaggctcacc accctcaagc cttcttggag agctacatgt cccttctctc     21720
tatgttctcg atgaatcccg ccctgaagct ggcatgatgg cgcaaacata gaacatgata     21780
gcgcagcagg gacgatgtag atagagcttt gcttctgcgg gtggatctat aatatagtat     21840
atataaatat ggtgagccga acgaagaggg gggaatgcca caattattta ctgttttgcg     21900
ccgtacacga ggagaagacg tccagaacaa cataaatata tcactctagt gagacaccat     21960
atattcggag agactataaa aatatacatc tactccaatg tctgggccgt cacacacagc     22020
ttacgaaaac gattaatgac ctccaacacg tcgcgcggtc gattgggaaa ctgatgctgc     22080
ccagcaaact ccaatacctg cgcctctcgg ggggagaaat ggcgcgccac cagcatcttc     22140
gatcctgcga gcgcaaaatc atcgcgaccc tgcagatgta atgtcggtat ccgaatgacc     22200
agttcctcct gccactcggt atctttgctg tcgttgtcgt cgtcatggtt cttcatcact     22260
tcgttcctca tatactggct tgcctcgtct tgataccagg gacagatcaa cagcgcaaca     22320
ctcatccggg gcaaccaggg caggtgaccc atctgctgct gccagaggag caaggtcgtc     22380
accagggcac cttcggagaa accgatagca cccacgatag ggatgtgggg gtgttgagtc     22440
tgccagtcga caatggtgcg gcggatgggg tcgtggacgg cggcgaggcg ttcgctcacg     22500
gagggtccat tatgattgtt gtcgctgctg ctttcaaacc aggagtaata tggccctagg     22560
tcggcgaaga cggggagaat cccaggccct gcagaggaag ggaacggagc tgtcacgtag     22620
acgaattcaa agttttcgcg cagcgcagcc cggagcttag acaattgcac gcggaagatg     22680
gcgggagagc agccagcccc atggatgcaa agaagcgctc gaggcgcctt caccagcgct     22740
ggagatgctt ggtaacgcat ggaggagggt acaatgggac tatatcctgg atgcaagacg     22800
gggatgaggg agtgtcgagc ttacacgttc accagcgatg aaccgctatt attgcaacgg     22860
aatatcctgt ctaacactct gcatctactc caggtggacg ggacaagcca gcgatgccga     22920
ttacatccat aggaacagca gttttgttcgg aacttccgct tcatcccctc gatatcgggc     22980
gcaggatgcc ggcgccgaat aacgccgcac aaacccgaac gggtctgcag gtgatcccga     23040
agccctaatc caaggatcgt ccgtccttct gtctatgtct ttccgcatat gtaggccgca     23100
gcgtaccaga tacgtcactc aacagttaac cagagaagac gaccgtgaca gactgccatg     23160
ggcgaccagc cattcattcc accaccgcag caaacagcgc tgacgtaaa tgaccatgat     23220 gaagtcaccg tctggaatgc cgcaccctgc cccatgctgc cccgcgacca ggtatacgtc     23280
cgcgtcgagg ccgtggcgat caatcccagt gacacgaaga tgcgcggaca gtttgccacg     23340
ccctgggcgt ttctcggaac ggactatgcc ggcacggtcg tcgcagtggg ttcggacgtg     23400
```

```
actcatatcc aagtgggtga ccgggtctac ggggcacaga acgagatgtg cccacgcacc    23460
ccggatcagg gggcattctc gcagtacacg gtcacgcgag gccgtgtttg ggccaagatc    23520
cccaagggct tgtcgttcga gcaggctgcc gcgctacctg cgggcatcag taccgctgga    23580
ttggcgatga agttgcttgg gctgcctttg ccatcgcctt cggcagacca gccacccacc    23640
cactccaagc cggtgtatgt gttggtctat gggggcagta cggccactgc cactgtcact    23700
atgcaaatgc tccgcctgta atgcttccct tgtcctgaga cttttctctc cgttggtcgt    23760
gggctgtaca agcgatggtt atactaagat ccgctggcag gtccggatat attccaattg    23820
caacatgctc cccccacaat ttcgacctgg ccaaatcgcg cggcgcagag gaggtctttg    23880
actatcgggc cccgaatctc gcgcagacga tcgtcagtga acccctgcca ccgctctacc    23940
cctcccagtc cactttggcc ttacagaaca gactattgat attcttctag cgtacctaca    24000
ccaagaacaa tctccgctat gctctcgact gtatcaccaa cgtcgagtcc accacattct    24060
gcttcgcagc catcggccgc gcgggggggc actacgtctc cctgaacccg ttccctgaac    24120
acgcggccac gcgcaagatg gtcacgaccg actggaccct ggggccgacc atctttggcg    24180
agggatcaac ctggcccgcc ccctatgggc gtcccggcag tgaggaagag cggcagttcg    24240
gcgaggatct gtggcgcatc gcggggcagc tcgtcgaaga tggacgcctc gtccatcatc    24300
cgttgcgcgt ggtgcaggc ggcttcgatc acattaagca aggcatggag ctcgtccgga    24360
agggagagct gtcgggggag aaactcgtgg ttcggctcga ggggccgtaa actggattgc    24420
gcgttacgtc gagggagcaa gaaagctcca attttctat caaccaatcc gtagacgcta    24480
aaacgtacat gggatattgc tgcgtggatt gggataaatc acgagtgata cacagggtgg    24540
ggttttaaga atacattgaa cacatactca gacaactctt tatgaactga tatacactac    24600
ttgctctctg ggaagatccc tgtccccagt atatcataga ttaagagaaa aaaaaaaaa    24660
acatccacgt catataccta aactatcgc tatatatata gatatatata tatatctata    24720
tatatgttag caagctcatt gtcttctaca gaacttaata atcgaaatac aaatagccaa    24780
tatcatcccc ggcatggctg ctatgcggat taaccctgct ggtactgcgc atagatggca    24840
tgctcgaatg tgcgtgtcag atcacgacag accgggtcat tccagggttc cagttggaag    24900
aacgcaaggg tgcacaggcc ggctttgggg tcgatttgct aattacaata gcacttagta    24960
ggctggatca acattgaagg tgacataaac caaaggaatc taggagccga gcttacccac    25020
acaatgtttg ggccacccc aaaggtcaag gaaccttttc ggcgccagtt ctctccgtcc    25080
agatcctcca aggcgatgat cccccccagc ccaaagctgc gacgaaggac catgggcatc    25140
ggcccaccgt agttgatatg tgggctggcg tccatgtgct ggttcatctg ctcttcgagt    25200
cgcggctcga gggcaggctg aaacatcaag tccacggtct gtggctgcag caggagcccg    25260
tctcgcttca acagcgagtg aagcaccttc ataggacc cagggcccga aacacccc    25320
tggccgccga agcactcctc tccatcggcc cggaagtaga ccgagtcgtc gtagcgcagg    25380
cgcccatccg ccgagttgcg gtgcgtttgg tcggcccggc gcgcaagcat atccggccgt    25440
tgctgcagct taaaggtcat gtcggtgatg cccagcggcg cacagatatt ctcctgcagg    25500
tactgctcca ggtcgaggcc ggtggcccgc tcgacgagct tacccgccca gtccaggttg    25560
gcgccgtaga tccactccgc cccagggtcg ttgacgccg gcggcgccag gcgactctgg    25620
atgccaaact tttctgccga ctggaggtgg ccctgggcca tgtattcccg gagcaacgga    25680
tggaggaaga cgtacgacag tcccgatgta tgcgtcagca ggtgccgcag cgtgatcttc    25740
ccccgacgct ctcgcaatct tgcgtttccc gcgtcgtcaa accctccag cacgggcatc    25800
```

```
gcgctcaaat ccggaagcag cctatccacc gtctcatcca agtccacgag accgcgctcc    25860
atgcattgta gggccatgat cgtggtcagc agcttggtcg cactggcgag ccggcagggg    25920
gtgtcgacct gtagcggcgg cagctgattg cactcgtccc gtcgcaccgt ccgagccccg    25980
aagcagcgcg tataatttag attgcctagg tatgtcccgc tgtcattcgt ctcggtgtgc    26040
ttgtaattgt cgcaaagggg tccgattggg gtctctcacc actgcaatct cgggccatga    26100
tgaccgcccc ggggatctgc ctggatttca cggccttgcg gaaggcggtt tccatcagaa    26160
caaccggatc cgctgccgca gcagcatcaa tgatggatcc cattctgaat ttttttaattt    26220 ttttcccttt ttactaataa ataaatagat gaaatagggg aataaaaata aaccaaaaa    26280 gaaagaaaat cgggcgctta ttttgtctgc ggctggggcc atagatcgga ccttacctac    26340
ctatccaagg gcgatcatcg gatcgggccg gcggatcgtt acatcaggcc ggtccccgaa    26400
taagaccgac tcggtgactt tcggtgttat gcgccgctag gaacggtatt gtcttagact    26460
ctgtattgta aaagctacct aacctcactt aggtaggtag gtaggtacct aggtactctc    26520
cagctgtatc ttacgtacag gtccgtgata ctactacctt acctacctaa gttacatgac    26580
aaggtaggta cttttctacg taggtaggta tttttatatt cgatttgcac gaaatggatg    26640
tctcccgcat gttctaagat taccacatat accggtgttc taattgctcc gtactctgta    26700
ccggagatag cgtcctttga agctgccccg agaatcaatc acagcgatcc cttcatttct    26760
tgactgtggc acccgcactg cgattgtgtt gcatatgggc attgaccaag tgacccgccg    26820
caagagccgc gcaggtactt aactcgccag ccagcacggc cgcggcgaca atgcgggcca    26880
agcggcgcgc attggcgcca ggctccgtgg aatgtgcgcc ccggacacct agcaagtcca    26940
acatggctcc ctgggcctca agaatggtgc ctccgccaat cgtgccgacc tccatcgagg    27000
gcatcgagac agcgatgtgc aggtttccat cgatgctaga aacccaccat tagcaaacac    27060
acccacgtga atatatataa ccgggaggag aaaatcaaaa cgtagagaag ctacctactt    27120
tttcatggtc gtaatgcaac tactgctctc cacattctgc gccggatcct gaccagtggc    27180
cagaaacacc gcctggacga ggttggaggc atgggcgttg aagccgccca ggctgcccgc    27240
catggcactc ccgaccaggt tcttggccgt gttgagctcg accagcgcat cgacgtcggt    27300
cttcaggacc tgtcggacag tctccgcggg gatcgtggct tcggcgatga cggacttgcc    27360
gcggccgccg atccagttaa tggcggcgga tttcttgtcg gaacagaaat tgccagataa    27420
ggtaaccgta tgcatgtcgg gaaatccacc ctcggcggcc atcgcctcca gggctttttc    27480
aacgcccttc gaaatcatat tcatgcccat cgcgtcgccc gtggtggtgc ggaaccggat    27540
gtagagatag atgcccgcct gggccaccgt cagggtttgg agccgcgcaa accggctggt    27600
cgcgttgaag gcggccgcca gaacctcgtg cccgagagga gactcaaccc agcgctgggc    27660
ttcagctgca cgttgggccg acgggaatcg cagacaggga ccacgcgtca taccatcacc    27720
tttgagcatg gtagtggcac cgccgccagc attgatcgct ttgcatccgc gactggcgct    27780
cgcaacgagc acgccctcgg ttgtggccat gggaatgaac aacgcctgtc catcgatcac    27840 catggtccg gccactccca ggggcagagg caggtacccg accacgttct cacagcaggc    27900
gccatgcaca agctcgtagt tatagtcgcg ataagggagc aatgactccg ccaggccgct    27960
gcagaggttc tgagtggagg gcgttttcga cacagcggca cggcgaatcc gcacggcacg    28020
cgtaaatgcc tccagccggg tcaccgagcg ggatgatccc gccgcaatcc gctcgagagt    28080
cttctctaaa ctgtacccc g cgatcttacc ccggagacac agttccacca gctcgtcgtc    28140
cgtcagagat tctgcttggt tcgatttgag gagggcctct gtttcttctg gggggcgagt    28200
```

```
acagacttca ggggcagtgg cagagcatgg caccgacaag taggagccat cagggacggc    28260
ggactctctc gcttggggcc aagcatgcca gcgagcagcg tggatcaggt ggttgttgag    28320
gaccaggcta acgaccaatg cgcccatgag acatagtcga cccagcgggc tttccaatcc    28380
atcgagcaca ccgtcaaatg tagaacgttt agtggctgat atattgaacc cagctgattc    28440
caagacgtac tgcagtggcg gcagaacggt tacgcgtgtc tcaaaccect cgacgcgcgc    28500 cgttaggtag atctcgttga gtccgttggc cgcttctttg aaaggactga cagcagtagg    28560
gggcagagta ccattagcca tatattctcc catgacccga tagaagaagg gcgacaattg    28620
gaggaagtga catagaacga agccgccacc cgtcaatagc ttccaccagg tgatgtttgt    28680
cgacttgacc ttgtgcccaa aaatccccga aggatgcttg gcattaactt gaccaagccc    28740
tcctgggctc cggattcgcg tgatctctaa tttcacgcaa agaatggtgg catagaaggt    28800
aaaaagtaga acggcatcaa tcaggagtgt ccatgccgcc aggaagcaaa aatggccaag    28860
actatccttt ggccgaagga ccgccectaa tgccaacgcg ccgatttcca ggaggtaaga    28920
tcgcacaata taccacccct ctcgatcaac cgcgagttgg atgatgttag gaatcaattg    28980
gttttgccgg ctatcatcac tgctggcgcc attgggaact tgccgctgcc cccgccecca    29040 cagttcttcc gacacgcaga aacagcacg ggttagttgg atcggcttct caaagcccac    29100
tgtcagaacg aggtacggga ttccttcgaa aagaagaagc atgtcgacgg gcacgtcgca    29160
tgtagtcgtg attccaagcc cgagtacaaa agcaaaggca ccagacagca ggaccgaggc    29220
tgccaaccag aagcgtgagc cgaggtggcg catcacccga aagagagaga ccacagtcat    29280
attcatggct aggtaactga gccctatgat caccaagtcg actgtctccg catggtgaac    29340
acgatgaagg aatgacagcc atgagcttcc gagccagtgt cccagtgacc tgggacttcc    29400
ttcttcgcga ggagacctca gtctccaact atcatcctct ttttccgagg gtataatttc    29460
gacagcctgt agaaagccat ctagttggga gtagggaact cgaaacgtca acgcggaatg    29520
atcgggtgag ggggatgaat cggggggtggg cgtggtctgt tccgcaccga ggaaccetga    29580 gagcgtgttt gataggaagg ggatactggc gtcgacagac gcacccggta gatcgagggt    29640
gacaagagcc cagtgaaagt cagactaatt gagagtagca cagggacggt ccggtcagca    29700
cgcagaattt ctcggaccaa tggagcgcag gagatctatc atacctgcc atcctccggc    29760 accttaggtc ggtcgtctat ctgccatttc catgcgctag cctctcccag gctaacagtg    29820
cggcttcccc agagaaatga ctggacgttc aagggggttt ccttggccca ggggccaga    29880 cctctgtgag tagcctgata tgtcccttcc agcacatgaa gatgggtcgt tgccgcggtc    29940
agcgccgtga ctagcagagt gtgaatggga tgtcgacacg cgtgtcccac aatggcacgc    30000
aatgctttgg tcactcgatg ctgcaccccg ccagggtccg gctttctaac caccggatcc    30060
attgcgatga ctctcttggt gcgcgagaga ggggtgtgag tgcttgtgga tgatgtaaag    30120
acaagtacaa gattcgcaga aaggtcaaag agactagaaa aaaataaaat aaaaaaatta    30180
aaataaaatt aaaaaaaaacc cctaaagaac aagaaaagaa gagagaaaga aagagagaga    30240
gagagagaac caagcctcag ggaaggaagg aaataagcca aggcaactcg cttggtgcga    30300
cccaatgcta ggaggtccat gagactccgg tacttcctgg taatattgag ccaaatatac    30360
ttattctagg taggcggtag ggatttaat gcgtatgcct atgatacaat aatgtacat    30420 gaaggcgact gcacaaacaa tcttacgccg tttggctcgc tggctagaag agtaagcact    30480
aaacaaggcc agggttgggg aaatcttctc cactgtcaga cgtccttcgt accttagagg    30540 tactaccta ccgaggtaag gtactttatc tgaacacgga attacatcct cttaccacga    30600
```

```
attttcagat ctcccaattt tgtaggttat gaaatattga aatttattga cctgccccg    30660
tccattggct aggtattaca cacggctgta tctctatctc atagaatggt atctagtacg    30720
ctcttttcga tattacaaag gtggcttttt caggaaattt ggaaatatcc agtgggaaga    30780
gggtgtacgt actctagtag gtaaggtacc ttacctacct taccttctgg agtcctggta    30840
agattgtttg tgtaatgaat cgatcagctt agtgcgctaa aattcggtca ccctgtagaa    30900
acataacaat atttcctttc ttcagcccct acctaaatta ggtgttcaaa gccaaggagt    30960
aatacatacc gtcagtattt ctaggttggc aggagggatt ttgatgctgt cacccttggc    31020
gcatcatgca cgattcatga aacagactgc actatccgtc ttacgcgcct tagcgccgcg    31080
gctgaacgag taagcactca gccaaggagc cccccctc ccggcccac ccctggcag        31140
ggctgtcaaa gcggatcgag tctcattggg tttgcttatc aaaatcggtt ggtaatccag    31200
gtagcagtag catctggatg taaactaata aaaggcaga ctgtcgggac cttaaaaggc     31260
caaagaggta cccatgcccg ggttcttcgg tcgccagaac tgcaatgtat caaatgtctg    31320
atgctcatga cccaggacac agcacagtac agggggcaa tggctgcaga tcaaggtata    31380
ttcacgaact cggtcactct ctcgccagtg gagggttcac gcaccggtgg aacattaccc    31440
cgccgtgcat tccgacgctc ttgtgatcgg tgtcatgcac aaaagatcaa atgtactgga    31500
aataaggagg ttactggccg tgctccctgt cagcgttgcc agcaggctgg acttcgatgc    31560
gtctacagtg agcgatgccc caagcgcaag ctacgccaat ccagggcagc ggatctcgtc    31620
tctgctgacc cagatccctg cttgcacatg tcctcgcctc cagtgccctc acagagcttg    31680
ccgctagacg tatccgagtc gcattcctca aatacctccc ggcaatttct tgatccaccg    31740
gacagctacg actggtcgtg gacctcgatt ggcactgacg aggctattga cactgactgc    31800
tgggggctgt cccaatgtga tggaggcttc agctgtcagt tagagccaac gctgccggat    31860
ctaccttcgc ccttcgagtc tacggttgaa aaagctccgt tgccaccggt atcgagcgac    31920
attgctcgtg cggccagtgc gcaacgagag cttttcgatg acctgtcggc ggtgtcgcag    31980
gaactggaag agatccttct ggccgtgacg gtagaatggc cgaagcagga aatctggacc    32040
cgtgcgtcgc cgcattcccc aactgcttcc cgtgagagga tagcacagcg ccgacaaaac    32100
gtatgggcaa actggctaac agacttgcat atgttctcac tagatcccat cggaatgttt    32160
ttcaatgcgt cacgacggct tcttactgtc ctgcgccaac aagcgcaggc cgactgccat    32220
caaggcacac tagacgaatg tttacggacc aagaacctct ttacggcagt acactgttac    32280
atattgaatg tgcggatttt gaccgccata tcggagttgc tcctgtcgca aattaggcgg    32340
acccagaaca gccatatgag cccactggaa gggagtcgat cccagtcgcc gagcagagac    32400
gacaccagca gcagcagcgg ccacagcagt gttgacacca taccttctt tagcgagaac    32460
ctccctattg gtgagctgtt ctcctatgtt gacccctga cacacgccct attctcggct    32520
tgcactacgt tacatgttgg ggtacaattg ctgcgtgaga atgagattac tctgggagta    32580
cactccgccc agggcattgc agcttccatc agcatgagcg gggaaccagg cgaggatata    32640
gccaggacag gggcgaccaa ttccgcaaga tgcgaggagc agccgaccac tccagcggct    32700
cgggttttgt tcatgttctt gagtgatgaa ggggcttcc aggaggcaaa gtctgctggt      32760
tcccgaggtc gaaccatcgc agcactgcga cgatgctatg aggatatctt ttccctcgcc    32820
cgcaaacaca acatggcat gctcagagac ctcaacaata ttcctccatg aaccaatcca     32880
gcctttggaa gtgtgtgcaa ccactgcgta gcgccctgtc attcggtgcc ggacagagtc    32940
tctcagtggg gtgggaagat ataggaaatc ggacatcgcc acatcgactc ttacacccac    33000
```

-continued

<210> SEQ ID NO 19
<211> LENGTH: 31328
<212> TYPE: DNA
<213> ORGANISM: Aspergillus terreus

<400> SEQUENCE: 19

| | | | | | |
|---|---|---|---|---|---|
| ctaccacgaa | acttcagatt | ttcctatttc | acggccttta | gaatactgac | atccgttgat | 60 |
| cttcccctat | tttctgtgag | gtagtaagtg | tggcagtatc | tccctcctat | atttggcagg | 120 |
| ctcttttcaa | tattatatat | agaagtggcc | ttttcttaga | aattggaatt | tcctggcgag | 180 |
| agggcgtcgt | ctgagactct | agtcacttcc | aactattgca | gctacatgga | ggagtacctg | 240 |
| ttgactaagt | tgtactctgt | gatttgtttg | ataaacactc | aataggtttc | tagcacgttc | 300 |
| cagttgtagc | tgagcactca | actagctaac | gggtgagaac | attgaagcgt | caattctttt | 360 |
| tacccggaat | acttttaaca | gctatgtatg | gttatttggg | accggggaag | gaattaaatc | 420 |
| acgcagggct | tcttcttcac | tcccatgcga | cctactcaca | ttgtgttcaa | agtacggac | 480 |
| gtgtctggat | caatggctcc | gacagacggc | caagaaaacc | aatgcatttg | ccaagaatac | 540 |
| aaatggctac | gtactagtcg | agtagggcgc | ggtcctgctt | gccgcctcca | aggaaaaacg | 600 |
| ggcatttact | agatttgttt | gttgcaggta | ttgtactcgg | atagtccagc | ccagggatca | 660 |
| attgactttg | agacaagcag | cgggccccgg | cggccaatcg | gctttaagg | cgggtagggg | 720 |
| tcgggtggtc | tactgtatgc | ggttcctccc | gatcaccaca | ttacgtctta | cattgcatac | 780 |
| ctaggtaaat | cttatggtac | tgtaggtata | cacaatattg | gtgaaagtta | ccggtaaaaa | 840 |
| gaaaatggaa | aaactagaaa | ggcagaaatt | ttaccggtaa | gataagtgaa | tttcgtttta | 900 |
| ttcgcagggc | atgatggtat | gataggtaca | tttacgaaaa | cttgaactca | tgataatacg | 960 |
| gtaccacaga | cagcttaggc | gccctgcat | ccctttgta | ctctcgtact | ccatatagaa | 1020 |
| aagcttgtat | gtttggctgg | acctgctgcc | acgagtcggc | ctggtccgtc | ttactacttg | 1080 |
| tatatcagag | ccgctttgta | aggttttggt | tcgcctcggt | tttgcgattc | catatggggg | 1140 |
| cttttagggt | acggaaatcc | atgtaaacaa | taccagctga | agtacctact | aggtgccacc | 1200 |
| taggcgctaa | ggtacctaag | tacatcttca | tcccaaaaac | aaagataaag | gagttctaaa | 1260 |
| ttacgttaga | ttccgcattg | ctgcagcgac | acacgtgatt | ttaggcttcc | catcaccagc | 1320 |
| aagctcacct | ccaggaggcc | cctttccctt | ggacctgact | aaggcatcgt | gttcgccggc | 1380 |
| aaccttacca | taaggtagaa | tgacatccca | ccacggtgaa | acagagaagc | cacagagcaa | 1440 |
| cacggctcaa | atgcagataa | atcatgtcac | tggcctcagg | ctaggcctgg | ttgtggtttc | 1500 |
| agtcactctg | gtggcgtttc | tgatgctctt | ggatatgtcc | atcattgtca | cggtcagcat | 1560 |
| ggcaccagcc | tggagattgc | tccgagcctt | ggagacaact | gactcttcac | attcgcaggc | 1620 |
| gattcctcac | attaccgccc | agtttcattc | cctgggcgat | gtcggatggt | acggaagtgc | 1680 |
| gtatcttcta | tcaaggtgat | cgatttttcca | acccatgccc | tcttccttt | ctccagccgg | 1740 |
| gtttctattg | actccacgac | acgctctagc | tgtgccctcc | aacccttggc | aggcaaacta | 1800 |
| tacactctgt | tgaccctgaa | atacaccttc | ctcgcttttc | tcgggttgtt | tgagattgga | 1860 |
| tcggttcttt | gcggcactgc | tcgttcgtca | accatgttga | ttgtagggcg | agcagtggcc | 1920 |
| ggaatgggag | ggtcgggct | caccaatggc | gcaatcacca | ttctgtcggc | ggcagctcca | 1980 |
| aagcaacagc | aaccgcgtaa | gtactgatag | ccagacctat | ctcaaccgtt | gttatgctat | 2040 |
| gctgacccgg | atatttacac | atagtcttga | ttgggatcat | gatgggccgt | cagttcgcca | 2100 |
| acccattggg | atccccggaa | atcatcaagc | atagtttctg | actccattcc | cagtaagcca | 2160 |

```
aatcgccatt gtatgtggac cgttgcttgg gggtgctttc acgcagcacg caagttggcg    2220
gtggtgtatg tatccccatt ggatttatcg gttcagtgct tgctttctca aaggaccttg    2280
gctacgactc cgccacgtca agatctttcg ctcacggtga ttctggtcca ggtttttaca    2340
tcaaccttcc cattggggcg tttgccacat ttctccttct cgtcatccag atccccaaca    2400
gattgccatc cacgtcggat tcaaccacag acggcacaaa ccccaagaga gaggggctc     2460
gggacgtctt gacccaactg gatttccttg gattcgtgct cttcgccggt tttgcgatca    2520
tgatatctct tgctttggag tggggtgggt ctgattatgc gtggaatagt tccgtgatca    2580
tcggcttgtt ctgtgcggcg ggcgtgtcgc tggtgctgtt cggatgctgg gaacggcatg    2640
tcggcggtgc agtggccatg attcccattt ccgtggccag tcgtcgccaa gtctggtgct    2700
cctgcttctt cctcggcttt ttttccgggg ccctactat tttctcctac tacctgccta    2760
tctacttcca ggcggtcaag aatgtttctc ccaccatgag tggagtgtat atgctgccgg    2820
gcattggtgg acagatcgtc atggcgattg tgacgggtgc aatcagttga gttgccacca    2880
ttccaccacc tttcttcgct tataacctat ggcgttactg acaaattgag ggtggtagtc    2940
ggtaaaacag gctattacgt tccgtgggcg ctcgcaagcg ggatccttgt gtccatatcc    3000
gccggactgg tatcgacctt ccagccggaa acctcgattg cagcatgggt catgtatcag    3060
ttcctgggag gcgtgggccg aggatgcgga atgcaaaccg taggtgacct ggatcgtttc    3120
catcggtttg cgccgcactc ttatgcaaat gctcattgac tcggttgtcc ctcctttagc    3180
ctgtcgtcgc cattcaaaat gcgctgcctc cacaaacgag ccccatcggc atttcgctag    3240
ccatgttcgg ccagacattc ggtggctcgc ttttttctcac cctgaccgaa ttggttttta    3300
gcaatggttt ggactctggt ctgcgccaat atgcgccaac cctcaatgca caggaggtaa    3360
cagccgcagg ggccaccggc ttccgccaag tggtccccgc tcctctcatc tctcgggtcc    3420
tcttagcata cagtaaaggc gtggaccatg cattctacgt tgcggtcggt gcgtctggag    3480
ctaccttcat cttcgcctgg ggtatgggcc ggcttgcctg gagaggctgg cggatgcagg    3540
agaaaggacg gagcgaatga atttaatcct atcgtaggga acgccaaaga atattaata    3600
tttctatgga gatagccatg taccgtttgg caactcatac actctaccta ctcttctcaa    3660
accaaacgaa ccattttat gacaggaaga gcaataatta atcacgaacc agttgtgacg     3720
acagacccgt tcaactgtgg cctttttttg gcgcttcatg ggtaaacact tcagtgttga    3780
tgagattcct agcttgacct gagcagacct aaacctgcat tacctagtca tggaaatatg    3840
cattcgaata cctgacatgt tctgttacga atccacggca tcggtatatt caatggacat    3900
ggccttccag tatttgcttc tcttaaagaa agttccatgg ttccattgta atggttaact    3960
gacggcttcc ttgtacacat tggccatcac aggtgatttg agcaagacag tcgaggagat    4020
caacattgag attcggtatc aagcactgat accacacaga actggcgggt atgaagcagc    4080
ccgtcttggt agtgtggcag agaaatcgtg gcgtgtagca cctacgcttc agagcaacta    4140
tcgcgccctc agaccgcag accaactgga gtaccggact cggcgttttg gtcggcgtta     4200
tcaaccgggg ttattgtacc gccaacccgt gcagctacct agctcactgt ggagaatgga    4260
taatgctagg cttcggtctg acgatgtcat tctattgctg atgatgttcc tggcaccct     4320
ttatctacca tcctggcgag gtcgaatcag cccgcgtccg tcatactcca ggtgtgcgca    4380
gtaaggaagg cacatccatc aaacatcaaa ctagaagaaa ttggccacga tgacaccatt    4440
agatgcgccc ggtgcgcctg ctcccatagc tatggttggc atgggctgca gatttggcgg    4500
aggcgcaaca gatccccaga aactgtggaa attgctggag gaaggaggga gcgcctggtc    4560
```

-continued

```
taagattcct ccttcacgat tcaatgtcgg cggggtctac cacccaatg gccagcgggt    4620 aggatcggtg agtatgaagg attctgggtt gagcattttt gaggcccata tcttcctgtt    4680
cagaacgata ggcgttgact gcgagtagat gcacgttcgc ggtggacact ttctcgacga    4740
agacccggct cttttcgatg cctcattttt caatatgagt actgaagttg ccagtgtacg    4800
tcccgcgatc gttgtccagt tgtgtatgga tcagaagcgg aataaaccca tgctaagact    4860
gccgaatagt gtatggaccc ccagtaccga ctcatacttg aagtcgttta tgaggcgctc    4920
gaagctggta tgtattatat tccttggttt cccacgtggg tattaactcc ccatggctcc    4980
gcagcgggaa ttcctctcga acaggtctcc ggctccaaga ctggggtttt tgcaggaacc    5040
atgtatcacg actaccaagg ctccttccag cgccaaccag aagcccttcc acggtatttc    5100
ataacaggaa atgctggcac catgctcgcg aatcgcgtct cccactttta tgaccttcgt    5160
gggcccagtg tctcgatcga cactgcctgt tccacaacct taacagcctt gcatcttgcc    5220
attcagagct tgcgagctgg agaatctgat atggcgattg tcgctggcgc gaacctgcta    5280
cttaatcctg acgtctttac taccatgtcc aaccttgggt gagtctggtg ttcaatccat    5340
ctagtgatca gcattcttgt tgcacagaca atatgtgatg ttaactgtga tgtgctgcga    5400
ccagcttcct ttcgtccgat gggatttcct actcatttga ctcgagagcg gatggctatg    5460
gtcgcggaga aggagtggct gcgatcgtct tgaagactct gcccgatgcg gtgcgagacg    5520
gagacccgat ccgcctcata gtgcgcgaaa cggcaatcaa ccaagacggc cggaccccag    5580
ccatcagcac gccgagcggc gaggcccagg agtgcctgat ccaagattgc tatcagaagg    5640
cccagttgga cccaaaacag acttcgtacg ttgaggccca tgggacggga accagagcag    5700
gagatccgct ggagcttgca gtcatctcgg ccgcgtttcc gggacagcag atacaggtgg    5760
gctccgtgaa agccaatatc gggcatacag aggctgtcag tggtctggcg agtttgataa    5820
aggtggctct ggctgttgaa aaggggggtta tcccgcctaa tgcaaggttc ctccagccga    5880
gcaagaagtt gctcaaggac actcatatcc aggtagcatt atcttcacga ttttttcctc    5940
tcattctatt ctttctattc cagctcctcg ctgatttaca aacagattcc actgtgtagc    6000
caatcatgga taccaaccga tggtgtccgt cgcgcatcaa taaacaactt cggtttcgga    6060
ggcgcaaatg ctcatgcaat cgtggagcaa tatgggcccgt ttgcagaaac atcgatctgc    6120
ccacctaatg gttattctgg caactatgat ggcaatttag gaacggatca agcgcatata    6180
tatgtgctga gtgccaagga tgagaacagt tgcatgagaa tggtttcaag gctgtgcgac    6240
tatgctaccc acgccagacc agccgacgat ttgcaattgc tcgcgaatat agcatacacg    6300
cttggttctc gtcgctcgaa cttccgatgg aaggcagtat gtacggcaca cagcctcacg    6360
ggtcttgccc agaatttggc gggagaaggc atgcggccaa gcaagtcagc cgaccaagta    6420
agactgggat gggtgttcac aggccaggga gcgcaatggt ttgcaatggg tcgtgagttg    6480
attgagatgt atcctgtctt taagaggcc ctgctggaat gcgatggata tatcaaggaa    6540
atggggtcaa cctggtccat tataggtaaa gacccgcaac aagtccccgg cccaggctat    6600
ggaaagcact cactcatgtc accattgcag aggaactcag tcgccctgaa acggaaagtc    6660
gcgttgatca ggcagaattc agtctgccat tgtctacggc tcttcaaatt gcgcttgttc    6720
gtctgctctg tcgtggaac atccaaccag tagccgtcac tagtcactcc agcggagagg    6780
cagctgcagc gtacgctatc ggggcactaa cagcccgctc ggccattgga ataagctata    6840
tacgcggtgc attgacagca agagaccgcc tggcgtcggt acataagggg gcatgttgg    6900 ctgtcggatt gagccgcagt gaagtgggta tatacatcag acaggttcca ttacagagtg    6960
```

```
aagaatgctt ggtggtgggg tgtgtcaaca gcccgtcgag tgtgacggtc tcgggagatt    7020
tgtccgccat tgccaagttg gaggaactgc tccatgctga tcgtatattt gcgagacggc    7080
tgaaagtcac ccaagccttt cactccagcc acatgaactc gatgacagat gctttccgag    7140
ccggtcttac agaactcttc ggagcagacc ccagtgatgc agcaaacgcc agtaaagatg    7200
tgatctacgc ttctcccaga accgggccc gcctgcacga catgaatcgt cttcgggatc    7260
ctatacactg ggtcgaatgc atgcttcacc cggttgagtt cgaatcagca ttccgtcgaa    7320
tgtgcctgga cgaaaacgac cacatgccaa aggtcgatag ggtcattgag attggacctc    7380
acggagcgct tggaggcccg atcaagcaga tcatgcagct tccagagctt gccacgtgtg    7440
acatccctta tctgtcctgt ctttctcgtg ggaagagctc tctgagcacc cttcgccttc    7500
tcgcatcaga acttatccgg gccggatttc ctgttgactt gaatgcgatc aactttcccc    7560
gcggatgtga agcagctcgg gtccaagtgt tgtctgatct accgccctac ccttggaacc    7620
acgagaccag atactggaaa gagccgcgca tcagccaatc tgcccggcag cggaagggcc    7680
cagtccacga tctgatcgga ttgcaggagc cgttgaacct gccgttggcg cggtcatggc    7740
acaatgtgct tcgtgtgtca gatttgccat ggctacgcga ccacgtcgtc ggctcgcata    7800 ttgtttttccc tggggctggg ttcgtgtgta tggcagtgat gggaatcagc acgctctgct    7860
cgtccgacca tgaatctgac gacatcagtt acatcctacg cgacgtgaac tttgcgcagg    7920
ccctgattct acctgcggac ggggaagaag gaatagatct gcgcctcacg atttgtgctc    7980
ccgatcagag tctgggttca caggactggc aaagattctt agttcattcg atcactgctg    8040
acaagaatga ctggacggaa cactgtacgg gacttgttcg agcagagatg gaccagcctc    8100
cctccagttt gtcgaaccaa caacggatag acccacggcc atggagccgt aaaacggcgc    8160
cgcaggagct gtgggactca ctacatcggg tgggaattcg tcatgggccc tttttttcgaa    8220 acattacgtg catcgaaagc gacgggcgag ggtcatggtg tacatttgcc atcgcggaca    8280
cggcctccgc aatgccacac gcctacgaat cccagcacat tgttcaccca accacactag    8340
actctgcagt tcaggcagcc tataccactc ttccattcgc tgggagccgg atcaaatctg    8400
cgatggtccc cgctcgcgtc ggctgcatga agatttcctc ccgacttgca gatttggagg    8460
ccagggacat gctgcgcgca caagcgaaga tgcacagcca aagtccttcc gcattggtaa    8520
ccgatgtagc agttttttgat gaggcagatc cggttggagg gcctgttatg gagctcgaag    8580
ggctggtctt tcagtctctg ggggcaagtc tgggcacttc tgaccgggac tccaccgacc    8640
ccgggaatac ttgcagctcc tggcattggg ctccagacat cagcttagtt aaccccggct    8700
ggcttgaaaa aaccctgggc acaggtattc aggagcacga gatcagcctc atattggagc    8760
ttcgacggtg ttcggtgcac ttcattcaag aggccatgga aagtttgagc gtaggcgatg    8820
tcgagaggct gagtggtcat ctggccaaat tctatgcgtg gatgcagaaa caactggcgt    8880
gtgcccaaaa tggcgagctg gggccagaga gctccagctg gactcgggat agcgagcagg    8940
caagatgcag cctccgctct agagtggttg ctggtagcac caacggcgaa atgatctgtc    9000
gcctgggctc cgtgctcccc gctatcctac gtcgggaagt tgatccgttg gaggtgatga    9060
tggatggcca cctgttgtcc cgctactatg tcgatgccct caagtggagt cggtccaacg    9120
cgcaagccag cgagctcgtg cgcctctgct gccacaaaaa cccgcgcgct cgcatactgg    9180
aaatcggcgg aggcaccggg ggttgcaccc agctggtcgt ggactccttg gcccaaatc    9240 cgccggtagg ccgctatgac tttactgacg tctcggccgg gttttttgaa gcagcccgca    9300
agcggttcgc gggatggcag aatgtgatgg attttcggaa gttggacatc gaggacgatc    9360
```

-continued

```
cagaagcgca ggggtttgtg tgcggatcct acgacgtggt gttggcttgt caggtcctgc    9420
atgccacttc taacatgcag cgcacattga ctaatgtgcg caagctgttg aagccaggag    9480
gcaaactcat tcttgtcgaa accaccagag acgagcttga cttgtttttc actttcgggc    9540
ttctgcccgg ctggtggctc agcgaagaac cagaaagaca gtcgactccg tcactaagcc    9600
ctacgatgtg gcgcagcatg ctgcacacta ctggattcaa tggtgtggaa gttgaggctc    9660
gtgactgcga tagccacgag ttctatatga ttagcaccat gatgtccacg gccgtacagg    9720
cgactccgat gtcatgctcg gtcaaattgc ctgaagtgct cttggtctat gttgactcat    9780
ctacgcccat gtcttggata tcagatttgc agggagagat tcgcggcagg aattgttccg    9840
tcacttcgct acaggcactt cgtcaagttc ctcctaccga gggccaaata tgcgtattcc    9900
ttggagaggt ggaacactcc atgcttggtt cagtcaccaa cgacgacttc acactttga    9960
cctcaatgct acagctggct gggggaactt tatgggtcac ccaaggagcg acaatgaagt   10020
ctgatgatcc cctgaaggct ctacacctcg gattactacg taccatgcgt aatgaaagcc   10080
atggcaagcg atttgtctca cttgacctcg acccttcgcg taatccatgg acaggcgatt   10140
cgcgcgatgc cattgtcagt gttctggatt taattagcat gtcagatgaa aaggagtttg   10200
actatgcaga gcgggatgga gttatccatg ttcctcgggc atttagtgac tccatcaatg   10260
gaggcgagga agacgggtat gccttggagc cattccagga cagccagcat ctcctgcgac   10320
tagatataca gactcctggg ctcctcgatt ccctgcactt cacaaagcgc aatgtggaca   10380
catatgaacc agataaatta ccggacgact gggtagagat tgaaccgagg gcgtttggtc   10440
ttaacttccg tgacatcatg gtcgcgatgg gtcaattgga atcaaacgtc atgggcttcg   10500
aatgcgccgg cgtggttaca agtctcagcg agacagcaag aacaattgca cccgggcttg   10560
cggtcggaga tcgggtttgc gccctcatga acggacactg ggcgtcgagg gtgaccacaa   10620
gccggaccaa cgtggtgcgc attccagaga ctcttagttt cccgcatgct gcctccatcc   10680
ctctggcctt cacaacagct tacatttcac tttacaccgt tgcccgcatt ctgccaggtg   10740
aaacggtgtt gatccatgcc ggggcaggag gcgtaggcca ggcggccatt attcttgctc   10800
aattaaccgg tgctgaagtc tttacaactg ctggcagtga gaccaagcgt aaccttttga   10860
tcgataaatt ccacctcgac cctgatcatg tcttctcgag cagggactcc agcttcgtcg   10920
acggtatcaa gacccgcacc cgtggcaagg gggtggacgt ggttttgaac tcgctagctg   10980
ggcctctcct tcagaagagc tttgactgtc tggctaggtt tggtcggttt gtagaaatcg   11040
gcaagaagga tcttgagcag aatagccgac tcgacatgtc gacgttcgtc cgcaatgtct   11100
ccttctcctc cgttgatatt ctctactggc agcaagcgaa gcccgctgaa atcttccagg   11160
cgatgtccga ggtcatcttg ctgtgggagc gaacggcaat cggcctgatt catccaatat   11220
cagagtatcc tatgtcggcc ctggagaagg cctttcgcac tatgcagagc ggccagcacg   11280
ttgggaagat tgttgtgaca gtagccccgc atgacgcggt cctcgttcgt caggaacgaa   11340
tgccactatt tctgaagcct aacgtgtcgt atcttgttgc tgggggcctg ggtggtatcg   11400
gacggcggat ctgcgagtgg ctggtcgatc gcggggcgcg atatctcatc attctgtctc   11460
gaactgctcg cgtggacccg gtcgtgacga gtctccaaga gcgggctgc accgtttctg   11520
tacaggcgtg tgatgtggcc gatgaaagcc agcttgaagc ggctctccaa cagtgtcggg   11580
cggaggaaat gcctccgatt cggggcgtca tccaagggc aatggttctc aaggacgccc   11640
tcgtctcgca aatgacggcg gacgggtcc atgccgccct gcggcccaag gttcaggaa   11700
gttggaatct gcaccgaatt gcatcggacg tggatttctt cgtgatgctc tcatccttgg   11760
```

```
tgggtgtcat gggaggcgca ggacaagcca actacgcggc tgccggagcg tttcaggacg    11820
cgctcgcaga gcaccgcatg gctcacaacc agccagcggt caccatcgac ctcggaatgg    11880
tccagtcaat tgggtatgta gcagagacag attctgctgt ggcggaacga ctccaacgga    11940
tcggctatca acccttgcac gaagaggagg ttctggacgt cctcgagcaa gctatatctc    12000
ctgtgtgttc ccctgccgca cccacacggc ctgctgtcat cgtcaccggc atcaacaccc    12060
gcccaggccc tcactgggca cacgccgact ggatgcaaga ggctcgcttt gcggggatca    12120
agtatcgtga tccgttgagg gacaatcatg gagctttgtc gctgaccccg gcggaagatg    12180
acaatcttca cgccaggctg aaccgtgcaa tcagccaaca ggagtcaatc gccgtgatca    12240
tggaggcgat gagctgcaag ctcatctcaa tgttcggcct gacggatagc gaaatgtccg    12300
ccactcagac attggcgggg atcggcgtgg actccctggt cgccattgag ctccggaact    12360
ggatcacagc taagttcaat gttgatatct cagttttcga gttgatggag ggccgaacga    12420
tcgccaaagt cgcggaagtg gtgctgcaga gatacaaagc ttagatatat atgtatatgc    12480
atatctctcc ctatagctac atatatattg acatgcctcg atagtgtctg attttctctc    12540
ttacagcatc ccgttctgag atgcagattt gtttcttgcc tagcgtgaat acgtcacttg    12600
ttgtgtgaca atgaataaat cagagccata gccatgcaag cgtaatccta tagagtcctt    12660
ggatgagacg aaggccatgt atcagcgcag cacatcttgc tgtctctttt attcattaat    12720
gctcgtccgt agaccggaaa atggttttat tatcttaggt ttccctatca ataagatcct    12780
tagctgggtc cgcagggtta agaggccact gccacaatcc aggttaatag tctcaacatc    12840
gtggtgctgc aacgtctgat tgaggatctg tgtaacatct acggatggta aggaaaattg    12900
gttgaagaat gttgcatagc cctttgagat gtatgtagag ttgtttgggg caggttcggg    12960
tttacgctct aggatctgct gcagattacg ggttgaaacc ccccagacgt gctgggttta    13020
gttagtgtag gttaattagg ataggtctat gaagctactt actacttact aaggtttgta    13080
gtcttgaggg tagctgggaa tccatgtcgt cgggccatac tttgggaaac actttagaga    13140
cacggtgcaa cccaccatat cgcccgcacc cgccacgctg cagccagagg gaatagaaag    13200
aaaacagaag agaaacgcag ataaagaaca acggcgttgg attcctgcaa caagccttgt    13260
cccacgctac ctgcagcgcc tcccaatttt cacatgggtc cggcggaacg aacgtgagac    13320
aagatgctac cgccgagtgc gcagccggaa gggatttggg acacggaggc gtgtctaacc    13380
ctatattggt taggtgtctt aagtgatgtt tatcgtcggt tcgcacagag ttacacgaat    13440
atcccctttt cctgatatga tgtatattta tatgtaaggt gccatctcca catacatcca    13500
tccatccatg gatacacccg tcttcactct gtaccttatg gcttcagcag acaagaatcc    13560
ggaggagaca tcgcttaaga attcctgcgt cgccatacct cccgtcaata tcaccaccgc    13620
caccccaact gccctctccg cctacgcccc ctcgcgccaa ccctcggagc ccaccctcat    13680
cgaagaagag aaaactcctga cccacaaaca caccttcgaa atcttatcaa gatgggtcta    13740 ccgcccacatc gtcacctcgc caccgctcat cacatcccca catctggccg atgtcgccgt    13800
acgagctctc caacgcgccg agccgggttt ttctctccac gacaagggag atactacata    13860
tacttctgac tcggaggatt cgactccata taccgacacc gacacagacg aggagttact    13920
ctactcgtat gcggcaattt gtccggcgtt ttcggcggga gatgcagagt atcaacgtca    13980
ccaccggatg ggcgtatatc ccatgaattg ggtacgtatt accgacatat atccttgcaa    14040
cgcaactcta ctgctaataa gttagcagtg ctatttttcga ttgattgtgg gttgcaaagc    14100
tagacacata ccagaacccc aaggcactct ctaaacgggc ctatctagta gtctctcata    14160
```

-continued

```
tcgaattatg tcctcctcca taataagacc aaattcgctt tggctagtca tgtcaatgcc     14220
aagtggaaag tcggagaagt tgtcaatgcc aagtgaaaag tcgggaaaac caaggcattg     14280
gccagcatca ttgctcagca aatcctgggt tgcatcctca gaaggagtcg caattgtacc     14340
atccattggt atttctctcg ggttgaagta tatgtcccag acctggccgt ctccgggtac     14400
accaagcggg ctgatattca agttatatga agagccggtg ctagttgtgc tagtggacgc     14460
attggcgaca tcgtaatcca tgtaggttgg ctcgttccat gagggcgttg gacttcgtga     14520
tatcgttgtc ggaataaaac gcctctccct taaattctgg aggaggaggg caatatcgct     14580
acagcgactg gccacttggc ttaatttgta cgagatagat gcagatgacc tattggatgc     14640
cgaacggttc gtgtatatgg cgaagaaagt gagtatctcc atgtcctgtg aatggatcgg     14700
ctggtcttcc tccacaatgt ggacatagat tcccatgaat gagatcaaag aatagttcag     14760
gacaatgcta tgaagtacat ccccaggtta ggatgctgtc aagagggtcg cacggaagac     14820
ttacctgtcg aaattgctga aaccagattt acacccatcg cacaattgct tgaacagcat     14880
cagacaatcc cgagcgtgtt gtaggcagac agcgcccctt tcctggctcc aaatgcgttt     14940
atgcagaagt acccaacagc tcgagagtgc aaacctcaac tgcgttgcac agatatactc     15000
ttcgagaggc ctattcggat ctccggtacg cagtacatgc tcatgttgca cgtgccactg     15060
gctaagtttt cgagcaattc tgcggatacg gcggcggacg cgactctgtt ccatttgct      15120
ggattttgct gagtataagc ccagatatat ctcctcaaga atgaatgcca agcgtatgcg     15180
tgccgcaaaa gcatttggta gtggcgcagc ggagtcatat ggaggcaatg gtacgctgca     15240
gtcatacgag ggcaataggc aggccttgcc cccaatgatg gatacgtgct tctaaatcct     15300
atagtaagcg aaatgctcag aaaacgaagc aagttttga cgaacatcga cgaggaagat      15360
gctccagaac aagtctttag gctggtcgcc cacagcccca tcttccgttg gcgggtcgt      15420
tgtcgttaaa tggagtccaa tgagcctgga caactcgcag acttgagcaa agatagtcag     15480
aaaaattgcg aaatcaaaat actccattgc cacaagtgcc ttagtataat aaagtcaggc     15540
cacgttccaa aggtagggtt gtaagacgca ccaaacaaaa gagggcccgt atattcgata     15600
gccgggtttt aacaagagtt tccaatcgat tatagcactg cctgatatta cgcagcaggc     15660
ttatgatcat ataatctatt ggtatgtctt gtcctgtgca tcccacgact tgttcgcaa      15720
ttgatgtttg agtcagggcc tgaagcacaa tgcagttgaa agaggtaatc caaaccaggt     15780
ccggaggccc agttctgatt gtgtactgag attccactgc gtccataata gtctgtcgac     15840
taaatatagg gagtcgtgga tgcagcttct tgaaatattc gttgatagac ggctccacta     15900
gagcgcgggg tggaagagac gggagaaagg tatcgttttc ggatgccgat agtgttggga     15960
tatcctcaat gatctgttga agcgtttcat tcgcctcagc caccttcgag cgcacagctg     16020
acacagcttg gcggtcaaat gcgaccatct ctgcgacttg ccgctggtc atatcgaccg      16080
gtaaccaaga ggttaggttg gcgttagcag cctgtgcctc catgacgagt gaaacaaaag     16140
agccataacc gtggagaggc cagaatccat cttcctcggt gggtgaagtg tgtttgcctg     16200
agtacaagtt tacttcacac tcttctgagc tggttgagct tgtgtacccg ctttcttgtg     16260
actgtggcct tgatagatca cgaaagccct gatgggcatc aataaaggac aggcatcgtt     16320
ggagggcatg ttcgatatct ccaacccgac tcccagcctt ctcgacgtcg cgcgccctga     16380
ctgagagtca gaaagacagg tatttgaccc aaatatagac catcttatca cttacaattt     16440
tgctgttttgg ttgaccccgtg taactttgtt ggagaattca cagggtaggt tatatcggag     16500
gcaatgggag cactttggac cctccttgct gcatcggacc ttacggatcc ggcactcatc     16560
```

```
acatgcagga aatgcctgcc gcttcgacga cagctctgca ctctccatca ttcaactcta    16620
tgtgagatag aacatgagtg aacgatgagg gaaggccctg gtactcagat aagtccttga    16680
tgtctctgta gatctcaact gtgcaagacg aagactggtt tgaagtaagg cccacagctg    16740
aagtggcatg ataagttcac ctgttggttt aatataccct attgttgatg aaagcctgac    16800
cttggccaaa gaagggagca gctgagtatc cgacatattt gataaggacc agcggcaagc    16860
ttgggatctg ctgcatactc ggattacgcg aaaaggtagt cggagtacgt gaaaaggtac    16920
tcggagtacg cgaaaaggtt agattaagcg ctacggacgc cggcagtccc tgaatgaaac    16980 tctgcgggc ccacttgccg ctgacggtgg cacgatgaac cttctggccc ctactctaat    17040
atagcacaag gtgctcgaat aacaaagctt gtcgccatcg tggcgttgac gccagcatgg    17100
ctctgcattt gctgtactat acggtaagct tagtagggcc aaatttatac tatagtatgt    17160
tatttccgat ttacgtacgg aatgggaaag aacttgtatg cggccgcagg ctgaaaaggg    17220
ccgaattaaa gaactgccat aactatgtgc atcccgatga tgcctcaagc gcagcattca    17280 acagggcaa aatatcgtca caggtcagat ttattactac atcgggaagt cttcggagat    17340
tgattccgag gcatagagtg ccttggacta gcgacgccaa gtttctacta tcaggaaaag    17400
tgctagttcc agattggaac tagccaataa gtagccagcg gtaagctgaa caactaattt    17460
ttaaatatta gatgaacaaa tgcgtagttc agagacacca tgcacgttgt ccaatactat    17520
gaggctttag caagacaaag tggagcacac gccacctggt aaaagtgaac accgtctgct    17580
gcaaaagctc gtggagtttt attttgatta ctagaaagca gacatcccct ccttgtcccg    17640
gaatattgca aatcagggaa cattgaataa gctgggccgc taatgcgtgc taagaacagg    17700
gagtccacca gagtgaggta gatcccttcg tatttcagct gtggcaggac agcgatctgc    17760
ggagctccga cggctagccg tatggcattg acagtgaagg agatcggaac ctctactcca    17820
gagtacattc cgaaaagcca taattattcg gatgtacgga atacggaggg atgataagcg    17880
ctagaaatag ggtggatcct actaaaattc ggatcctta gcttgtgcta acgtgtcaag    17940
ctggggcatc ctgtagtccg tgctactcct ataggtttac cggctatata aatctggtgg    18000
agccagcggc ccctgcacct ctttaggaca cgcggcccct tcaaaaaagt caaaatagca    18060
gtcaagagca gtgaaagaga cccatgctgt ctcatagaaa agcaaggaac ctcgaaatcc    18120
acatgagatc gatccacatg gttctacttc aagtgggtca ttaattcccg tcacctgaga    18180
catgagatac ttagtagcta agatatggta catgctgttg atcaaacgat atgagtgtca    18240
tgttggggtg aatactaagg aacatttcta ccaacaatct cgcggtgaat agaaaactga    18300
cctttaaatt ccagcacggc gaacgaacag catccatatt tcagtttggc tgcgtcaaga    18360
acttgtagac tttctcgtac cttgacgctc tgtcagtgta caagaatatc atgcctgtag    18420
attactccta aacttacacg ggaaacatga tggccgaggt aagggaaagt ctccctgtcc    18480
gaaaccagac gccggaccag aaaaccccaa tgccttcatt gcgcagaagt gttttcacgc    18540
agttaaaggt atttccgtac agttgtcttg cctgaagaga ttgcattctg gtaacccgaa    18600
gtcgcatcca agtcagcata tacttatctg ggcgggttac tgtcgatctg agcagcactt    18660
accgcgtctt gatcacgtcc agtggctgtg tcgaccaggc gcaacaaact ccagtaacag    18720
aaccgaccaa ggtgcttgcc agagggtgca cgtcttcgcc gttcttcgag tattttcggg    18780
ccagcccaat aagttcgtta taaacagtga acttcactgc cgcattggac gactgccgca    18840
aaattgtagg accaaccgca gagaagaatc caagcggtcc ccgatctcga aggattccag    18900
ctatcgcgcc gaaagtcgta cttaactctg catttccaac cttccttgca tcaatgctaa    18960
```

-continued

```
gagaacgaat taagaactga tcggataacg ggtgagatgt tgcaacttac attttcgtct  19020
tgatcgcctc cgctggggtt acggctaaga cagcctcggt cacgccagcc ccaaacccag  19080
ccaggacgga agctccagtt gagagctctc catttgggcc cgagagggcc gagcgataaa  19140
tattgaagga ggcaaattct gtttgttatt gcaaacggtc attccttttc gctccacgcg  19200
ggcttataag ggggatcgct acatacgaac ggaggctttc aatgtggttc ctaccaaggt  19260
ggctccatac ccagcatacc agcctcggat tccaggtttt atagctgcca catcatggtt  19320
tctccgctta agctgggcgc gagttttagc cgctaccagc ggaagcaata gactgtcagt  19380
tggcggccac ggtaaagcgg aactcttaaa cacaggataa gctcacattc gaaagggtag  19440
gtgatggaga tttcaactgc cccagcacaa gcacccgcga ccaatgcagg aatgcctttc  19500
gtctatacat atattaagag aagacattgt cagtaacatg gcacacgcgc gaccaagaag  19560
gaacacatac acgcttccca cgggcttttt gggtaagggg tgcctttggt aatggaacat  19620
ttgtctggac tttagactcc atgacgagga tgtgctgagt ccaaacaaag cttttcttca  19680
cagagatagg gctgcagacg ttatttccag tttaccttcc ctgtgttcag tatcaggtct  19740
tatattgtat tatctcaatg cttatgactc taagtggaat acattggata tcagtttgtc  19800
acggagtcgg cacccgatgg ctatcgcaat cgtccctggt gggtcttgaa atcgtatgtc  19860
acacttattc cggatgaaac acattccgga gcgcgcgttg atattgctaa acagtataga  19920
cccaaatggt ctgcagaagg ccctaaatag taggtctcat tagccagtat ttagttgtga  19980
ttgcagatca ttgtcagcct aacatcagtg taggttacgg tgtgatattt acttgcatag  20040
aaggttccag accacacggt tctagatcct ttgacagcag catgaatgga ttcccctcta  20100
ggtgccgggc gccgacgtgt gcgttgctcc gaaatttgta ggacggagct cggatacctg  20160
gccgctatgg gcatcggagg ttgtagcagc gtacacgctt ggatagttaa ataatcggat  20220
gtacacccac tgttggaaat gacgggggcc taaaacacga gattatctga tccaatttct  20280
gttcgttggc attctatcat tcgcagcgaa gatcgtcctc ttaaattgac catgaccaag  20340
caatctgcgg acagcaacgc aaagtcagga gttacggccg aaatatgcca ttgggcatcc  20400
aacctggcca ctgacgacat ccctccggac gtattagaaa gagcaaaata ccttattctc  20460
gatggtattg catgtgcctg ggttggtgca agagtgcctt ggtcagagaa gtatgtgcag  20520
gcaacaatga gctttgagcc gccaggggcc tgcagggtga ttggatatgg acaagttagt  20580
tctatccaat ctgaacagtc tacaaagtat actgacgatc ctttgtatag aaactggggc  20640
ctgttgcagc agccatgacc aattctgctt tcatacaggc tacggagctt gacgactacc  20700
acagcgaagc cccctacac tctgcaagca ttgtcctccc tgcggtcttt gcagcaagtg  20760
aggtcttagc cgagcagggc aaaacaattt ctggtatagc tgtcattcta gccgccattg  20820
tggggtttga atctggcccg cggatcggca agcaatcta cggatcggac ctcttgaaca  20880
acggctggca ttgtggagcc gtgtatggtg ctccagccgg tgcgctggcc acaggaaagc  20940
tccttggtct gactccagac tccatggaag atgctctcgg aatcgcgtgc acgcaagcct  21000
gtggcttaat gtcggcgcaa tacgaggca tggtcaagcg cgtgcaacat ggattcgcag  21060
cgcgtaatgg tcttcttggg ggactgttgg cccatggtgg gtacgaggcc atgaagggtg  21120
tcctggagag atcttacggc ggtttcctca aaatgttcac caagggcaat ggcagagagc  21180
ctccctacaa agaggaggaa gtggtggccg gtctcggttc attctggcat acctttacta  21240
ttcgcatcaa gctctatgcc tgctgcggac ttgtccatgg tccagtcgaa gctatcgaaa  21300
accttcagag gaggtacccc gagctcttga atagagccaa cctcagcaac attcgccacg  21360
```

-continued

```
ttcatgtaca gctttcaaca gcctcgaaca gtcactgtgg atggatacca gaggagagac   21420
ccatcagttc aatcgcaggg cagatgagtg tcgcatacat cctcgccgtc cagttggtcg   21480
accagcaatg tcttctggcc cagttttccg agtttgatga caacttggag aggccagaag   21540
tgtgggatct ggccaggaag gttactccat ctcatagcga agagtttgat caagacggca   21600
actgtctcag tgcgggtcgc gtgaggattg agttcaacga tggctcttct gttacggaaa   21660
ctgtcgagaa gcctcttgga gtcaaagagc ccatgccaaa cgaacggatt cttcacaaat   21720
accgaaccct tgctggtagc gtgacggacg aaacccgggt gaaagagatt gaggatcttg   21780
tcctcagcct ggacaggctc accgacatta gcccattgct ggagctgctt aattgtcccg   21840
taaaatcgcc actggtataa atgggagcga tttcatgcca cgggcacaaa tcctagggca   21900
tatcgtacct gtatgatgga agcaccagcg gtttagcaga tagatgatag gttccttctg   21960
ctctgcgttg cgttttgaat ttagttactt cgctggctta agaatttaga atgaaatgca   22020
gtctctctta ttccttatta aactcacgta ctcccacatt cggcgactgg aggatacgaa   22080
agcagtgttg gtgatgtttc ctgtaatgga tatcattttg ctgactgaat tattctatga   22140
cctttccctc caacggcgtt cttatctcga cactttagat gttgacgctg ccttgaggaa   22200
ctagctttgc gctgcgaagg ctatgagcag tggagctgca tcctttcgcc tagatatcca   22260
ttctgcatag atccaaggca gggcttcgta agaaaagttc acgttcactg taagtccatg   22320
caagcggaac ggccgcttaa acaagtctat acagtaaagc ctgcctataa gcaaccgccc   22380
atataaggaa tcccgcgata ttagcatcta aaatccgcgt ctgaattgat tttctatata   22440
aataagcagt aaactgcttg aaaaagccct gctctcctat acaaagctac cttaattaga   22500
aaatataggt tgactagcta aaaatgtgcc ttacaatatc gtattattat ataatactta   22560
tatgaccacc ggaggtaggc tagaaatata tatcgtaaag agattacccc ttagtaaaaa   22620
tatatatttg tatagacctg gctgtaagca atttcttatt ataagtaact ttttggtgag   22680
ctgaattcgt tgcttatagc caggtttgct gtaattgata aaaggtgcca attcatcata   22740
atctatcccg catcggatga attgttgacg atccacacca taaactgcat tatgttctac   22800
attttcctca ttggtatcta ttgggtaggc aggttgaaag ccctttctgc ccacctttgc   22860
atatttatcc cccaccgtgc gatggccgcc gtgatcaatc cagctatagt cgaagcaacc   22920
acacctgcaa caactgtgag catgtacatt gagaggtaag aagaaaggta ccatacatag   22980
cgtgaacgtc catccaactc cgagggcgtc tatgacgggc acaacgagcg cactactccc   23040
tgcagaaaag gagtattgaa tcatatactt tcctgcaatg actgcagacc ggttccgtgg   23100
caaggcttct acttgcggtc agagacaaca ttattgtggg catgtacaca aagggggataa   23160
attaatgagg gtgtggaaca aaccagccac gtaagtgttc aggcagttaa aactgcccat   23220
gagcccccag cccgcgaaga acgccgcgat tatgggcact accatcccac ccttatcctc   23280
ttggagtgtc cacccgtaaa tgagcgttcc cgcaggcagc acgcaaaca atgtgatgag   23340
cccgctgtgg agtcgatcct gagggagacg gaatccgcgc tttactatgt atctccgaac   23400
ggtgcgatcc gaaagtttac cgccgacgag actccctatc aggaacccgg cacctggagc   23460
gaggtagaag agaccgata ctagggcagt cgttaaatga aaccgtgagt tgaatatagc   23520
acgagctgaa gtcaggatcg aatattgcgt aatcgcaggg aggccacagc ataagtcctt   23580
ttgtttgcgg catgagcatt tcgtttccag tagatgcaga gggcatatct cccaggcact   23640
tacggcaaga aagacatttg gatacaccca ctgcttgagc acatccgttg gggagaattt   23700
cgatatgatt gaaacaagtg tggtcggttt aaacgccgtt gagaccttct cagaagttcc   23760
```

```
ttcgattttc gggaaaaata gcagggaaag cacgagcccc agtccgctca tacctagttg    23820
aagccagaag ataacacgcc aactcgtgaa agtgacgatg acccctccca cgcaggggcc    23880
tgatcaaaca gtcagttcct gttgggagtt ctagtacttt cagcagggta cgtacctatt    23940
gcagggccag aaagagtccc ggccatgaag aaacctacgg ccgtcccacg gtaaacctgc    24000
gcacgaacgg attagttttc gcaattgggg agacaagggc gtgtgatgcg tacaggctca    24060
aagatatctg caagaacagt ttggcctgag accatgaacg aggttccggt taagccgctc    24120
aatactctga acgctatgaa cattttctcg tttatcgccg ctgccgttcc agcggagcac    24180
gcacaaagca ttgaaatggc cagattgtat gatgtccgcc tgccgactaa cttgttcatg    24240
ggaccccata tgagggatga atatcccatg caaccaaga caccagcatt ggagatattg     24300
atagtctcga cagtcatatc aaattcattc gcgatttcag gggcggcagg aagaagacaa    24360
gtactggaga aagtaacgac tagagtcatc caactaacaa caaacgtaat gacacatttt    24420
ctccataatg gaatatcacg gcccttttc tctggctcgt tttgtccgct accttccgag      24480
gtcgtcgctg ggttcgggga ctcagtgtca ccgcggccca tttctgcaat ggatggcctt    24540
ctcgtcactg agcggactct tcaaaagaaa atatagaaca tggtcaccca aaacatggat    24600
gttcctgatt gacggtttat gtatactcta tcatcggcct gccacacatt tcgccgagac    24660
tacgttgata gtgtattgga gcgccgctag accttcggcc ttgctggccg agacgggtac    24720
ctaataaggt agattgtgtc tttccgcaaa ggtattcatg tggatcagtc tagaatggct    24780
gcaaggccca ctgacttgac taatgcaagc caacgccagg atagttatat aaaatccaat    24840
gagggatcaa catcgggatc gacatcggga ccagcacccg gcatccacaa ggaccggatc    24900
cgaaaagtac ggccggccga aaggaaaccc atggaaggtg catagacctt cactgtacaa    24960
tacagtactc tgtggacaat gatattggcc accatctcac ccgtccgata tccatgtca     25020
ttgatgactg tatttcaaaa tagattggat atctgagaag tgatgaagtc tatagtatgc    25080
tctcttctgt atgagggatt ttgttggttc aacagggttt atcattagtt tgtcactatc    25140
tggccttcgc cgtacaggaa tgcaccgcat gtgtttgtac tctctgtgac tccctcgaga    25200
ctaaggacat acggtacgta tattggctaa ccaccattat taaagaagcg gtggccgagt    25260
gagtacctta ataaggcttg tatgccctct tagtagttgt cggataattt ctccaataat    25320
agggtggata caggggtaac ggcggaacgg aaagaactcc gccgtcggcc tgcggcgcgc    25380
ggcccacctg cacaaccagg ctgaattctc ttgaattctc tttttgatac cggaaggcgt    25440
gagaaggagg ggaaattcat catcttaagt gctcatctta tatctgcttg acgaatgcag    25500
attgcccagt gcgctcaccg gagcccgagc aaggggcta gagcgggtct gggttacata    25560
acgacagtgc gacaccctct tcatgtaaag atctcgcctt attcactttc cacattttga    25620
acatccgcaa ctgtgccgta cccagtctcg tgaagccggt aaaatggcta aattcgcagt    25680
aaaatgcctc gatcacttgg tcctgactgt gcggtctatt ccaagaacga ctgcatttta    25740
taccaagcat cttggtatgc gacatgagac gttcacctcg ccacttaatc gaactatcca    25800
gaggtattcg cgcggaagtt gtgatctaga ttgtcgcgat tcggcttact gaacagtcaa    25860
actaggcatg cgctcatctt tggttctcag aagatcaacc tccatgagca tactaaggaa    25920
tttgaaccaa aagcacgtaa tgtgcaaccg gggagtgcag atctgtgttt cttaacagat    25980
acagacgtct gccaagtgct caaggcattt agggacgccc agattgaggt atgtgtagca    26040
aatgcttcta aaagcgcaag cactgaaggt taggtgcagg tactagaaga ttccaaagtt    26100
gtggatagaa caggggcaca aggcaagatc cggagtgttt atgtgcggga ccctgatgga    26160
```

```
aatctagttg agtaagtgtt cttgttattt aacagatttc ccttgcttct aacatgtgtt    26220
aagagtatca aactatgtct catctagcca ggctggcggt caataagctt tacaaggtta    26280
tatgacccgt aactgagttg cgcctgtacc gtgattagag acaacattca ttgttccatg    26340
ttggcctcgt tctgtcatca gttggttaca cactggctta taggcaacat ttcgcgtaga    26400
tttaggtagt tatttgctcc gcagttccgc ttgtaatcaa agaaaaccgg gttctggaga    26460
atctgtttca tttcagggct cggcctggac agtgacggct gaggttctga tgggatatgc    26520
tgggtttagt ctccaccttta aacatagtcc acgtctcaat ggcgtattgg ataatatcga    26580
aggggatctg agttgctagt ccaacttaca cctaaagtag tcttgcaggc catataatat    26640
tcgacataac tataccactc cagtgatgga aatccataac ttatgatact tccgaatgaa    26700
cgtgtgtctt tcgtgtagat aagtccagtt cataaaatcc aatatacctc aataaaagct    26760
tcgtaaatca tccttgcatc agcaccctcc ccccgccccc tttgtttccc acgccttacc    26820
ggcatactca tgtaacctac aactcctttg tccgctcctc actctctgca atccaccttc    26880
tcaaactggt ctcatccctc ggcttaaaac caaccttgaa tggcttcggt tccgttgtca    26940
tcgatgtcgg agtagcgttg cactcaatag catcaagcac tggcatatcg gccgggtttt    27000
gagctggctc tatggtaaac gccacgataa accgaagaaa gaccgtgtat agctcgcggc    27060
tcgcgaggtg ggaggctgcg cacatgcgcg tcccggcgcc gaagctgtag tgaggggtgc    27120
cgaagccttc gctcggctcg aggtatcgct ccgggagaaa gcggttgggc atgtcgaaat    27180
gatcttcgtc gtagtttgct gcccacgcat tctgacagat caattagtcc aggaatgacg    27240
ggataggacg ccggggggtta ggggttaggg ggattgattt taccatgaaa aaggtcgttc    27300
cagcagggat cctcgcgcca ttatagatga cctccttgat attcacacgc ggaatgcaga    27360
taggcattac ggtccagaag cgcagggtct cttttcacaag tgcagtgata tagggcactt    27420
tttcctccac tagacaccgc tcccaggcgt cgccattcgg atacacggac ataatttctt    27480
cgtaagcctt ctgctgaatg cgttggccgt cttccgaaga caggtacgcg atgcccatga    27540
tcaagttgcc aggaacggta tcaagtcccg cagaaaccat ggtcagacag atagacttga    27600
tttccgctga gaaaggttag tatatataat cacaaatcat atagtggtgc atcgctcgtg    27660
aaatagacat accatctgta agcttcgtct cgggattctt cagaatattc cccgtaatgc    27720
acggcttatc tgtcccccttg gccatgcgat ccttcaaaat atcaaacaaa aaggccatgt    27780
acttatctct ccgcgcacgg agatgcttcg cctgattgct tctgttcgag aacaacctga    27840
gcagaggaac gtaatcctgc cagttgttgc tggttgaccg gagattggcc acgccgcgct    27900
gcacctcgca gatctctctg agaagctggt cgttcacatt gccctcgatg cggtagccat    27960
agttcagagt taaactggtg ttgagcgcaa accgctggaa gtagggagta gggttgatat    28020
ctatcttccc gccctgtgaa tctttcagca actccttaat actggccata ctctccagat    28080
cgattatggg catataggac tgcaccgcga cacggttgag cgctgtcgca gccgccttac    28140
ggcgccgttt acatgactca tcccacggtg acgttccgat cgtaaagccc tgtgagctag    28200
agacaacacc atgaaatgtg tgaaatgtag ggcgcgatat catcgaagac tgctccttaa    28260
tccacagctg gcgggtggac tcgaaggtgt tggcgaagat gacgcgccta ttgcccagac    28320
gcgcctggaa cacaggcccg aattccttttg accatttgcg agcgactgtg gcgtgtttga    28380
cacccagttg tatcagatta ccgaagatgg gcacgcctgg gatctcgggg attcccttaa    28440
tcttagggat gtcggttcgg ttgaagtagc gggtgaggaa gtagataacc gcggtagcgg    28500
cgatgacgat gatttggaga gtcatagtgg cgagatgcga atggtattga agaatagata    28560
```

```
gataattctt ttactcaggt tggcatggat tgtggcccgg gctttatact tcaaccctct  28620
atcgacatca ttccttaaag accaggatat tccgtcatag taacggcgat agtgacgcgg  28680
ccgcgttctg tcagcccgcg atcagctctg tcatgtggcc aatattctga tctacattgg  28740
tttcagactg atggtctggc tcgaatcgaa gcttcaaagg gctctcacaa cgctgcgttt  28800
ccgattatcg gtcctatctt ggtgcctacg gacacggcgg ccggcgacga tcgagcggac  28860
ggccggcacc cggcgatgga tctgatctgc cgcacatctt aatgataggt attaatggac  28920
ggctgatcta accttataag ctataacact tatggagagt cgaatgcaga gttgaaggag  28980
acgttggaag acaaacactg tagtatggcc gcctctaact agttcactga caagggtgct  29040
gtaacaggca tagactgtta ggacggatca acccgaccta agctgaccca ataccaagtc  29100
tacgggtac tttctgtaaa gaggctggag accgcgacgt tcaattattc caatctgttt  29160
ccaccactat cttatatgta taagttgtct tccctcggtt aacttgctct tcatgttaca  29220
tcttgtcact aataggcatt tgatgtttga tttggctatt gactattgac agaacctcct  29280
atgaatttcg ccttttcagtt gccgtcggtg gttgctgtcg ggccgactac ttgttgccgc  29340
tggtgattga atgctactta tatatatcca tgtctttttg tcggcttttta tcacgccact  29400
gccgccggat ttatccggta gaccctccta tcctgtcccc aaagcggggg aatgcgtcaa  29460
gatcttcggg gatgaaattt ccccgcatcc agctccctac ctatactaca cagttaccaa  29520
caattggcaa taaatagaca aacataacga acaaaaggca gctagaccgg atattaccgg  29580
gtaaacgggt ttgtaaattg gacatcctgg ctctctccag agctacttaa ggattgtctg  29640
ttggagaagc caaatgagaa agaggtgctt gtattagctt ccgaagcgcg tttctcgata  29700
cctaccctagt caatgcgcct ttcaaattgg ggctacatgc ttcttgaggg ttttatcagg  29760
accaacttcg atctgtccgt tgcaagaacc aagaaaccatt tccgccaaca aagcaaaact  29820
tgaccatgaa gcccgcaatc cttatgaaat actggctctt cgtctcagct gtgagcgcgt  29880
caaccctgaa cggcaagctc acattgagtg agacaaaggt gacggggggcc gttcagctgg  29940
cttgtaccaa tagtccaccg gacatctata tcgaccccga tgattcggtc tcagtggttc  30000
gcgcagccca cgatctggcc ctggactttg ggcgcgtctt tggtaaaaat gccacagttc  30060
gcttcactaa cgagactcat ccaacatcga tggccatcat cgctggtacc atagataagt  30120
caaccttcct tcagaggttg atagcggatc ataagctcga cgttaccagc atccgtggcc  30180
agtgggaatc ctattcatca gcactggtgt tgggtccagc caaaggcata cagaatgcgc  30240
tagtcatagc tggcagtgac cgtcgtgggg ccatctatgg cttatacgat atatctgaac  30300
aaattggcgt ctcgccattg ttctggtgga cggatgttac cccaaccaaa cttgatgcca  30360
tctacgcgct agatgttcag aaagtccagg gtccaccgtc agtgaagtat cgtggaattt  30420
ttatcaacga cgaagcgccc gccttgcata actggattct tgcaaattat ggcgaggttg  30480
agaacgggga ccctgccttc atctcacgtt tctacgccca tgtcttcgag ctgatcctgc  30540
gcctgaaagg gaattacctc tggccggcga tgtggtcaaa tatgttttat gttgatgaca  30600
ccaacaatgg cccactagcg gactactacg gagtggtaat gggcactagc cacactggta  30660
tgacggttgg gactccctgc ttgaaagccc atgctgacta cgaaaaagaa ccgatggctc  30720
gagcaacaaa cgagcaatcc cagtttctaa acggacgtg ggactggatt agcaacgagg  30780
tcaatgttaa agcatttatg agggagggtg taattaggag ccaacactgg gagaccgcat  30840
acacaatggg catgcggggt ctaggcgatg ctgcatcgcc gacacttaac gcaacagtgg  30900
aagaaagcat tgttagctgg caggaatccg tgctatcgga catcctgaat aaaaccaacc  30960
```

-continued

| | |
|---|---|
| tgtcgaacgt ggttcaacca tttgtcctat ttgatgttag gatccattca ccctcaaata | 31020 |
| tatcgtttgc tgactgccag gtctgtgaca caggaactgg gaacttacta tgagagcggc | 31080 |
| atgactgtac cagaccaggt cacattgata tatcctgatg acaatgcagg caatatgctg | 31140 |
| cgtctcccat tgcagaatga aactgggcgt tctggggcg caggaattta ctatcatttt | 31200 |
| gacatgaacg cgccgccgcg ctgttacaag tggatcaaca cagctcaact gatcaggacc | 31260 |
| tgggatcaac tgcgcgcggc atacagccac ggtgctcaga cagtatgggt tgccaatatt | 31320 |
| ggggatat | 31328 |

<210> SEQ ID NO 20
<211> LENGTH: 5053
<212> TYPE: DNA
<213> ORGANISM: Aspergillus terreus

<400> SEQUENCE: 20

| | |
|---|---|
| atggcgtctc tacttttctt tacggtgttc aatctaacac tggctcttct atcatctact | 60 |
| gccacaggag cagccgtccc tgtctcgcga cccacagacg attcgagata tatagacttt | 120 |
| gacgctgcta atggcgtcc aagagcaaaa cgagatgatg ccctgaaagt ccctctacgg | 180 |
| atcctcccct ttggcgcatc catcaccctg ggataccatt cctcaaccgg aaatggatat | 240 |
| cgcaaacctc tccgtgacaa acttcgcttt gaaggctggg aggtggacat ggtgggcagt | 300 |
| aagtccaacg gtgacatggt agacaatgta tgcatctctc ttccccccacc cctccgacag | 360 |
| atagacagac caattgacat ataaacgcgg gaaaaggatg tagaagccca cagcggcgac | 420 |
| gtgataacgc aagtgcaaac cgcggccgca aactcgctcg cctacaagcc gaacgtcgtg | 480 |
| ctgatcaacg ccggcaccaa cgactgcgac tacaacgtcg accctgcgaa cgccggcgag | 540 |
| cgcatgcgct ccctgatcga aaccctaatc ggcgccccgg acatggccaa cacgctcatc | 600 |
| gtcctgtcga ccctgatccc ctcgggttcc acaaccctcg aagctaacag gccctccgtc | 660 |
| aacgcgcagt tccgcgagct ggtccttgac atgcgcgagg cgcagaatgt ctccatcgtc | 720 |
| ctggccgata tggatccgcc ggctcccagc cccggaaaca actggatcac gtaccccgat | 780 |
| aacttcgccg ataacaagca ccccaacgac tacgggtact cccagatggc agacatctgg | 840 |
| tataacgcga tctacaacgc tgcggtggcg gagctcattg tcaagccggc ggaccttgac | 900 |
| atctcatcca cggggacctg tgacaaagag tacgggagcg gagtctacgc tggcgggttc | 960 |
| acgcagcaag ggagtggtga ggatgacgga atctatcgac acgacagcga gtatagcggg | 1020 |
| gcgttgttta ctgtccgcgc cgggaagggt gcagccgatc catacaagga tgacgacgag | 1080 |
| ctgcactttt tcttcgggag gctttatact agggcgtatg atgacatgat gatcttccac | 1140 |
| aaagataagg actccggcgc ggtgacgttt gtttcttaca cgaataatgt ccacactgag | 1200 |
| gagcaggagt ttacgaaggg ggggacgttc tcgactcata taattgtaa cccgggggt | 1260 |
| gtgcatttta tcgacatcaa cggtaagcac tgtgtctgtc tgccgaggaa ccatctggga | 1320 |
| ctgatttatg tgtgataaat gataggcgac ggacttgatg actacatctg catcgccttg | 1380 |
| gacgggacca cctacgcaag catcaacaat ggagacggcg acgccaagag caacaagcct | 1440 |
| ccatccttca ccgatatcgg actatggaag agtcccgaag gatacgatca ggcacatgta | 1500 |
| cgccttgctg atatcgacgg cgacggccgc gccgactact gcggtttggc tgacaacggc | 1560 |
| gacgtcacat gctggcgaaa tggatggatc gaagatatcc ccgcatactg gcagccgctg | 1620 |
| ggcaagcgct tcacggggaa agtcatggga gacctgcgcg gcgtgcgatt cgaggatatc | 1680 |
| aacggcgacg ggcgcgacga ctggatgtgg gttgatgacg atggcgctac gacaacatac | 1740 |

```
accaactccc ggagctgcat caaaggagag tctggtgacg ggttgaacgt cgtgtggcgc   1800 cagggggttct accaagatgc taactctggc ccgtcgcatc ccggaatggg agtaatattc   1860
gggacatccg gattacggga tcaggtctac tttgcgcgac tctatggcga ggtggcggat   1920
tttggagagc tcgggagaca ggactatgtg ttcatcaaga aggatacctc tgacaagtat   1980
tttgggccgc tgtattacgt tcatgtgtgg aagagcaagg gcgcaggagg ggctaagatc   2040
aaaggtatgg aaggaagttc tcatagagag gttgattgct aattgttata gccgacggag   2100
acaggtattg caatatgatg ggccacgaca atggtatgat ggactacatt tggatccatt   2160
caaccggcca tatgcgtctt tatccgaata ggggcctggt tgaagtcccc gccgacgggt   2220
cgagcttctg gggggcgaat gagattatct tcgaccccca agagcagatt ggcatgaagc   2280
ttgaccggcg cgatctgcat ctcgcagact gggacggcga cggagcctgc gatataatct   2340
ggacggatcc cgacaatctg aacagggccc aagtttggcg gaacaagatc aaagacacgg   2400
ggagttttga ctgggactac aatatcaatg ctgcagatga gctttactgc cccgagcacc   2460
gaggccttgg tttctttgac cggccggtcc attttgctga tgtttctggc aacggcaagg   2520
ccgattatct gtgcgttgag aaggacggcc gcacctgggg ctgggtcaat ggggacgatg   2580
gatgggacta cattgatcaa ttcaagtact ccgaggagaa ggacagggcg aatctacact   2640
gggccgacgt caacgcgac ggaaaggccg atatgatctg gacagacaag ttctcgggag   2700
atgggtcggt gtggtacaac cttggccaac gtgatatcaa gggatcgcga tacgaatggg   2760
gaccgcaggt tcccaagtac cgaggggcgg ttgaaggctc atgcacttat ttccctgatc   2820
tgaacggcga cggtcgtgca gacatgcaca gcatctggaa ctccataaac aacacagcgc   2880
agacgtggta caacgaatgt gccaccaaag accacacagg cgatgacggc ccgataacta   2940
accccaatct acctgtatct cctgtaaaag cccccatcga gctcacccct cattatcagg   3000
acaacagcga gtgcactagg gcccaggtgc agacgctctt tgaagaaatg caatatgcgc   3060
ttgatgctgc ctcggaagtt gcgtacttta gcggcggcgc atacgaccca tatagggaca   3120
tcttctttgc cgaatcactc accgacagct tgaccttcac tataaatgta aggtatacgt   3180
tcgaccggat ggtcaccatg atttctgggt cttcgcaatt cgacgacgaa aagttcacga   3240
tcacttgcaa aaaccttcgg ggctgtgacg agaacggctg gttggccatg atgaacaata   3300
ggaatcggct taatttctgc ccaaagttct tcacagatga gttgaagagt tccaggtcag   3360
tgctcgcgag gtgcgactca attaatcttc atgatgccca tctcactcga gccggggcga   3420
ttttgcacga agtaacgcat acggactatg ttatggagat tgtcaatgga gagaatgggt   3480
ggtatcacat attttttctc attcccaggc cgatactgat tctttcacct taggaggacc   3540
cgcgattatg tctatggatg gaaggagct cgagatcttg ccgcagggac cttcaatcga   3600
cactgtatcg aaagaggcag aaaggctgaa agagccgcta atgagctccg tatagccggc   3660
gatgctaact ggcaacgcag attgctttgc ccagacccaa ataacctcgg gcaagaaggc   3720
atctgtgaca gcaagttgtc cgcctacaat gcggattcat gggctcttgt cgtacttggc   3780
gggtactata ccaagatatg tggtcgacag attccccttc ctgaggagtc tgcttcttcg   3840
gcggatgact ccagctgtcc ggcctacgat gattcgtctt atgatgctga cactgtgtac   3900
ggcgtcaacg attatgttca cttcggtgac tcctacgccg ctgggatggg tacaggaacc   3960
acaaccggtg acagttgccg cgtgggaagt aacagctacg gaaagctcgt ccaggagtgg   4020
tttgatactg aggatttcac ttataccaac tatgcgtgct ctggagatac aacggttggg   4080
ctgaataaaa agatcgacca gtggctagga caggacccca cggggactac catggcaacc   4140
```

-continued

```
ctgacaattg gagggaacga tgtgttcttc agcgatctgg tttccaactg cgtgctaaca      4200
atgtggtggt actcgcttga gcaataccgc cagtggtgtc tggagactga agagaaagcc      4260
cgcaacctga tgcaggatac agggtctgac ggactcggct cgaaacttag ggctgcgtat      4320
gaaaagatcc tggatagatc tggctctagc gtatatctcc ctgttatcct tatttattcc      4380
tgtcgtgctg tccttcgtcg cgctgacttt actttagtcg ttcaacctct acgtccctgg      4440
ctatgtcacc ttcttcaacg aagacaccac cgactgcgac tcaaccacct tctggtacga      4500
aagcccacac tacgacccgc agcaatccgg caactatgtg tggctcacga ccgacctacg      4560
caaggaactc aacgacctcg tccgcatgct caactcgtta atccaatcca ccatttccga      4620
catcaacacc gcccggaata cggagcagat ccattacatc gatatggacg cgcgatttga      4680
cggccaccgc tggtgcgagc ccggaaccca agaaccagac cccgacaacc caaacactta      4740
cttcttccta tccgcatggc ccgatatcgc gattgttgga gacacgacag ccgagagcac      4800
gaacgcgacc gagacagacg aaattaccgc gcttatgaac tccggatcga tccagctgcc      4860
cgatgcggat acgtgccagg atgcgctggg atctgacccg gatccctatg cggttttcat      4920
gtgtgacgtt gcggtccacg tcaaggcgaa ctcgtcgagt ttgatcgcgc agagcttgga      4980
ccgagcgaat caggccattg ccaatagggg ctatagtagc caggatgtct cttggtggtt      5040
gcctagtccc tag                                                         5053
```

<210> SEQ ID NO 21
<211> LENGTH: 987
<212> TYPE: DNA
<213> ORGANISM: Aspergillus terreus

<400> SEQUENCE: 21

```
atgactctac caacacttcc taactggata aggatgtgcg tgcatttgtc ccttacacat        60
ctccatcagc accgttcccc gaaatacgag tctatacccta ttaaaagtat ccaggctaat      120
tcacacagaa tcctcatcat cctaaccaca gcctccttct acccgcagat ccggtgcatc      180
caacttcgaa actccacgca cggcatctcc actgcctaca tcctcttcaa cctaatcagc      240
gcaacagaac acttcaccat cctattcgca ttgctggtaa acagcggcgg agatgtcctc      300
atccatgagc cccccacgac cggcgacggg ttgaacctgt accagctttt cgcagtgtgg      360
atgggatgct tagtcctctt ctgccaagca atccatagcc tccacgccaa tccacgccgc      420
aaactcatcc tactaaccat atacattcaa tacctatgca tttctatctt accagaggtc      480
atcgacgcaa tcaccactcc cgaggaaacg agaaaacaaa ggccgccaac gggcgagagg      540
aactggctga tcggactctt tctttccgcg cacgcgatga ccgtcctgcc actatcggcc      600
gtgctccgca tcgcgggatt catagatcag tcgcgactga tctcgcggcg cagacgggag      660
cagccatcgg tcttaagcct gacaggcctg gcgtgtcagg ccgtggtctt tgctctagtt      720
tctggactct gggactcag ggttcagcag cctgttcctc gaatgccgat gagaagacct      780
gtggattgga tgtattggta ccatgtaatt gggtggccgg ttgtcgacga tgcggtttat      840
gcgctgggac aatgggtttt gttttggtat gcggtttgtt ggcgttctcg gggcgatgct      900
agggatgaag cagtccatgc tggggagact gatgacctgt taggagagga tgaagggcat      960
gggtacggcg gaaccgggac ttcttag                                          987
```

<210> SEQ ID NO 22
<211> LENGTH: 972
<212> TYPE: DNA
<213> ORGANISM: Aspergillus terreus

<400> SEQUENCE: 22

```
atggtcggga gcaagttagc ccataatgag gagtggcttg acatcgccaa gcaccacgcg      60
gtgacgatgg caattcaagc gcgccagctg cgcctctggc ccgtcattct gcgccccctt     120
gtacattggc tcgagcccca gggagccaaa ctccggggcgc aggttcgacg agcccggcaa    180
cttctcgatc ccattatcca ggagcgacgt gcggaaagag atgcctgccg ggcaaagggc     240
attgagccgc ctcgctacgt agactcgatc cagtggttcg aggatactgc caaggggaaa     300
tggtacgatg cagccggggc gcaactggcc atggactttg ctggtatcta cggaacctcc     360
gacctgctga tcggtggggtt ggtggacatc gtccgacatc cccatctcct tgagcccctc    420
cgtgatgaga tccggacggt catcggccaa ggggggttgga cacctgcctc gctgtacaag    480
ctcaaactgc tggatagttg tctcaaggag tcacagcgcg tcaagcccgt cgaatgtgcc    540
accatgcgca gctatgcatt gcaggatgtg actttctcca atggaacctt tatcccaaaa    600
ggagagctgg tggcggtagc tgccgaccgc atgagcaacc ccgaggtctg gccagagccg     660
gcaaaatacg atccttaccg gtatatgcgc ctgcgagagg accggctaa agcgttcagt      720
gcccaactgg agaacaccaa cggggaccac atcggcttcg gttggcatcc acgggcttgc     780
cccggccggt tctttgcctc taaggagatc aagatgatgt tagcctactt gctcatacga    840
tacgactgga aggtggtccc cgacgaaccg ttgcagtact accgccattc tttcagcgtg    900
cgcattcatc ccaccacgaa gctcatgatg cgccggcgcg acgaggatat ccgccttcct    960
ggttcactat ag                                                          972
```

<210> SEQ ID NO 23
<211> LENGTH: 771
<212> TYPE: DNA
<213> ORGANISM: Aspergillus terreus

<400> SEQUENCE: 23

```
atgcgttacc aagcatctcc agcgctggtg aaggcgcctc gagcgcttct ttgcatccat      60
ggggctggct gctctcccgc catcttccgc gtgcaattgt ctaagctccg ggctgcgctg    120
cgcgaaaact ttgaattcgt ctacgtgaca gctccgttcc cttcctctgc agggcctggg    180
attctccccg tcttcgccga cctagggcca tattactcct ggtttgaaag cagcagcgac   240
aacaatcata atggaccctc cgtgagcgaa cgcctcgccg ccgtccacga ccccatccgc   300
cgcaccattg tcgactggca gactcaacac ccccacatcc ctatcgtggg tgctatcggt    360
ttctccgaag gtgccctggt gacgaccttg ctcctctggc agcagcagat gggtcacctg   420
ccctggttgc cccggatgag tgttgcgctg ttgatctgtc cctggtatca agacgaggca   480
agccagtata tgaggaacga agtgatgaag aaccatgacg acgacaacga cagcaaagat   540
accgagtggc aggaggaact ggtcattcgg ataccgacat tacatctgca gggtcgcgat  600
gattttgcgc tcgcaggatc gaagatgctg gtggcgcgcc atttctcccc ccgagaggcg   660
caggtattgg agtttgctgg gcagcatcag tttcccaatc gaccgcgcga cgtgttggag   720
gtcattaatc gttttcgtaa gctgtgtgtg acggcccaga cattggagta g             771
```

<210> SEQ ID NO 24
<211> LENGTH: 1253
<212> TYPE: DNA
<213> ORGANISM: Aspergillus terreus

<400> SEQUENCE: 24

```
atgggcgacc agccattcat tccaccaccg cagcaaacag cgctgacggt aaatgaccat    60
gatgaagtca ccgtctggaa tgccgcaccc tgccccatgc tgccccgcga ccaggtatac   120
gtccgcgtcg aggccgtggc gatcaatccc agtgacacga agatgcgcgg acagtttgcc   180
acgccctggg cgtttctcgg aacggactat gccggcacgg tcgtcgcagt gggttcggac   240
gtgactcata tccaagtggg tgaccgggtc tacggggcac agaacgagat gtgcccacgc   300
accccggatc aggggcatt ctcgcagtac acggtcacgc gaggccgtgt ttgggccaag    360
atccccaagg gcttgtcgtt cgagcaggct gccgcgctac ctgcgggcat cagtaccgct   420
ggattggcga tgaagttgct tgggctgcct ttgccatcgc cttcggcaga ccagccaccc   480
acccactcca agccggtgta tgtgttggtc tatgggggca gtacgccac tgccactgtc    540
actatgcaaa tgctccgcct gtaatgcttc ccttgtcctg agactttct ctccgttggt    600
cgtgggctgt acaagcgatg gttatactaa gatccgctgg caggtccgga tatattccaa   660
ttgcaacatg ctcccccccac aatttcgacc tggccaaatc gcgcggcgca gaggaggtct   720
ttgactatcg ggccccgaat ctcgcgcaga cgatcgtcag tgaaccccctg ccaccgctct   780
accccctccca gtccactttg gccttacaga acagactatt gatattcttc tagcgtacct   840
acaccaagaa caatctccgc tatgctctcg actgtatcac caacgtcgag tccaccacat   900
tctgcttcgc agccatcggc cgcgcggggg ggcactacgt ctccctgaac ccgttccctg    960
aacacgcggc cacgcgcaag atggtcacga ccgactggac cctggggccg accatctttg  1020
gcgagggatc aacctggccc gccccctatg gcgtccccgg cagtgaggaa gagcggcagt  1080
tcggcgagga tctgtggcgc atcgcggggc agctcgtcga agatggacgc ctcgtccatc  1140
atccgttgcg cgtggtgcag ggcggcttcg atcacattaa gcaaggcatg gagctcgtcc  1200
ggaagggaga gctgtcgggg gagaaactcg tggttcggct cgaggggccg taa         1253
```

<210> SEQ ID NO 25
<211> LENGTH: 1394
<212> TYPE: DNA
<213> ORGANISM: Aspergillus terreus

<400> SEQUENCE: 25

```
atgggatcca tcattgatgc tgctgcggca gcggatccgg ttgttctgat ggaaaccgcc    60
ttccgcaagg ccgtgaaatc caggcagatc cccggggcgg tcatcatggc ccgagattgc   120
agtggtgaga gaccccaatc ggaccccttt gcgacaatta caagcacacc gagacgaatg   180
acagcgggac ataccctaggc aatctaaatt atacgcgctg cttcggggct cggacggtgc   240
gacgggacga gtgcaatcag ctgccgccgc tacaggtcga caccccctgc cggctcgcca   300
gtgcgaccaa gctgctgacc acgatcatgg ccctacaatg catggagcgc ggtctcgtgg   360
acttggatga cacggtggat aggctgcttc cggatttgag cgcgatgccc gtgctggagg   420
ggtttgacga cgcgggaaac gcaagattgc gagagcgtcg gggaagatc acgctgcggc    480
acctgctgac gcatacatcg ggactgtcgt acgtcttcct ccatccgttg ctccgggaat   540
acatggccca gggccaccct cagtcggcag aaaagtttgg catccagagt cgcctggcgc   600
cgccggccgt caacgaccct ggggcggagt ggatctacgg cgccaacctg gactgggcgg   660
gtaagctcgt cgagcgggcc accggcctcg acctggagca gtacctgcag gagaatatct   720
gtgcgccgct gggcatcacc gacatgacct ttaagctgca gcaacggccg gatatgcttg   780
cgcgccgggc cgaccaaacg caccgcaact cggcggatgg gcgcctgcgc tacgacgact   840
```

-continued

```
cggtctactt ccgggccgat ggagaggagt gcttcggcgg ccaggggtg ttctcgggcc      900
ctgggtccta tatgaaggtg cttcactcgc tgttgaagcg agacgggctc ctgctgcagc      960
cacagaccgt ggacttgatg tttcagcctg ccctcgagcc gcgactcgaa gagcagatga     1020
accagcacat ggacgccagc ccacatatca actacggtgg gccgatgccc atggtccttc     1080
gtcgcagctt tgggctgggg gggatcatcg ccttggagga tctggacgga gagaactggc     1140
gccgaaaagg ttccttgacc tttggggtg gcccaaacat tgtgtgggta agctcggctc     1200
ctagattcct ttggtttatg tcaccttcaa tgttgatcca gcctactaag tgctattgta     1260
attagcaaat cgaccccaaa gccggcctgt gcacccttgc gttcttccaa ctggaaccct     1320
ggaatgaccc ggtctgtcgt gatctgacac gcacattcga gcatgccatc tatgcgcagt     1380
accagcaggg ttaa                                                      1394
```

<210> SEQ ID NO 26
<211> LENGTH: 3504
<212> TYPE: DNA
<213> ORGANISM: Aspergillus terreus

<400> SEQUENCE: 26

```
atggatccgg tggttagaaa gccggaccct ggcggggtgc agcatcgagt gaccaaagca       60
ttgcgtgcca ttgtgggaca cgcgtgtcga catcccattc acactctgct agtcacggcg      120
ctgaccgcgg caacgaccca tcttcatgtg ctggaaggga catatcaggc tactcacaga      180
ggtctggccc cctgggccaa ggaaaccccc ttgaacgtcc agtcatttct ctggggaagc      240
cgcactgtta gcctgggaga ggctagcgca tggaaatggc agatagacga ccgacctaag      300
gtgccgagg atggccaggt atgatagatc tcctgcgctc cattggtccg agaaattctg      360
cgtgctgacc ggaccgtccc tgtgctactc tcaattagtc tgactttcac tgggctcttg      420
tcaccctcga tctaccgggt gcgtctgtcg acgccagtat ccccttccta tcaaacacgc      480
tctcagggtt cctcggtgcg aacagacca cgcccacccc cgattcatcc ccctcacccg      540
atcattccgc gttgacgttt cgagttccct actcccaact agatggcttt ctacaggctg      600
tcgaaattat accctcggaa aaagaggatg atagttggag actgaggtct cctcgcgaag      660
aaggaagtcc caggtcactg ggacactggc tcggaagctc atggctgtca ttccttcatc      720
gtgttcacca tgcggagaca gtcgacttgg tgatcatagg gctcagttac ctagccatga      780
atatgactgt ggtctctctc tttcgggtga tgcgccacct cggctcacgc ttctggttgg      840
cagcctcggt cctgctgtct ggtgcctttg cttttgtact cgggcttgga atcacgacta      900
catgcgacgt gcccgtcgac atgcttcttc ttttcgaagg aatcccgtac ctcgttctga      960
cagtgggctt tgagaagccg atccaactaa cccgtgctgt tctctgcgtg tcggaagaac     1020
tgtggggcgg ggggcagcgg caagttccca atggcgccag cagtgatgat agccggcaaa     1080
accaattgat tcctaacatc atccaactcg cggttgatcg agagggtgg tatattgtgc     1140
gatcttacct cctggaaatc ggcgcgttgg cattagggc ggtccttcgg ccaaaggata     1200
gtcttggcca tttttgcttc ctgcggcat ggacactcct gattgatgcc gttctacttt     1260
ttaccttcta tgccaccatt ctttgcgtga attagagat cacgcgaatc cggagcccag     1320
gagggcttgg tcaagttaat gccaagcatc ttcggggat ttttgggcac aaggtcaagt     1380
cgacaaacat cacctggtgg aagctattga cggtgggcgg cttcgttcta tgtcacttcc     1440
tccaattgtc gcccttcttc tatcgggtca tgggagaata tatggctaat ggtactctgc     1500
cccctactgc tgtcagtcct ttcaaagaag cggccaacgg actcaacgag atctacctaa     1560
```

-continued

```
cggcgcgcgt cgaggggttt gagacacgcg taaccgttct gccgccactg cagtacgtct    1620
tggaatcagc tgggttcaat atatcagcca ctaaacgttc tacatttgac ggtgtgctcg    1680
atggattgga agcccgctg gtcgactat gtctcatggg cgcattggtc gttagcctgg     1740
tcctcaacaa ccacctgatc cacgctgctc gctggcatgc ttggcccaa gcgagagagt    1800 ccgccgtccc tgatggctcc tacttgtcgg tgccatgctc tgccactgcc cctgaagtct    1860
gtactcgccc ccagaagaa acagaggccc tcctcaaatc gaaccaagca gaatctctga    1920
cggacgacga gctggtggaa ctgtgtctcc ggggtaagat cgcggggtac agtttagaga    1980
agactctcga gcggattgcg gcgggatcat cccgctcggt gacccggctg gaggcattta    2040
cgcgtgccgt gcggattcgc cgtgccgctg tgtcgaaaac gccctccact cagaacctct    2100
gcagcggcct ggcggagtca ttgctccctt atcgcgacta taactacgag cttgtgcatg    2160
gcgcctgctg tgagaacgtg gtcgggtacc tgcctctgcc cctgggagtg gccggaccca    2220
tggtgatcga tggacaggcg ttgttcattc ccatggccac aaccgagggc gtgctcgttg    2280
cgagcgccag tcgcggatgc aaagcgatca atgctggcgg cggtgccact accatgctca    2340
aaggtgatgg tatgacgcgt ggtccctgtc tgcgattccc gtcggcccaa cgtgcagctg    2400
aagcccagcg ctgggttgag tctcctctcg ggcacgaggt tctggcggcc gccttcaacg    2460
cgaccagccg gtttgcgcgg ctccaaaccc tgacggtggc ccaggcgggc atctatctct    2520
acatccggtt ccgcaccacc acgggcgacg cgatgggcat gaatatgatt tcgaagggcg    2580
ttgaaaaagc cctggaggcg atggccgccg agggtggatt tcccgacatg catacggtta    2640
ccttatctgg caatttctgt tccgacaaga atccgccgc cattaactgg atcggcggcc    2700
gcggcaagtc cgtcatcgcc gaagccacga tccccgcgga gactgtccga caggtcctga    2760
agaccgacgt cgatgcgctg gtcgagctca acacggccaa gaacctggtc gggagtgcca    2820
tggcgggcag cctgggcggc ttcaacgccc atgcctccaa cctcgtccag gcggtgtttc    2880
tggccactgg tcaggatccg gcgcagaatg tggagagcag tagttgcatt acgaccatga    2940
aaaagtaggt agcttctcta cgttttgatt ttctcctccc ggtttatatat attcacgtgg    3000 gtgtgtttgc taatggtggg tttctagcat cgatggaaac ctgcacatcg ctgtctcgat    3060
gccctcgatg gaggtcggca cgattggcgg aggcaccatt cttgaggccc agggagccat    3120
gttggacttg ctaggtgtcc ggggcgcaca ttccacggag cctggcgcca atgcgcgccg    3180
cttggcccgc attgtcgccg cggccgtgct ggctggcgag ttaagtacct gcgcggctct    3240
tgcggcgggt cacttggtca atgcccatat gcaacacaat cgcagtgcgg gtgccacagt    3300
caagaaatga agggatcgct gtgattgatt ctcggggcag cttcaaagga cgctatctcc    3360
ggtacagagt acgagcaat tagaacaccg gtatatgtgt taatcttaga acatgcggga    3420
gacatccatt tcgtgcaaat cgaatataaa aataccacc tacgtagaaa agtacctacc    3480
ttgtcatgta acttaggtag gtaa    3504
```

<210> SEQ ID NO 27
<211> LENGTH: 1512
<212> TYPE: DNA
<213> ORGANISM: Aspergillus terreus

<400> SEQUENCE: 27

```
atggctgcag atcaaggtat attcacgaac tcggtcactc tctcgccagt ggagggttca      60
cgcaccggtg gaacattacc ccgccgtgca ttccgacgct cttgtgatcg ggtcatgca     120 caaaagatca aatgtactgg aaataaggag gttactggcc gtgctccctg tcagcgttgc    180
```

-continued

| | |
|---|---|
| cagcaggctg gacttcgatg cgtctacagt gagcgatgcc ccaagcgcaa gctacgccaa | 240 |
| tccagggcag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgc cggtgtcgca ggaactggaa gagatccttc tggccgtgac ggtagaatgg | 660 |
| ccgaagcagg aaatctggac ccgtgcgtcg ccgcattccc caactgcttc ccgtgagagg | 720 |
| atagcacagc gccgacaaaa cgtatgggca aactggctaa cagacttgca tatgttctca | 780 |
| ctagatccca tcggaatgtt tttcaatgcg tcacgacggc ttcttactgt cctgcgccaa | 840 |
| caagcgcagg ccgactgcca tcaaggcaca ctagacgaat gtttacggac caagaacctc | 900 |
| tttacggcag tacactgtta catattgaat gtgcggattt tgaccgccat atcggagttg | 960 |
| ctcctgtcgc aaattaggcg gacccagaac agccatatga gcccactgga agggagtcga | 1020 |
| tcccagtcgc cgagcagaga cgacaccagc agcagcagcg ccacagcag tgttgacacc | 1080 |
| ataccttct ttagcgagaa cctccctatt ggtgagctgt tctcctatgt tgaccccctg | 1140 |
| acacacgccc tattctcggc ttgcactacg ttacatgttg gggtacaatt gctgcgtgag | 1200 |
| aatgagatta ctctgggagt acactccgcc cagggcattg cagcttccat cagcatgagc | 1260 |
| ggggaaccag gcgaggatat agccaggaca ggggcgacca attccgcaag atgcgaggag | 1320 |
| cagccgacca ctccagcggc tcgggttttg ttcatgttct tgagtgatga aggggctttc | 1380 |
| caggaggcaa agtctgctgg ttcccgaggt cgaaccatcg cagcactgcg acgatgctat | 1440 |
| gaggatatct tttccctcgc ccgcaaacac aaacatggca tgctcagaga cctcaacaat | 1500 |
| attcctccat ga | 1512 |

<210> SEQ ID NO 28
<211> LENGTH: 2161
<212> TYPE: DNA
<213> ORGANISM: Aspergillus terreus

<400> SEQUENCE: 28

| | |
|---|---|
| atgacatccc accacggtga aacagagaag ccacagagca cacggctca aatgcagata | 60 |
| aatcatgtca ctggcctcag gctaggcctg gttgtggttt cagtcactct ggtggcgttt | 120 |
| ctgatgctct tggatatgtc catcattgtc acggtcagca tggcaccagc ctggagattg | 180 |
| ctccgagcct tggagacaac tgactcttca cattcgcagg cgattcctca cattaccgcc | 240 |
| cagtttcatt ccctgggcga tgtcggatgg tacggaagtg cgtatcttct atcaaggtga | 300 |
| tcgattttcc aacccatgcc ctcttccttt ctccagccg ggtttctatt gactccacga | 360 |
| cacgctctag ctgtgccctc caacccttgg caggcaaact atacactctg ttgaccctga | 420 |
| aatacacctt cctcgctttt ctcgggttgt ttgagattgg atcggttctt tgcggcactg | 480 |
| ctcgttcgtc aaccatgttg attgtagggc gagcagtggc cggaatggga gggtcggggc | 540 |
| tcaccaatgg cgcaatcacc attctgtcgg cggcagctcc aaagcaacag caaccgcgta | 600 |
| agtactgata gccagaccta tctcaaccgt tgttatgcta tgctgacccg gatatttaca | 660 |
| catagtcttg attgggatca tgatgggccg tcagttcgcc aacccattgg gatccccgga | 720 |
| aatcatcaag catagtttct gactccattc ccagtaagcc aaatcgccat tgtatgtgga | 780 |

-continued

| | |
|---|---|
| ccgttgcttg ggggtgcttt cacgcagcac gcaagttggc ggtggtgtat gtatccccat | 840 |
| tggatttatc ggttcagtgc ttgctttctc aaaggacctt ggctacgact ccgccacgtc | 900 |
| aagatctttc gctcacggtg attctggtcc aggtttttac atcaaccttc ccattggggc | 960 |
| gtttgccaca tttctccttc tcgtcatcca gatccccaac agattgccat ccacgtcgga | 1020 |
| ttcaaccaca gacggcacaa accccaagag aagaggggct cgggacgtct tgacccaact | 1080 |
| ggatttcctt ggattcgtgc tcttcgccgg ttttgcgatc atgatatctc ttgctttgga | 1140 |
| gtggggtggg tctgattatg cgtggaatag ttccgtgatc atcggcttgt tctgtgcggc | 1200 |
| gggcgtgtcg ctggtgctgt tcggatgctg gaacggcat gtcggcggtg cagtggccat | 1260 |
| gattcccatt tccgtggcca gtcgtcgcca agtctggtgc tcctgcttct tcctcggctt | 1320 |
| ttttccggg gccctactta ttttctccta ctacctgcct atctacttcc aggcggtcaa | 1380 |
| gaatgtttct cccaccatga gtggagtgta tatgctgccg ggcattggtg gacagatcgt | 1440 |
| catggcgatt gtgacgggtg caatcagttg agttgccacc attccaccac ctttcttcgc | 1500 |
| ttataaccta tggcgttact gacaaattga gggtggtagt cggtaaaaca ggctattacg | 1560 |
| ttccgtgggc gctcgcaagc gggatccttg tgtccatatc cgccggactg gtatcgacct | 1620 |
| tccagccgga aacctcgatt gcagcatggg tcatgtatca gttcctggga ggcgtgggcc | 1680 |
| gaggatgcgg aatgcaaacc gtaggtgacc tggatcgttt ccatcggttt cgccgcact | 1740 |
| cttatgcaaa tgctcattga ctcggttgtc cctcctttag cctgtcgtcg ccattcaaaa | 1800 |
| tgcgctgcct ccacaaacga gccccatcgg catttcgcta gccatgttcg gccagacatt | 1860 |
| cggtggctcg cttttctca ccctgaccga attggttttt agcaatggtt tggactctgg | 1920 |
| tctgcgccaa tatgcgccaa ccctcaatgc acaggaggta acagccgcag gggccaccgg | 1980 |
| cttccgccaa gtggtccccg ctcctctcat ctctcgggtc ctcttagcat acagtaaagg | 2040 |
| cgtggaccat gcattctacg ttgcggtcgg tgcgtctgga gctaccttca tcttcgcctg | 2100 |
| gggtatgggc cggcttgcct ggagaggctg gcggatgcag gagaaaggac ggagcgaatg | 2160 |
| a | 2161 |

<210> SEQ ID NO 29
<211> LENGTH: 8035
<212> TYPE: DNA
<213> ORGANISM: Aspergillus terreus

<400> SEQUENCE: 29

| | |
|---|---|
| atgacaccat tagatgcgcc cggtgcgcct gctcccatag ctatggttgg catgggctgc | 60 |
| agatttggcg gaggcgcaac agatccccag aaactgtgga aattgctgga ggaaggaggg | 120 |
| agcgcctggt ctaagattcc tccttcacga ttcaatgtcg gcgggtcta ccaccccaat | 180 |
| ggccagcggg taggatcggt gagtatgaag gattctgggt tgagcatttt tgaggcccat | 240 |
| atcttcctgt tcagaacgat aggcgttgac tgcgagtaga tgcacgttcg cggtggacac | 300 |
| tttctcgacg aagacccggc tcttttcgat gcctcatttt tcaatatgag tactgaagtt | 360 |
| gccagtgtac gtcccgcgat cgttgtccag ttgtgtatgg atcagaagcg gaataaaccc | 420 |
| atgctaagac tgccgaatag tgtatggacc cccagtaccg actcatactt gaagtcgttt | 480 |
| atgaggcgct cgaagctggt atgtattata ttccttggtt tccacgtgg gtattaactc | 540 |
| cccatggctc cgcagcggga attcctctcg aacaggtctc cggctccaag actggggttt | 600 |
| ttgcaggaac catgtatcac gactaccaag gctccttcca cgccaacca gaagcccttc | 660 |
| cacggtatt cataacagga aatgctggca ccatgctcgc gaatcgcgtc tcccactttt | 720 |

```
atgaccttcg tgggcccagt gtctcgatcg acactgcctg ttccacaacc ttaacagcct    780
tgcatcttgc cattcagagc ttgcgagctg agaatctga tatggcgatt gtcgctggcg    840
cgaacctgct acttaatcct gacgtcttta ctaccatgtc caaccttggg tgagtctggt    900
gttcaatcca tctagtgatc agcattcttg ttgcacagac aatatgtgat gttaactgtg    960
atgtgctgcg accagcttcc tttcgtccga tgggatttcc tactcatttg actcgagagc   1020
ggatggctat ggtcgcggag aaggagtggc tgcgatcgtc ttgaagactc tgcccgatgc   1080
ggtgcgagac ggagacccga tccgcctcat agtgcgcgaa acggcaatca accaagacgg   1140
ccggacccca gccatcagca cgccgagcgg cgaggcccag gagtgcctga tccaagattg   1200
ctatcagaag gcccagttgg acccaaaaca gacttcgtac gttgaggccc atgggacggg   1260
aaccagagca ggagatccgc tggagcttgc agtcatctcg gccgcgtttc cgggacagca   1320
gatacaggtg ggctccgtga aagccaatat cgggcataca gaggctgtca gtggtctggc   1380
gagtttgata aggtggctc tggctgttga aaggggggtt atcccgccta atgcaaggtt   1440
cctccagccg agcaagaagt tgctcaagga cactcatatc caggtagcat tatcttcacg   1500 atttttcct ctcattctat tctttctatt ccagctcctc gctgatttac aaacagattc   1560
cactgtgtag ccaatcatgg ataccaaccg atggtgtccg tcgcgcatca ataaacaact   1620
tcggtttcgg aggcgcaaat gctcatgcaa tcgtggagca atatgcccg tttgcagaaa   1680 catcgatctg cccacctaat ggttattctg gcaactatga tggcaattta ggaacggatc   1740
aagcgcatat atatgtgctg agtgccaagg atgagaacag ttgcatgaga atggtttcaa   1800
ggctgtgcga ctatgctacc cacgccagac cagccgacga tttgcaattg ctcgcgaata   1860
tagcatacac gcttggttct cgtcgctcga acttccgatg gaaggcagta tgtacggcac   1920
acagcctcac gggtcttgcc cagaatttgg cgggagaagg catgcggcca agcaagtcag   1980
ccgaccaagt aagactggga tgggtgttca caggccaggg agcgcaatgg tttgcaatgg   2040
gtcgtgagtt gattgagatg tatcctgtct ttaaagaggc cctgctggaa tgcgatggat   2100
atatcaagga aatggggtca acctggtcca ttataggtaa agacccgcaa caagtccccg   2160
gcccaggcta tggaaagcac tcactcatgt caccattgca gaggaactca gtcgccctga   2220
aacggaaagt cgcgttgatc aggcagaatt cagtctgcca ttgtctacgg ctcttcaaat   2280
tgcgcttgtt cgtctgctct ggtcgtggaa catccaacca gtagccgtca ctagtcactc   2340
cagcggagag gcagctgcag cgtacgctat cggggcacta acagcccgct cggccattgg   2400
aataagctat atacgcggtg cattgacagc aagagaccgc ctggcgtcgg tacataaggg   2460
gggcatgttg gctgtcggat tgagccgcag tgaagtgggt atatacatca gacaggttcc   2520
attacagagt gaagaatgct tggtggtggg gtgtgtcaac agcccgtcga gtgtgacggt   2580
ctcgggagat ttgtccgcca ttgccaagtt ggaggaactg ctccatgctg atcgtatatt   2640
tgcgagacgc ctgaaagtca cccaagcctt tcactccagc acatgaact cgatgacaga   2700 tgctttccga gccggtctta cagaactctt cggagcagac cccagtgatg cagcaaacgc   2760
cagtaaagat gtgatctacg cttctcccag aaccggggcc cgcctgcacg acatgaatcg   2820
tcttcgggat cctatacact gggtcgaatg catgcttcac ccggttgagt tcgaatcagc   2880
attccgtcga atgtgcctgg acgaaaacga ccacatgcca aaggtcgata gggtcattga   2940
gattggacct cacggagcgc ttggaggccc gatcaagcag atcatgcagc ttccagagct   3000
tgccacgtgt gacatccctt atctgtcctg tctttctcgt gggaagagct ctctgagcac   3060
ccttcgcctt ctcgcatcag aacttatccg ggccggattt cctgttgact tgaatgcgat   3120
```

-continued

```
caactttccc cgcggatgtg aagcagctcg ggtccaagtg ttgtctgatc taccgcccta    3180
cccttggaac cacgagacca gatactggaa agagccgcgc atcagccaat ctgcccggca    3240
gcggaagggc ccagtccacg atctgatcgg attgcaggag ccgttgaacc tgccgttggc    3300
gcggtcatgg cacaatgtgc ttcgtgtgtc agatttgcca tggctacgcg accacgtcgt    3360
cggctcgcat attgttttcc ctggggctgg gttcgtgtgt atggcagtga tgggaatcag    3420
cacgctctgc tcgtccgacc atgaatctga cgacatcagt tacatcctac gcgacgtgaa    3480
ctttgcgcag gccctgattc tacctgcgga cggggaagaa ggaatagatc tgcgcctcac    3540
gatttgtgct cccgatcaga gtctgggttc acaggactgg caaagattct tagttcattc    3600
gatcactgct gacaagaatg actggacgga acactgtacg ggacttgttc gagcagagat    3660
ggaccagcct ccctccagtt tgtcgaacca acaacggata gacccacggc catggagccg    3720
taaaacggcg ccgcaggagc tgtgggactc actacatcgg gtgggaattc gtcatgggcc    3780
cttttttcga acattacgt gcatcgaaag cgacgggcga gggtcatggt gtacatttgc     3840
catcgcggac acggcctccg caatgccaca cgcctacgaa tcccagcaca ttgttcaccc    3900
aaccacacta gactctgcag ttcaggcagc ctataccact cttccattcg ctgggagccg    3960
gatcaaatct gcgatggtcc ccgctcgcgt cggctgcatg aagatttcct cccgacttgc    4020
agatttggag gccagggaca tgctgcgcgc acaagcgaag atgcacagcc aaagtccttc    4080
cgcattggta accgatgtag cagttttga tgaggcagat ccggttggag ggcctgttat     4140
ggagctcgaa gggctggtct ttcagtctct gggggcaagt ctgggcactt ctgaccggga    4200
ctccaccgac cccgggaata cttgcagctc ctggcattgg gctccagaca tcagcttagt    4260
taacccggc tggcttgaaa aaccctgggg cacaggtatt caggagcacg agatcagcct     4320
catattggag cttcgacggt gttcggtgca cttcattcaa gaggccatgg aaagtttgag    4380
cgtaggcgat gtcgagaggc tgagtggtca tctggccaaa ttctatgcgt ggatgcagaa    4440
acaactggcg tgtgcccaaa atggcgagct ggggccagag agctccagct ggactcggga    4500
tagcgagcag gcaagatgca gcctccgctc tagagtggtt gctggtagca ccaacggcga    4560
aatgatctgt cgcctgggct ccgtgctccc cgctatccta cgtcgggaag ttgatccgtt    4620
ggaggtgatg atggatggcc acctgttgtc ccgctactat gtcgatgccc tcaagtggag    4680
tcggtccaac gcgcaagcca gcgagctcgt gcgcctctgc tgccacaaaa cccgcgcgc    4740
tcgcatactg gaaatcggcg gaggcaccgg gggttgcacc cagctggtcg tggactcctt    4800
gggcccaaat ccgccggtag gccgctatga ctttactgac gtctcggccg gtttttttga    4860
agcagcccgc aagcggttcg cgggatggca gaatgtgatg gattttcgga agttggacat    4920
cgaggacgat ccagaagcgc aggggtttgt gtgcggatcc tacgacgtgg tgttggcttg    4980
tcaggtcctg catgccactt ctaacatgca gcgcacattg actaatgtgc gcaagctgtt    5040
gaagccagga ggcaaactca ttcttgtcga accaccagag acgagcttgg acttgttttt    5100
cactttcggg cttctgcccg gctggtggct cagcgaagaa ccagaaagac agtcgactcc    5160
gtcactaagc cctacgatgt ggcgcagcat gctgcacact actggattca atggtgtgga    5220
agttgaggct cgtgactgcg atagccacga gttctatatg attagcacca tgatgtccac    5280
ggccgtacag gcgactccga tgtcatgctc ggtcaaattg cctgaagtgc tcttggtcta    5340
tgttgactca tctacgccca tgtcttggat atcagatttg cagggagaga ttcgcggcag    5400
gaattgttcc gtcacttcgc tacaggcact tcgtcaagtt cctcctaccg agggccaaat    5460
atgcgtattc cttggagagg tggaacactc catgcttggt tcagtcacca acgacgactt    5520
```

-continued

```
cacactttg acctcaatgc tacagctggc tgggggaact ttatgggtca cccaaggagc   5580
gacaatgaag tctgatgatc ccctgaaggc tctacacctc ggattactac gtaccatgcg   5640
taatgaaagc catggcaagc gatttgtctc acttgacctc gacccttcgc gtaatccatg   5700
gacaggcgat tcgcgcgatg ccattgtcag tgttctggat ttaattagca tgtcagatga   5760
aaaggagttt gactatgcag agcgggatgg agttatccat gttcctcggg catttagtga   5820
ctccatcaat ggaggcgagg aagacgggta tgccttggag ccattccagg acagccagca   5880
tctcctgcga ctagatatac agactcctgg gctcctcgat tccctgcact tcacaaagcg   5940
caatgtggac acatatgaac cagataaatt accggacgac tgggtagaga ttgaaccgag   6000
ggcgtttggt cttaacttcc gtgacatcat ggtcgcgatg ggtcaattgg aatcaaacgt   6060
catgggcttc gaatgcgccg gcgtggttac aagtctcagc gagacagcaa gaacaattgc   6120
acccgggctt gcggtcggag atcgggtttg cgccctcatg aacggacact gggcgtcgag   6180
ggtgaccaca agccggacca acgtggtgcg cattccagag actcttagtt cccgcatgc   6240 tgcctccatc cctctggcct tcacaacagc ttacatttca ctttacaccg ttgcccgcat   6300
tctgccaggt gaaacggtgt tgatccatgc cggggcagga ggcgtaggcc aggcggccat   6360
tattcttgct caattaaccg gtgctgaagt ctttacaact gctggcagtg agaccaagcg   6420 taacctttg atcgataaat tccacctcga ccctgatcat gtcttctcga gcagggactc   6480
cagcttcgtc gacggtatca agacccgcac ccgtggcaag ggggtggacg tggttttgaa   6540
ctcgctagct gggcctctcc ttcagaagag ctttgactgt ctggctaggt ttggtcggtt   6600
tgtagaaatc ggcaagaagg atcttgagca gaatagccga ctcgacatgt cgacgttcgt   6660
ccgcaatgtc tccttctcct ccgttgatat tctctactgg cagcaagcga agcccgctga   6720
aatcttccag gcgatgtccg aggtcatctt gctgtgggag cgaacggcaa tcggcctgat   6780
tcatccaata tcagagtatc ctatgtcggc cctggagaag gcctttcgca ctatgcagag   6840
cggccagcac gttgggaaga ttgttgtgac agtagccccc gatgacgcgg tcctcgttcg   6900
tcaggaacga atgccactat ttctgaagcc taacgtgtcg tatcttgttg ctgggggcct   6960
gggtggtatc ggacggcgga tctgcgagtg gctggtcgat cgcggggcgc gatatctcat   7020
cattctgtct cgaactgctc gcgtggaccc ggtcgtgacg agtctccaag agcggggctg   7080
caccgtttct gtacaggcgt gtgatgtggc cgatgaaagc cagcttgaag cggctctcca   7140
acagtgtcgg gcggaggaaa tgcctccgat tcgggcgtc atccaagggg caatggttct   7200
caaggacgcc ctcgtctcgc aaatgacggc ggacgggttc catgccgccc tgcggcccaa   7260
ggttcaggga agttggaatc tgcaccgaat tgcatcggac gtggatttct tcgtgatgct   7320
ctcatccttg gtgggtgtca tgggaggcgc aggacaagcc aactacgcgg ctgccggagc   7380
gtttcaggac gcgctcgcag agcaccgcat ggctcacaac cagccagcgg tcaccatcga   7440
cctcggaatg gtccagtcaa ttgggtatgt agcagagaca gattctgctg tggcggaacg   7500
actccaacgg atcggctatc aaccccttgca cgaagaggag gttctggacg tcctcgagca   7560
agctatatct cctgtgtgtt ccctgccgc acccacacgg cctgctgtca tcgtcaccgg   7620
catcaacacc cgcccaggcc ctcactgggc acacgccgac tggatgcaag aggctcgctt   7680 tgcgggatc aagtatcgtg atccgttgag ggacaatcat ggagctttgt cgctgacccc   7740
ggcggaagat gacaatcttc acgccaggct gaaccgtgca atcagccaac aggagtcaat   7800
cgccgtgatc atgaggcga tgagctgcaa gctcatctca atgttcggcc tgacggatag   7860
cgaaatgtcc gccactcaga cattggcggg gatcggcgtg gactccctgg tcgccattga   7920
```

```
gctccggaac tggatcacag ctaagttcaa tgttgatatc tcagttttcg agttgatgga    7980
gggccgaacg atcgccaaag tcgcggaagt ggtgctgcag agatacaaag cttag         8035

<210> SEQ ID NO 30
<211> LENGTH: 888
<212> TYPE: DNA
<213> ORGANISM: Aspergillus terreus

<400> SEQUENCE: 30
atggcgacgc aggaattctt aagcgatgtc tcctccggat tcttgtctgc tgaagccata     60
aggtacagag tgaagacggg tgtatccatg gatggatgga tgtatgtgga gatggcacct    120
tacatataaa tatacatcat atcaggaaaa ggggatattc gtgtaactct gtgcgaaccg    180
acgataaaca tcacttaaga cacctaacca atatagggtt agacacgcct ccgtgtccca    240
aatcccttcc ggctgcgcac tcggcggtag catcttgtct cacgttcgtt ccgccggacc    300
catgtgaaaa ttgggaggcg ctgcaggtag cgtgggacaa ggcttgttgc aggaatccaa    360
cgccgttgtt ctttatctgc gtttctcttc tgttttcttt ctattccctc tggctgcagc    420
gtggcgggtg cgggcgatat ggtgggttgc accgtgtctc taaagtgttt cccaaagtat    480
ggcccgacga catggattcc cagctaccct caagactaca aaccttagta agtagtaagt    540
agcttcatag acctatccta attaacctac actaactaaa cccagcacgt ctgggggtt    600 tcaacccgta atctgcagca gatcctagag cgtaaacccg aacctgcccc aaacaactct    660
acatacatct caagggcta tgcaacattc ttcaaccaat tttccttacc atccgtagat    720
gttacacaga tcctcaatca gacgttgcag caccacgatg ttgagactat taacctggat    780
tgtggcagtg gcctcttaac cctgcggacc cagctaagga tcttattgat agggaaacct    840
aagataataa aaccatttc cggtctacgg acgagcatta atgaataa                  888

<210> SEQ ID NO 31
<211> LENGTH: 2478
<212> TYPE: DNA
<213> ORGANISM: Aspergillus terreus

<400> SEQUENCE: 31
atggagagtg cagagctgtc gtcgaagcgg caggcatttc ctgcatgtga tgagtgccgg     60
atccgtaagg tccgatgcag caaggagggt ccaaagtgct cccattgcct ccgatataac    120
ctaccctgtg aattctccaa caaagttaca cgggtcaacc aaacagcaaa attgtaagtg    180
ataagatggt ctatatttgg gtcaaatacc tgtctttctg actctcagtc agggcgcgcg    240
acgtcgagaa gctcgggagt cgggttggag atatcgaaca tgccctccaa cgatgcctgt    300
cctttattga tgcccatcag ggctttcgtg atctatcaag gccacagtca aagaaagcg    360 ggtacacaag ctcaaccagc tcagaagagt gtgaagtaaa cttgtactca ggcaaacaca    420
cttcacccac cgaggaagat ggattctggc ctctccacgg ttatggctct tttgtttcac    480
tcgtcatgga ggcacaggct gctaacgcca acctaacctc ttggttaccg gtcgatatga    540
ccagcggcca agtcgcagag atggtcgcat ttgaccgcca agctgtgtca gctgtgcgct    600
cgaaggtggc tgaggcgaat gaaacgcttc aacagatcat tgaggatatc ccaacactat    660
cggcatccga aaacgatacc tttctcccgt ctcttccacc ccgcgctcta gtggagccgt    720
ctatcaacga atatttcaag aagctgcatc cacgactccc tatatttagt cgacagacta    780
ttatggacgc agtggaatct cagtacacaa tcagaactgg gcctccggac ctggtttgga    840
ttacctcttt caactgcatt gtgcttcagg ccctgactca acatcaatt gcgaacaaag    900
```

-continued

```
tcgtgggatg cacaggacaa gacataccaa tagattatat gatcataagc ctgctgcgta      960
atatcaggca gtgctataat cgattggaaa ctcttgttaa accccggcta tcgaatatac     1020
gggccctctt ttgtttggtg cgtcttacaa ccctacctt ggaacgtggc ctgactttat      1080
tatactaagg cacttgtggc aatggagtat tttgatttcg caattttct gactatcttt      1140
gctcaagtct gcgagttgtc caggctcatt ggactccatt taacgacaac gaccccgcca    1200
acggaagatg gggctgtggg cgaccagcct aaagacttgt tctggagcat cttcctcgtc    1260
gatgttcgtc aaaaacttgc ttcgttttct gagcatttcg cttactatag gatttagaag    1320
cacgtatcca tcattggggg caaggcctgc ctattgccct cgtatgactg cagcgtacca    1380
ttgcctccat atgactccgc tgcgccacta ccaaatgctt ttgcggcacg catacgcttg    1440
gcattcattc ttgaggagat atatctgggc ttatactcag caaaatccag caaaatggaa    1500
cagagtcgcg tccgccgccg tatccgcaga attgctcgaa aacttagcca gtggcacgtg    1560
caacatgagc atgtactgcg taccggagat ccgaataggc ctctcgaaga gtatatctgt    1620
gcaacgcagt tgaggtttgc actctcgagc tgttgggtac ttctgcataa acgcatttgg    1680
agccaggaaa ggggcgctgt ctgcctacaa cacgctcggg attgtctgat gctgttcaag    1740
caattgtgcg atgggtgtaa atctggtttc agcaatttcg acaggtaagt cttccgtgcg    1800
accctcttga cagcatccta acctggggat gtacttcata gcattgtcct gaactattct    1860
ttgatctcat tcatgggaat ctatgtccac attgtggagg aagaccagcc gatccattca    1920
caggacatgg agatactcac tttcttcgcc atatacacga accgttcggc atccaatagg    1980
tcatctgcat ctatctcgta caaattaagc caagtggcca gtcgctgtag cgatattgcc    2040
ctcctcctcc agaatttaag ggagaggcgt tttattccga caacgatatc acgaagtcca    2100
acgccctcat ggaacgagcc aacctacatg gattacgatg tcgccaatgc gtccactagc    2160
acaactagca ccggctcttc atataacttg aatatcagcc cgcttggtgt acccggagac    2220
ggccaggtct gggacatata cttcaacccg agagaaatac caatggatgg tacaattgcg    2280
actccttctg aggatgcaac ccaggatttg ctgagcaatg atgctggcca atgccttggt    2340
ttccccgact tttcacttgg cattgacaac ttctccgact ttccacttgg cattgacatg    2400
actagccaaa gcgaatttgg tcttattatg gaggaggaca taattcgata tgagagacta    2460
ctagataggc ccgtttag                                                   2478
```

<210> SEQ ID NO 32
<211> LENGTH: 1302
<212> TYPE: DNA
<213> ORGANISM: Aspergillus terreus

<400> SEQUENCE: 32

```
atggagtcta aagtccagac aaatgttcca ttaccaaagg caccccttac ccaaaaagcc       60
cgtgggaagc gtgtatgtgt tccttcttgg tcgcgcgtgt gccatgttac tgacaatgtc      120
ttctcttaat atatgtatag acgaaaggca ttcctgcatt ggtcgcgggt gcttgtgctg      180
gggcagttga aatctccatc acctacccct tcgaatgtga gcttatcctg tgtttaagag     240
ttccgcttta ccgtggccgc caactgacag tctattgctt ccgctggtag cggctaaaac     300
tcgcgcccag cttaagcgga gaaaccatga tgtggcagct ataaacctg gaatccgagg      360
ctggtatgct gggtatggag ccaccttggt aggaaccaca ttgaaagcct ccgttcgtat      420
gtagcgatcc cccttataag cccgcgtgga gcgaaaggga atgaccgttt gcaataacaa      480
acagaatttg cctccttcaa tatttatcgc tcggccctct cgggcccaaa tggagagctc      540
```

-continued

| | |
|---|---|
| tcaactggag cttccgtcct ggctgggttt ggggctggcg tgaccgaggc tgtcttagcc | 600 |
| gtaaccccag cggaggcgat caagacgaaa atgtaagttg caacatctca cccgttatcc | 660 |
| gatcagttct taattcgttc tcttagcatt gatgcaagga aggttggaaa tgcagagtta | 720 |
| agtacgactt tcggcgcgat agctggaatc cttcgagatc ggggaccgct tggattcttc | 780 |
| tctgcggttg gtcctacaat tttgcggcag tcgtccaatg cggcagtgaa gttcactgtt | 840 |
| tataacgaac ttattgggct ggcccgaaaa tactcgaaga acggcgaaga cgtgcaccct | 900 |
| ctggcaagca ccttggtcgg ttctgttact ggagtttgtt gcgcctggtc gacacagcca | 960 |
| ctggacgtga tcaagacgcg gtaagtgctg ctcagatcga cagtaacccg cccagataag | 1020 |
| tatatgctga cttggatgcg acttcgggtt accagaatgc aatctcttca ggcaagacaa | 1080 |
| ctgtacggaa ataccttta ctgcgtgaaa acacttctgc gcaatgaagg cattggggtt | 1140 |
| ttctggtccg gcgtctggtt tcggacaggg agactttccc ttacctcggc catcatgttt | 1200 |
| cccgtgtaag tttaggagta atctacaggc atgatattct tgtacactga cagagcgtca | 1260 |
| aggtacgaga aagtctacaa gttcttgacg cagccaaact ga | 1302 |

<210> SEQ ID NO 33
<211> LENGTH: 1529
<212> TYPE: DNA
<213> ORGANISM: Aspergillus terreus

<400> SEQUENCE: 33

| | |
|---|---|
| atgaccaagc aatctgcgga cagcaacgca aagtcaggag ttacggccga aatatgccat | 60 |
| tgggcatcca acctggccac tgacgacatc cctccggacg tattagaaag agcaaaatac | 120 |
| cttattctcg atggtattgc atgtgcctgg gttggtgcaa gagtgccttg gtcagagaag | 180 |
| tatgtgcagg caacaatgag cttttgagccg ccaggggcct gcagggtgat ggatatgga | 240 |
| caagttagtt ctatccaatc tgaacagtct acaaagtata ctgacgatcc tttgtataga | 300 |
| aactggggcc tgttgcagca gccatgacca attctgcttt catacaggct acggagcttg | 360 |
| acgactacca cagcgaagcc ccctacact ctgcaagcat tgtcctccct gcggtctttg | 420 |
| cagcaagtga ggtcttagcc gagcagggca aaacaatttc tggtatagct gtcattctag | 480 |
| ccgccattgt ggggtttgaa tctggcccgc ggatcggcaa agcaatctac ggatcggacc | 540 |
| tcttgaacaa cggctggcat tgtggagccg tgtatggtgc tccagccggt gcgctggcca | 600 |
| caggaaagct ccttggtctg actccagact ccatggaaga tgctctcgga atcgcgtgca | 660 |
| cgcaagcctg tggcttaatg tcggcgcaat acggaggcat ggtcaagcgc gtgcaacatg | 720 |
| gattcgcagc gcgtaatggt cttcttgggg gactgttggc ccatggtggg tacgaggcca | 780 |
| tgaagggtgt cctggagaga tcttacgcg gtttcctcaa aatgttcacc aagggcaatg | 840 |
| gcagagagcc tccctacaaa gaggaggaag tggtggccgg tctcggttca ttctggcata | 900 |
| cctttactat tcgcatcaag ctctatgcct gctgcgact tgtccatggt ccagtcgaag | 960 |
| ctatcgaaaa ccttcagagg aggtaccccg agctcttgaa tagagccaac ctcagcaaca | 1020 |
| ttcgccacgt tcatgtacag ctttcaacag cctcgaacag tcactgtgga tggataccag | 1080 |
| aggagagacc catcagttca atcgcagggc agatgagtgt cgcatacatc ctcgccgtcc | 1140 |
| agttggtcga ccagcaatgt cttctggccc agttttccga gtttgatgac aacttggaga | 1200 |
| ggccagaagt gtgggatctg gccaggaagg ttactccatc tcatagcgaa gagtttgatc | 1260 |
| aagacggcaa ctgtctcagt gcgggtcgcg tgaggattga gttcaacgat ggctcttctg | 1320 |
| ttacggaaac tgtcgagaag cctcttggag tcaaagagcc catgccaaac gaacggattc | 1380 |

```
ttcacaaata ccgaacccctt gctggtagcg tgacggacga aacccgggtg aaagagattg   1440
aggatcttgt cctcagcctg dacaggctca ccgacattag cccattgctg gagctgctta   1500
attgtcccgt aaaatcgcca ctggtataa                                    1529

<210> SEQ ID NO 34
<211> LENGTH: 1704
<212> TYPE: DNA
<213> ORGANISM: Aspergillus terreus

<400> SEQUENCE: 34
atgggccgcg gtgacactga gtccccgaac ccagcgacga cctcggaagg tagcggacaa     60
aacgagccag agaaaaaggg ccgtgatatt ccattatgga gaaatgtgt cattacgttt    120 gttgttagtt ggatgactct agtcgttact ttctccagta cttgtcttct tcctgccgcc    180
cctgaaatcg cgaatgaatt tgatatgact gtcgagacta tcaatatctc caatgctggt    240
gtcttggttg ccatgggata ttcatccctc atatggggtc ccatgaacaa gttagtcggc    300
aggcggacat catacaatct ggccatttca atgctttgtg cgtgctccgc tggaacggca    360
gcggcgataa acgagaaaat gttcatagcg ttcagagtat tgagcggctt aaccggaacc    420
tcgttcatgg tctcaggcca aactgttctt gcagatatct ttgagcctgt acgcatcaca    480
cgcccttgtc tccccaattg cgaaaactaa tccgttcgtg cgcaggttta ccgtgggacg    540
gccgtaggtt tcttcatggc cgggactctt tctggccctg caataggtac gtaccctgct    600
gaaagtacta gaactcccaa caggaactga ctgtttgatc aggcccctgc gtgggagggg    660
tcatcgtcac tttcacgagt tggcgtgtta tcttctggct tcaactaggt atgagcggac    720
tggggctcgt gctttccctg ctattttccc gaaaatcga aggaacttct gagaaggtct    780
caacggcgtt taaaccgacc acacttgttt caatcatatc gaaattctcc ccaacggatg    840
tgctcaagca gtgggtgtat ccaaatgtct tccttgccgt aagtgcctgg gagatatgcc    900
ctctgcatct actggaaacg aaatgctcat gccgcaaaca aaaggactta tgctgtggcc    960
tcctggcgat tacgcaatat tcgatcctga cttcagctcg tgctatattc aactcacggt   1020
ttcatttaac gactgcccta gtatcgggtc tcttctacct cgctccaggt gccgggttcc   1080
tgataggagg tctcgtcggc ggtaaacttt cggatcgcac cgttcggaga tacatagtaa   1140
agcgcggatt ccgtctccct caggatcgac tccacagcgg gctcatcaca ttgtttgccg   1200
tgctgcctgc gggaacgctc atttacgggt ggacactcca agaggataag ggtgggatgg   1260
tagtgcccat aatcgcggcg ttcttcgcgg gctgggggct catgggcagt tttaactgcc   1320
tgaacactta cgtggctggt tgttccaca ccctcattaa tttatcccct ttgtgtacat   1380
gcccacaata atgttgtctc tgaccgcaag tagaagcctt gccacggaac cggtctgcag   1440
tcattgcagg aaagtatatg attcaatact ccttttctgc agggagtagt gcgctcgttg   1500
tgcccgtcat agacgccctc ggagttggat ggacgttcac gctatgtatg gtaccttttct  1560 tcttacctct caatgtacat gctcacagtt gttgcaggtg tggttgcttc gactatagct   1620
ggattgatca cggcggccat cgcacggtgg gggataaata tgcaaaggtg ggcagaaagg   1680
gctttcaacc tgcctaccca atag                                        1704

<210> SEQ ID NO 35
<211> LENGTH: 1704
<212> TYPE: DNA
<213> ORGANISM: Aspergillus terreus
```

<400> SEQUENCE: 35

```
atgggccgcg gtgacactga gtccccgaac ccagcgacga cctcggaagg tagcggacaa      60
aacgagccag agaaaaaggg ccgtgatatt ccattatgga gaaaatgtgt cattacgttt     120
gttgttagtt ggatgactct agtcgttact ttctccagta cttgtcttct tcctgccgcc     180
cctgaaatcg cgaatgaatt tgatatgact gtcgagacta tcaatatctc caatgctggt     240
gtcttggttg ccatgggata ttcatccctc atatggggtc ccatgaacaa gttagtcggc     300
aggcggacat catacaatct ggccatttca atgctttgtg cgtgctccgc tggaacggca     360
gcggcgataa acgagaaaat gttcatagcg ttcagagtat tgagcggctt aaccggaacc     420
tcgttcatgg tctcaggcca aactgttctt gcagatatct ttgagcctgt acgcatcaca     480
cgcccttgtc tccccaattg cgaaaactaa tccgttcgtg cgcaggttta ccgtgggacg     540
gccgtaggtt tcttcatggc cgggactctt tctggccctg caataggtac gtaccctgct     600
gaaagtacta gaactcccaa caggaactga ctgtttgatc aggcccctgc gtgggagggg     660
tcatcgtcac tttcacgagt tggcgtgtta tcttctggct tcaactaggt atgagcggac     720
tggggctcgt gctttccctg ctattttttcc cgaaaatcga aggaacttct gagaaggtct     780
caacggcgtt taaaccgacc acacttgttt caatcatatc gaaattctcc ccaacggatg     840
tgctcaagca gtgggtgtat ccaaatgtct tccttgccgt aagtgcctgg gagatatgcc     900
ctctgcatct actggaaacg aaatgctcat gccgcaaaca aaaggactta tgctgtggcc     960
tcctggcgat tacgcaatat tcgatcctga cttcagctcg tgctatattc aactcacggt    1020
ttcatttaac gactgcccta gtatcgggtc tcttctacct cgctccaggt gccgggttcc    1080
tgatagggag tctcgtcggc ggtaaacttt cggatcgcac cgttcggaga tacatagtaa    1140
agcgcggatt ccgtctccct caggatcgac tccacagcgg gctcatcaca ttgtttgccg    1200
tgctgcctgc gggaacgctc atttacgggt ggacactcca agaggataag ggtgggatgg    1260
tagtgcccat aatcgcggcg ttcttcgcgg gctgggggct catgggcagt tttaactgcc    1320
tgaacactta cgtggctggt ttgttccaca ccctcattaa tttatcccct ttgtgtacat    1380
gcccacaata atgttgtctc tgaccgcaag tagaagcctt gccacggaac cggtctgcag    1440
tcattgcagg aaagtatatg attcaatact cctttctgc agggagtagt gcgctcgttg    1500
tgcccgtcat agacgccctc ggagttggat ggacgttcac gctatgtatg gtacctttct    1560
tcttacctct caatgtacat gctcacagtt gttgcaggtg tggttgcttc gactatagct    1620
ggattgatca cggcggccat cgcacggtgg gggataaata tgcaaaggtg ggcagaaagg    1680
gctttcaacc tgcctaccca atag                                           1704
```

<210> SEQ ID NO 36
<211> LENGTH: 1503
<212> TYPE: DNA
<213> ORGANISM: Aspergillus terreus

<400> SEQUENCE: 36

```
atgaagcccg caatccttat gaaatactgg ctcttcgtct cagctgtgag cgcgtcaacc      60
ctgaacggca agctcacatt gagtgagaca aaggtgacgg gggccgttca gctggcttgt     120
accaatagtc caccggacat ctatatcgac cccgatgatt cggtctcagt ggttcgcgca     180
gcccacgatc tggccctgga ctttgggcgc gtctttggta aaaatgccac agttcgcttc     240
actaacgaga ctcatccaac atcgatggcc atcatcgctg gtaccataga taagtcaacc     300
ttccttcaga ggttgatagc ggatcataag ctcgacgtta ccagcatccg tggccagtgg     360
```

-continued

```
gaatcctatt catcagcact ggtgttgggt ccagccaaag gcatacagaa tgcgctagtc    420
atagctggca gtgaccgtcg tggggccatc tatggcttat acgatatatc tgaacaaatt    480
ggcgtctcgc cattgttctg gtggacggat gttaccccaa ccaaacttga tgccatctac    540
gcgctagatg ttcagaaagt ccagggtcca ccgtcagtga agtatcgtgg aatttttatc    600
aacgacgaag cgcccgcctt gcataactgg attcttgcaa attatggcga ggttgagaac    660
ggggaccctg ccttcatctc acgtttctac gcccatgtct tcgagctgat cctgcgcctg    720
aaagggaatt acctctggcc ggcgatgtgg tcaaatatgt tttatgttga tgacaccaac    780
aatgcccac tagcggacta ctacggagtg gtaatgggca ctagccacac tggtatgacg    840
gttgggactc cctgcttgaa agcccatgct gactacgaaa agaaccgat ggctcgagca    900
acaaacgagc aatcccagtt tctaaacggg acgtgggact ggattagcaa cgaggtcaat    960
gttaaagcat ttatgaggga gggtgtaatt aggagccaac actgggagac cgcatacaca   1020
atgggcatgc ggggtctagg cgatgctgca tcgccgacac ttaacgcaac agtggaagaa   1080
agcattgtta gctggcagga atccgtgcta tcggacatcc tgaataaaac caacctgtcg   1140
aacgtggttc aaccatttgt cctatttgat gttaggatcc attcaccctc aaatatatcg   1200
tttgctgact gccaggtctg tgacacagga actgggaact tactatgaga gcggcatgac   1260
tgtaccagac caggtcacat tgatatatcc tgatgacaat gcaggcaata tgctgcgtct   1320
cccattgcag aatgaaactg ggcgttctgg gggcgcagga atttactatc attttgacat   1380
gaacgcgccg ccgcgctgtt acaagtggat caacacagct caactgatca ggacctggga   1440
tcaactgcgc gcggcataca gccacggtgc tcagacagta tgggttgcca atattgggga   1500
tat                                                                 1503
```